(12) United States Patent
Friedlander et al.

(10) Patent No.: US 7,931,891 B2
(45) Date of Patent: Apr. 26, 2011

(54) ISOLATED MYELOID-LIKE BONE MARROW CELL POPULATIONS AND METHODS OF TREATMENT THEREWITH

(75) Inventors: Martin Friedlander, Del Mar, CA (US); Matthew R. Ritter, Oceanside, CA (US); Stacey K. Moreno, Spring Valley, CA (US)

(73) Assignee: The Scripps Research Institute, La Jolla, CA (US)

( * ) Notice: Subject to any disclaimer, the term of this patent is extended or adjusted under 35 U.S.C. 154(b) by 712 days.

(21) Appl. No.: 11/884,958

(22) PCT Filed: Feb. 24, 2006

(86) PCT No.: PCT/US2006/006411
§ 371 (c)(1),
(2), (4) Date: Aug. 23, 2007

(87) PCT Pub. No.: WO2006/104609
PCT Pub. Date: Oct. 5, 2006

(65) Prior Publication Data
US 2008/0194018 A1    Aug. 14, 2008

Related U.S. Application Data

(60) Provisional application No. 60/656,037, filed on Feb. 24, 2005.

(51) Int. Cl.
*A01N 65/00* (2009.01)
*A01N 1/02* (2009.01)
*A01K 48/00* (2006.01)

(52) U.S. Cl. ............. 424/93.1; 424/93.2; 424/93.21; 435/2; 435/325

(58) Field of Classification Search .............. None
See application file for complete search history.

(56) References Cited

U.S. PATENT DOCUMENTS

| | | | |
|---|---|---|---|
| 7,153,501 B2 * | 12/2006 | Friedlander et al. | 424/93.21 |
| 2002/0028783 A1 * | 3/2002 | O'Brien et al. | 514/44 |
| 2002/0071833 A1 * | 6/2002 | Boyd | 424/93.21 |

OTHER PUBLICATIONS

Kansas et al. Blood 1990;76:2483-92.*
King et al. J Nutr 2002;132: 3301-3307.*
Felzmann et al. Brit J Haematol 1993;84:428-35.*
Moll et al. J Clin Invest 1998;102:1024-34.*
Köller et al. Scand J Immunol 1996;43:626-32.*

\* cited by examiner

*Primary Examiner* — Q. Janice Li
(74) *Attorney, Agent, or Firm* — Olson & Cepuritis, Ltd.

(57) ABSTRACT

The present invention provides an isolated myeloid-like cell population comprising a majority of cells that are lineage negative, and which express both CD44 antigen, CD11b antigen, and hypoxia inducible factor 1 α (HIF-1 α). These cells have beneficial vasculotrophic and neurotrophic activity when intraocularly administered to the eye of a mammal, particularly a mammal suffering from an ocular degenerative disease. The myeloid-like cells are isolated by treating bone marrow cells, peripheral blood cells or umbilical cord cells with an antibody against CD44 (hyaluronic acid receptor), against CD11b, CD14, CD33, or against a combination thereof and using flow cytometry to positively select CD44 and/or CD11b expressing cells therefrom. The isolated myeloid-like bone marrow cells of the invention can be transfected with a gene encoding a therapeutically useful protein, for delivering the gene to the retina.

11 Claims, 47 Drawing Sheets

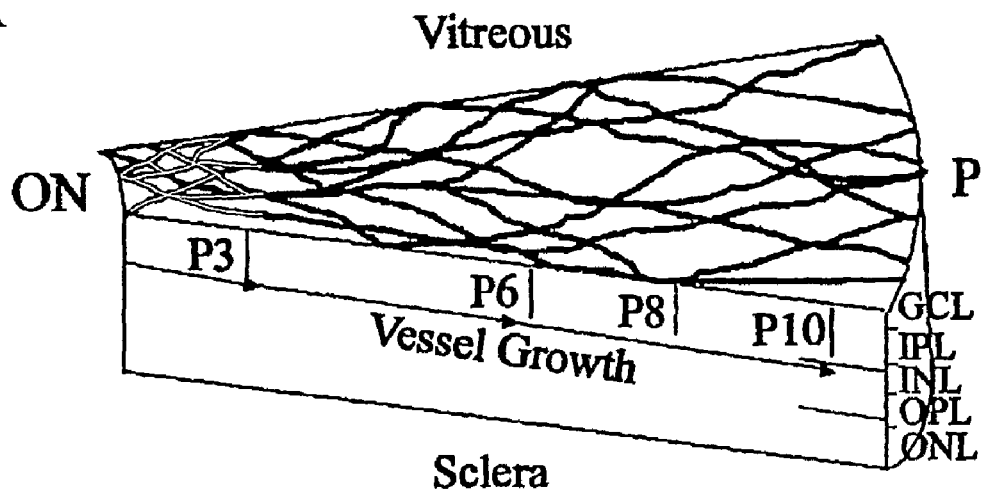
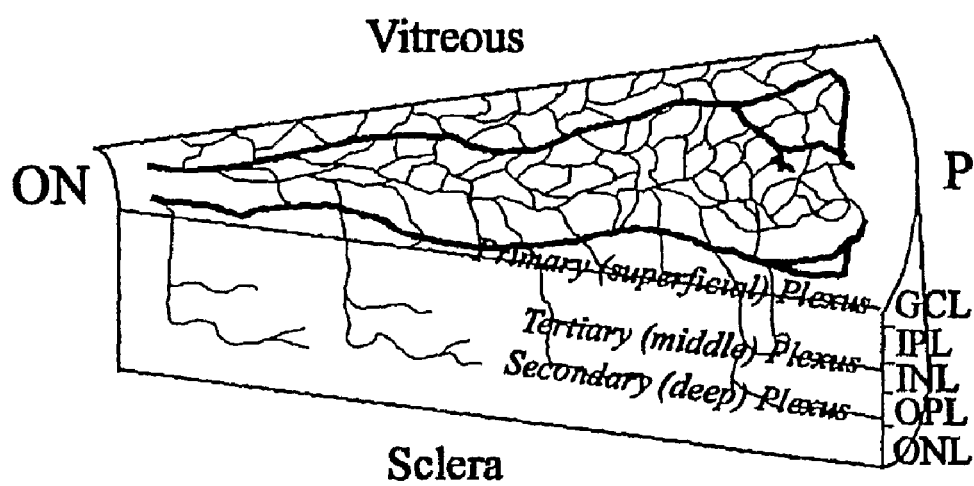
FIG. 1

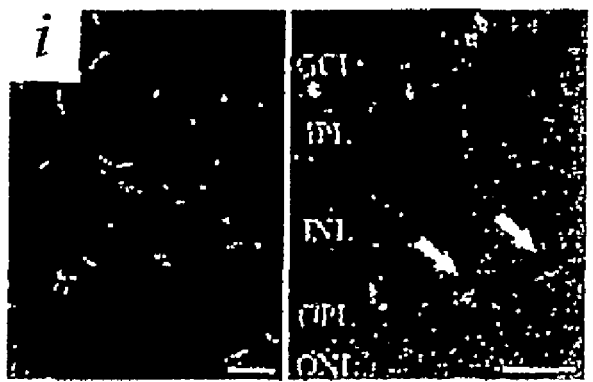
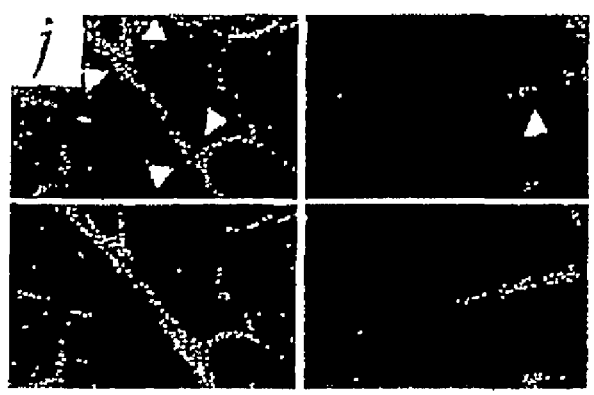
FIG. 2 Cont.

DNA encoding His-tagged T2 fragment of human TrpRS

```
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta taagggattt tgccgatttc ggcctattgg ttaaaaaatg agctgattta 420
acaaaaattt aacgcgaatt ttaacaaaat attaacgttt acaatttcag gtggcacttt 480
tcggggaaat gtgcgcggaa cccctatttg tttattttc taaatacatt caaatatgta 540
tccgctcatg agacaataac cctgataaat gcttcaataa tattgaaaaa ggaagagtat 600
gagtattcaa catttccgtg tcgcccttat tccctttttt gcggcatttt gccttcctgt 660
ttttgctcac ccagaaacgc tggtgaaagt aaaagatgct gaagatcagt tgggtgcacg 720
agtgggttac atcgaactgg atctcaacag cggtaagatc cttgagagtt ttcgccccga 780
agaacgtttt ccaatgatga gcacttttaa agttctgcta tgtggcgcgg tattatcccg 840
tattgacgcc gggcaagagc aactcggtcg ccgcatacac tattctcaga atgacttggt 900
tgagtactca ccagtcacag aaaagcatct tacggatggc atgacagtaa gagaattatg 960
cagtgctgcc ataaccatga gtgataacac tgcggccaac ttacttctga caacgatcgg 1020
aggaccgaag gagctaaccg cttttttgca caacatgggg gatcatgtaa ctcgccttga 1080
tcgttgggaa ccggagctga atgaagccat accaaacgac gagcgtgaca ccacgatgcc 1140
tgcagcaatg gcaacaacgt tgcgcaaact attaactggc gaactactta ctctagcttc 1200
ccggcaacaa ttaatagact ggatggaggc ggataaagtt gcaggaccac ttctgcgctc 1260
ggcccttccg gctggctggt ttattgctga taaatctgga gccggtgagc gtgggtctcg 1320
cggtatcatt gcagcactgg ggccagatgg taagccctcc cgtatcgtag ttatctacac 1380
gacggggagt caggcaacta tggatgaacg aaatagacag atcgctgaga taggtgcctc 1440
actgattaag cattggtaac tgtcagacca agtttactca tatatacttt agattgattt 1500
aaaacttcat ttttaattta aaggatcta ggtgaagatc ctttttgata atctcatgac 1560
caaaatccct taacgtgagt tttcgttcca ctgagcgtca gaccccgtag aaaagatcaa 1620
aggatcttct tgagatcctt tttttctgcg cgtaatctgc tgcttgcaaa caaaaaaacc 1680
accgctacca gcggtggttt gtttgccgga tcaagagcta ccaactcttt ttccgaaggt 1740
aactggcttc agcagagcgc agataccaaa tactgtcctt ctagtgtagc cgtagttagg 1800
ccaccacttc aagaactctg tagcaccgcc tacatacctc gctctgctaa tcctgttacc 1860
agtggctgct gccagtggcg ataagtcgtg tcttaccggg ttggactcaa gacgatagtt 1920
accggataag gcgcagcggt cgggctgaac ggggggttcg tgcacacagc ccagcttgga 1980
gcgaacgacc tacaccgaac tgagatacct acagcgtgag ctatgagaaa gcgccacgct 2040
tcccgaaggg agaaaggcgg acaggtatcc ggtaagcggc agggtcggaa caggagagcg 2100
cacgagggag cttccagggg gaaacgcctg gtatctttat agtcctgtcg ggtttcgcca 2160
cctctgactt gagcgtcgat ttttgtgatg ctcgtcaggg gggcggagcc tatggaaaaa 2220
cgccagcaac gcggcctttt tacggttcct ggccttttgc tggccttttg ctcacatgtt 2280
ctttcctgcg ttatccctg attctgtgga taacgtatt accgccttg agtgagctga 2340
taccgctcgc cgcagccgaa cgaccgagcg cagcgagtca gtgagcgagg aagcggaaga 2400
gcgcctgatg cggtattttc tccttacgca tctgtgcggt atttcacacc gcatatatgg 2460
tgcactctca gtacaatctg ctctgatgcc gcatagttaa gccagtatac actccgctat 2520
cgctacgtga ctgggtcatg gctgcgcccc gacaccgcc aacaccgct gacgcgcct 2580
gacgggcttg tctgctcccg gcatccgctt acagacaagc tgtgaccgtc tccgggagct 2640
gcatgtgtca gaggttttca ccgtcatcac cgaaacgcgc gaggcagctg cggtaaagct 2700
catcagcgtg gtcgtgaagc gattcacaga tgtctgcctg ttcatccgcg tccagctcgt 2760
tgagtttctc cagaagcgtt aatgtctggc ttctgataaa gcgggccatg ttaagggcgg 2820
ttttttcctg tttggtcact gatgcctccg tgtaaggggg atttctgttc atgggggtaa 2880
tgataccgat gaaacgagag aggatgctca cgatacgggt tactgatgat gaacatgccc 2940
ggttactgga acgttgtgag ggtaaacaac tggcggtatg gatgcggcgg gaccagagaa 3000
aaatcactca gggtcaatgc cagcgcttcg ttaatacaga tgtaggtgtt ccacagggta 3060
gccagcagca tcctgcgatg cagatccgga acataatggt gcagggcgct gacttccgcg 3120
tttccagact ttacgaaaca cggaaaccga agaccattca tgttgttgct caggtcgcag 3180
acgttttgca gcagcagtcg cttcacgttc gctcgcgtat cggtgattca ttctgctaac 3240
cagtaaggca accccgccag cctagccggg tcctcaacga caggagcacg atcatgcgca 3300
```

FIG. 7

```
cccgtggcca ggacccaacg ctgcccgaga tctcgatccc gcgaaattaa tacgactcac 3360
tatagggaga ccacaacggt ttccctctag aaataatttt gtttaacttt aagaaggaga 3420
tatacat atg agt gca aaa ggc ata gac tac gat aag ctc att gtt cgg 3469
ttt gga agt agt aaa att gac aaa gag cta ata aac cga ata gag aga 3517
gcc acc ggc caa aga cca cac cac ttc ctg cgc aga ggc atc ttc ttc 3565
tca cac aga gat atg aat cag gtt ctt gat gcc tat gaa aat aag aag 3613
cca ttt tat ctg tac acg ggc cgg ggc ccc tct tct gaa gca atg cat 3661
gta ggt cac ctc att cca ttt att ttc aca aag tgg ctc cag gat gta 3709
ttt aac gtg ccc ttg gtc atc cag atg acg gat gac gag aag tat ctg 3757
tgg aag gac ctg acc ctg gac cag gcc tat ggc gat gct gtt gag aat 3805
gcc aag gac atc atc gcc tgt ggc ttt gac atc aac aag act ttc ata 3853
ttc tct gac ctg gac tac atg ggg atg agc tca ggt ttc tac aaa aat 3901
gtg gtg aag att caa aag cat gtt acc ttc aac caa gtg aaa ggc att 3949
ttc ggc ttc act gac agc gac tgc att ggg aag atc agt ttt cct gcc 3997
atc cag gct gct ccc tcc ttc agc aac tca ttc cca cag atc ttc cga 4045
gac agg acg gat atc cag tgc ctt atc cca tgt gcc att gac cag gat 4093
cct tac ttt aga atg aca agg gac gtc gcc ccc agg atc ggc tat cct 4141
aaa cca gcc ctg ttg cac tcc acc ttc ttc cca gcc ctg cag ggc gcc 4189
cag acc aaa atg agt gcc agc gac cca aac tcc tcc atc ttc ctc acc 4237
gac acg gcc aag cag atc aaa acc aag gtc aat aag cat gcg ttt tct 4285
gga ggg aga gac acc atc gag gag cac agg cag ttt ggg ggc aac tgt 4333
gat gtg gac gtg tct ttc atg tac ctg acc ttc ttc ctc gag gac gac 4381
gac aag ctc gag cag atc agg aag gat tac acc agc gga gcc atg ctc 4429
acc ggt gag ctc aag aag gca ctc ata gag gtt ctg cag ccc ttg atc 4477
gca gag cac cag gcc cgg cgc aag gag gtc acg gat gag ata gtg aaa 4525
gag ttc atg act ccc cgg aag ctg tcc ttc gac ttt cag aag ctt gcg 4573
gcc gca ctc gag cac cac cac cac cac cac tgagatccgg ctgctaacaa 4623
agcccgaaag gaagctgagt tggctgctgc caccgctgag caataactag cataacccct 4683
tggggcctct aaacgggtct tgagggtttt tttgctgaaa ggaggaacta tatccggat 4742
```

FIG. 7 Cont.

His-tagged T2 fragment of human TrpRS

```
Met Ser Ala Lys Gly Ile Asp Tyr Asp Lys Leu Ile Val Arg Phe Gly
 1           5                   10                      15
Ser Ser Lys Ile Asp Lys Glu Leu Ile Asn Arg Ile Glu Arg Ala Thr
             20                  25                  30
Gly Gln Arg Pro His His Phe Leu Arg Arg Gly Ile Phe Phe Ser His
         35                  40                  45
Arg Asp Met Asn Gln Val Leu Asp Ala Tyr Glu Asn Lys Lys Pro Phe
     50                  55                  60
Tyr Leu Tyr Thr Gly Arg Gly Pro Ser Ser Glu Ala Met His Val Gly
 65              70                  75                      80
His Leu Ile Pro Phe Ile Phe Thr Lys Trp Leu Gln Asp Val Phe Asn
             85                  90                  95
Val Pro Leu Val Ile Gln Met Thr Asp Asp Glu Lys Tyr Leu Trp Lys
            100                 105                 110
Asp Leu Thr Leu Asp Gln Ala Tyr Gly Asp Ala Val Glu Asn Ala Lys
        115                 120                 125
Asp Ile Ile Ala Cys Gly Phe Asp Ile Asn Lys Thr Phe Ile Phe Ser
    130                 135                 140
Asp Leu Asp Tyr Met Gly Met Ser Ser Gly Phe Tyr Lys Asn Val Val
145                 150                 155                 160
Lys Ile Gln Lys His Val Thr Phe Asn Gln Val Lys Gly Ile Phe Gly
            165                 170                 175
Phe Thr Asp Ser Asp Cys Ile Gly Lys Ile Ser Pro Ala Ile Gln
            180                 185                 190
Ala Ala Pro Ser Phe Ser Asn Ser Phe Pro Gln Ile Phe Arg Asp Arg
        195                 200                 205
Thr Asp Ile Gln Cys Leu Ile Pro Cys Ala Ile Asp Gln Asp Pro Tyr
    210                 215                 220
Phe Arg Met Thr Arg Asp Val Ala Pro Arg Ile Gly Tyr Pro Lys Pro
225                 230                 235                 240
Ala Leu Leu His Ser Thr Phe Phe Pro Ala Leu Gln Gly Ala Gln Thr
            245                 250                 255
Lys Met Ser Ala Ser Asp Pro Asn Ser Ser Ile Phe Leu Thr Asp Thr
        260                 265                 270
Ala Lys Gln Ile Lys Thr Lys Val Asn Lys His Ala Phe Ser Gly Gly
        275                 280                 285
Arg Asp Thr Ile Glu Glu His Arg Gln Phe Gly Gly Asn Cys Asp Val
    290                 295                 300
Asp Val Ser Phe Met Tyr Leu Thr Phe Phe Leu Glu Asp Asp Lys Lys
305                 310                 315                 320
Leu Glu Gln Ile Arg Lys Asp Tyr Thr Ser Gly Ala Met Leu Thr Gly
                325                 330                 335
Glu Leu Lys Lys Ala Leu Ile Glu Val Leu Gln Pro Leu Ile Ala Glu
            340                 345                 350
His Gln Ala Arg Arg Lys Glu Val Thr Asp Glu Ile Val Lys Glu Phe
        355                 360                 365
Met Thr Pro Arg Lys Leu Ser Phe Asp Phe Gln Lys Leu Ala Ala Ala
    370                 375                 380
Leu Glu His His His His His His
385                 390
```

(A) Genes whose expression is increased 3-fold in Lin- HSC injected retinas

| Common Name | (normalized data) | | | Genbank | Keywords | p-value, call (A=absent, P=present) | | |
|---|---|---|---|---|---|---|---|---|
| | Lin (-) | CD31 (-) | NI rd/rd | | | Lin (-) | CD31 (-) | NI rd/rd |
| Tgtp | 11.86 | 0.53 | 0.66 | L38444 | T-cell-specific protein | 0.015 (P) | 0.162 (A) | 0.181 (A) |
| H-2D4(q) | 7.09 | 0.92 | 0.69 | X52914 | transplantation antigen | 0.016 (P) | 0.035 (A) | 0.054 (A) |
| H2-K2; H-2K2 | 4.51 | 0.70 | 0.55 | M27134 | cell surface glycoprotein | <0.001 (P) | 0.040 (P) | 0.120 (A) |
| Lzp-s | 6.51 | 0.65 | 0.99 | X51547 | lysozyme; lysozyme P | 0.015 (P) | 0.011 (A) | 0.003 (A) |
| Kcnj5 | 4.50 | 0.85 | 0.72 | U33631 | G-protein gated K+ channel | 0.037 (P) | 0.022 (A) | 0.084 (A) |
| Scya8 | 5.19 | 0.47 | 1.00 | AB023418 | MCP-2 precursor | 0.004 (P) | 0.060 (A) | 0.013 (A) |
| Ly6a | 4.02 | 0.96 | 0.79 | X04653 | Ly-6 alloantigen | 0.014 (P) | 0.014 (P) | 0.021 (A) |
| Pip5k1c | 3.40 | 0.94 | 0.78 | AB006916 | phosphatidylinositolkinase | 0.012 (P) | 0.013 (A) | 0.035 (A) |
| MAD | 3.76 | 0.56 | 0.89 | X83106 | MAX dimerization protein | 0.013 (P) | 0.080 (A) | 0.078 (A) |
| Cxadr | 3.98 | 0.81 | 1.00 | U90715 | coxsackie-adnovirus receptor | 0.011 (P) | 0.011 (P) | <0.001 (P) |
| Isg15 | 2.22 | 0.64 | 0.45 | X56602 | interferon inducible protein | 0.010 (P) | 0.086 (A) | 0.129 (A) |
| YY1 | 2.97 | 0.85 | 0.87 | M74590 | delta-transcription factor | 0.039 (P) | 0.040 (A) | 0.006 (A) |
| Psmb9 | 3.29 | 0.49 | 0.97 | D44456 | polypeptide complex subunit 2 | 0.015 (P) | <0.001 (A) | 0.043 (A) |

(B) Crystallin genes

| Common Name | (normalized data) | | | Genbank | Keywords | p-value, call (A=absent, P=present) | | |
|---|---|---|---|---|---|---|---|---|
| | Lin (-) | CD31 (-) | NI rd/rd | | | Lin (-) | CD31 (-) | NI rd/rd |
| Crybb2 | 8.73 | 0.55 | 0.83 | M60559 | beta-B2-crystallin | 0.008 (P) | 0.047 (A) | 0.085 (A) |
| Cryaa | 4.00 | 0.57 | 1.00 | J00376 | alpha-A-crystallin | 0.002 (P) | 0.015 (A) | 0.003 (A) |
| CrygD | 2.09 | 0.74 | 0.97 | AJ224342 | gamma-D-crystallin | 0.017 (P) | <0.001 (P) | 0.033 (P) |
| Cryba1 | 6.52 | 0.93 | 0.60 | AJ239052 | beta-A3/A1-crystallin | 0.007 (P) | 0.036 (P) | 0.055 (A) |
| Crygs | 2.89 | 0.97 | 0.85 | AF032995 | gamma-S-crystallin | 0.007 (P) | 0.017 (P) | 0.006 (P) |
| CrygC | 5.07 | 1.00 | 0.83 | Z22574 | gamma-C-crystallin | 0.029 (P) | <0.001 (A) | 0.004 (A) |
| CrygF | 1.94 | 1.00 | 0.69 | AJ224343 | gamma-F-crystallin | 0.010 (P) | 0.007 (P) | <0.001 (A) |

FIG. 20 Cont.

(C) Genes upregulated at least 2-fold in human stem cell rescued retinas

| | (raw data) | | | | | p-value, call (A=absent, P=present) | | |
|---|---|---|---|---|---|---|---|---|
| Common Name | MR | HR | HNR | Genbank | Keywords | Lin (-) | CD31 (-) | NI rd/rd |
| EST | 397 | 1885 | 489 | AK024177 | EST | 0.024 | 0.007 | 0.006 |
| CD6 | 966 | 2854 | 840 | NM_006725 | CD6 antigen | 0.011 | 0.065 | <0.001 |
| IFNα13 | 241 | 606 | 220 | NM_006900 | interferon, alpha 13 | 0.010 | 0.063 | 0.013 |
| TRAG3 | 269 | 615 | 229 | NM_004909 | taxol resistance associated gene 3 | 0.028 | 0.052 | 0.001 |
| ELA2 | 229 | 545 | 187 | NM_001972 | elastase 2, neutrophil | 0.003 | 0.070 | 0.013 |
| PP32D | 179 | 411 | 146 | NM_012404 | acidic nuclear phosphoprotein 32D | 0.003 | 0.067 | 0.002 |
| otoferlin | 232 | 527 | 239 | NM_004802 | otoferlin | 0.002 | 0.050 | 0.008 |
| acyl oxidase | 175 | 391 | 164 | NM_004035 | acyl-Coenzyme A oxidase | <0.001 | 0.064 | 0.001 |
| HS6ST1 | 204 | 455 | 210 | NM_004807 | heparan sulfate sulfotransferase | 0.010 | 0.063 | 0.004 |
| ACCN3 | 187 | 413 | 181 | NM_004769 | amiloride-sensitive cation channel | 0.007 | 0.070 | 0.002 |

(D) Neurotrophic or growth factor genes upregulated in human HSC rescued retinas

| | (raw data) | | | | | p-value, call (A=absent, P=present) | | |
|---|---|---|---|---|---|---|---|---|
| Common Name | MR | HR | HNR | Genbank | Keywords | Lin (-) | CD31 (-) | NI rd/rd |
| IGF2 | 743 | 1382 | 839 | NM_016412 | insulin-like growth factor 2 | <0.001 | 0.041 | 0.007 |
| SCGF | 474 | 547 | 402 | NM_002975 | stem cell growth factor | 0.003 | 0.002 | 0.009 |
| TGF, beta1 | 841 | 1012 | 819 | NM_000660 | transforming growth factor beta 1 | 0.003 | 0.005 | 0.002 |
| TGF, beta1 | 144 | 252 | 122 | NM_000660 | (2nd probe along TGF-β mRNA) | 0.006 | 0.059 | 0.017 |
| EGFR S8 | 499 | 593 | 491 | AI343292 | EGF receptor pathway substrate 8-related protein 1 | 0.010 | 0.006 | 0.008 |
| FGF-6 | 524 | 613 | 526 | NM_020996 | fibroblast growth factor 6 | 0.004 | 0.010 | 0.005 |
| EST (IGFBP?) | 927 | 991 | 895 | AW338791 | similarities to IGF binding proteins | 0.006 | 0.006 | 0.003 |
| FGF-12 | 471 | 523 | 507 | AL119322 | fibroblast growth factor 12 | 0.006 | 0.001 | <0.001 |
| EGF-like | 991 | 1092 | 1088 | M60278 | diptheria toxin receptor, EGF-like | 0.004 | 0.004 | 0.003 |
| FGF-21 | 592 | 615 | 590 | NM_019113 | fibroblast growth factor 21 | 0.005 | 0.001 | 0.004 |

Post natal development of retinal vasculature in wild type C57/B16 mice raised in normoxia.

Rescue effect of Lin-HSC in OIR model. CD31-CD34-CD11b-HSC (left panels, "Cntrl") or Lin-HSC (right panels) were injected intravitreally on P3 into the left or right eyes, respectively, in the same animal. On P7 the animal was placed into 75% oxygen for 5 days, normoxia on P12 and analyzed by confocal microscopy on P17. Red is lectin and blue is DAPI staining.

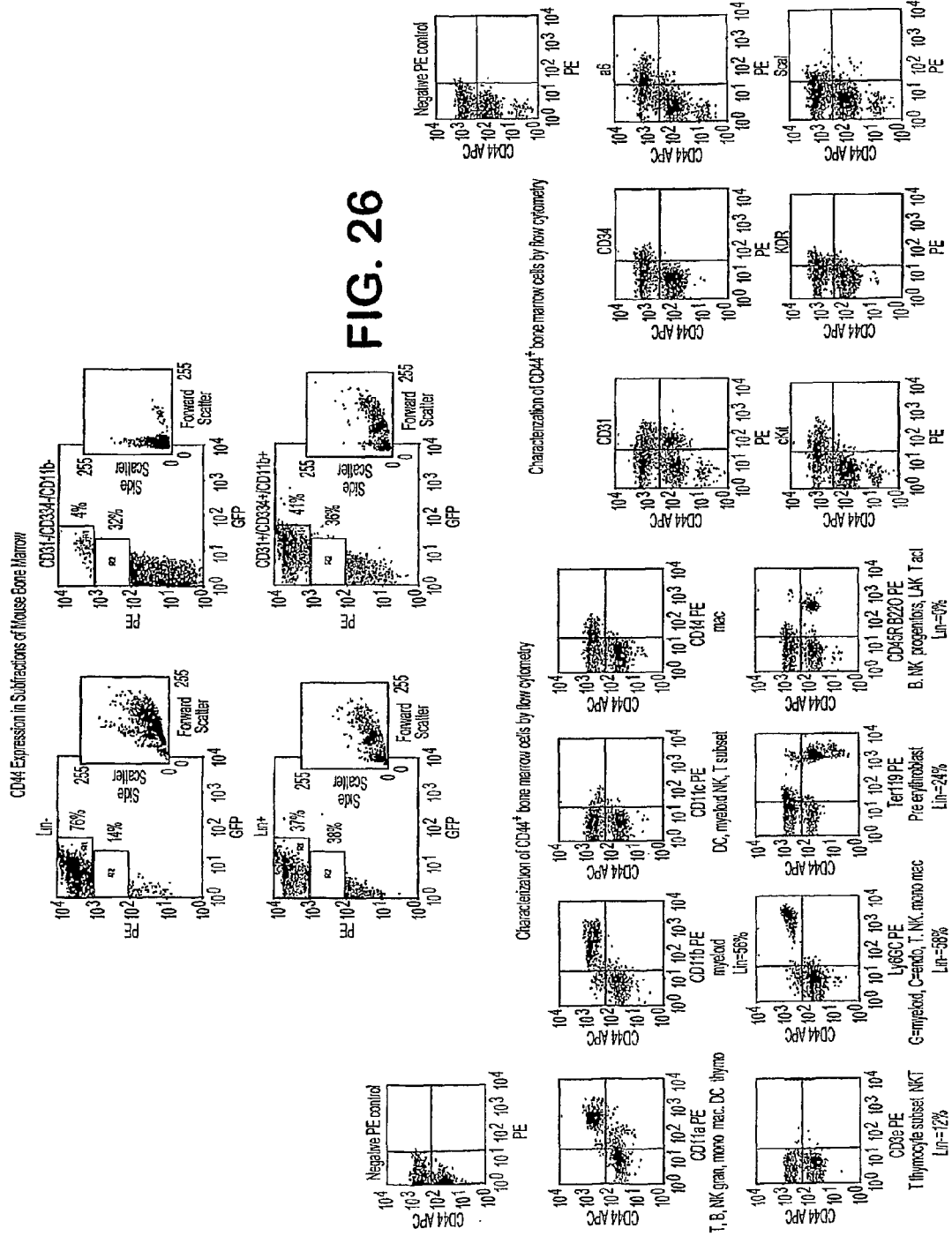

CD44hi injected P7 (11-29-04)
Day 14 (12-13-04)
eGFP, Collgen IV
CD44lo injected P3 (11-15-04)
Day 7 (11-22-04)
eGFP, Lectin
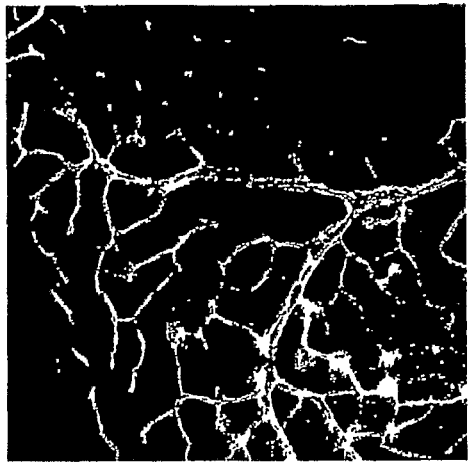
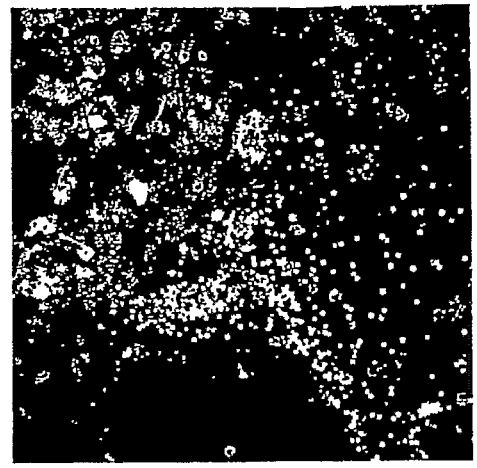
FIG. 28
rd1 (C3H) injected P8 12-01-04 analyzed P27 12-20-04
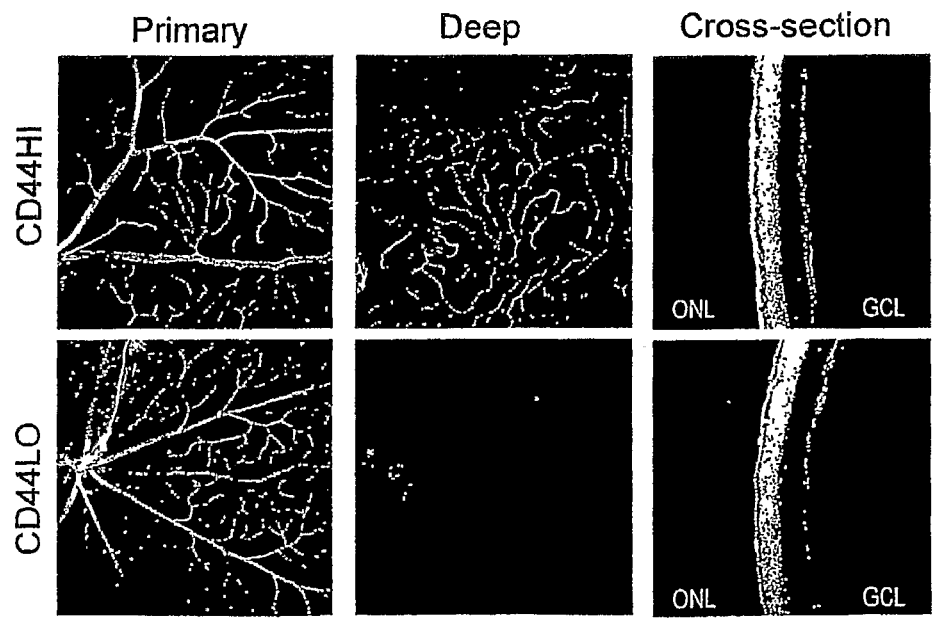
FIG. 29

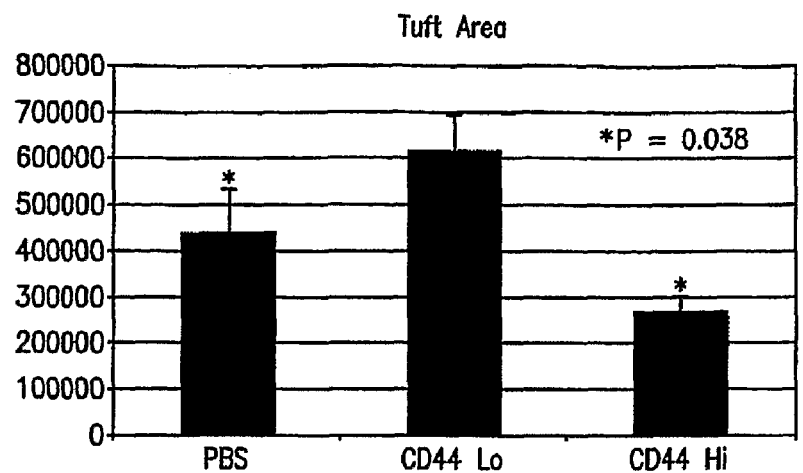
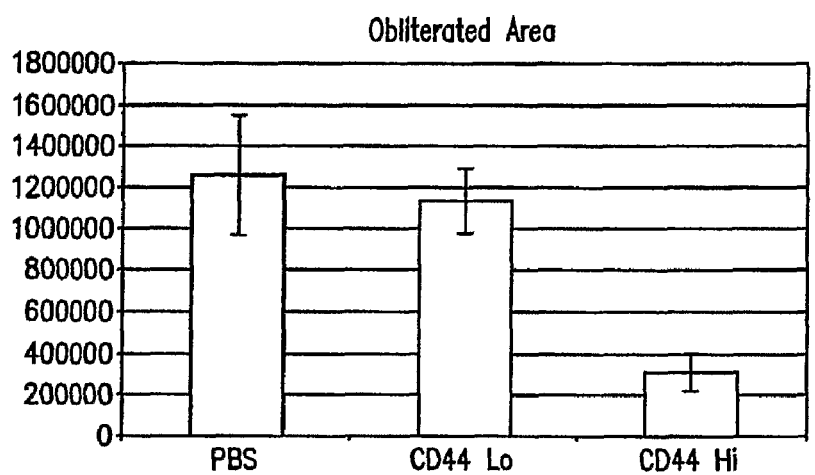
FIG. 30
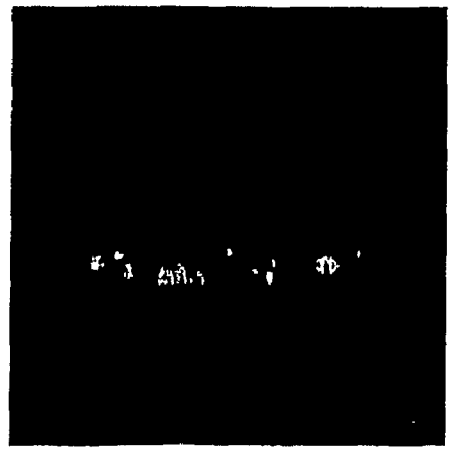
FIG. 31

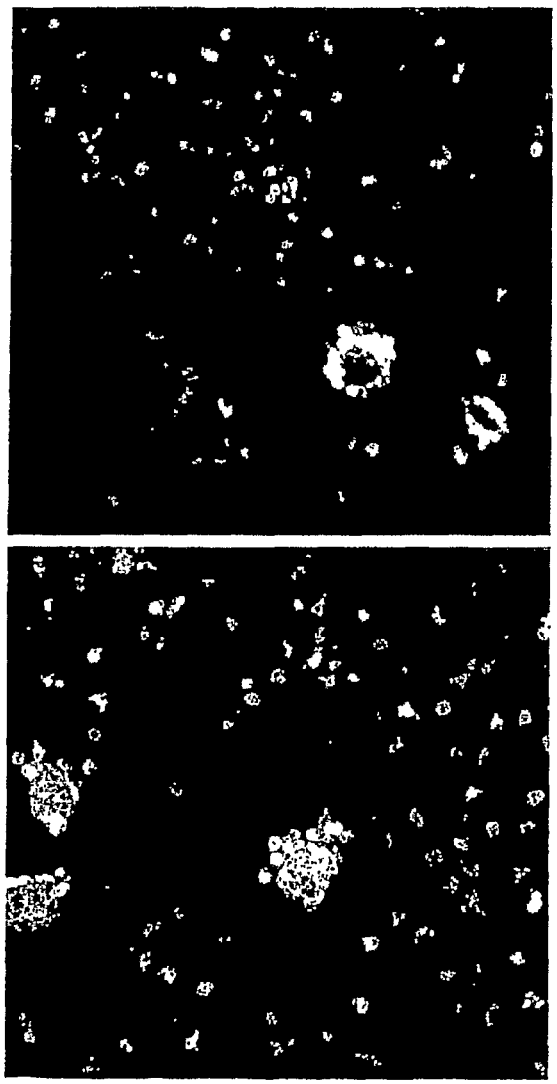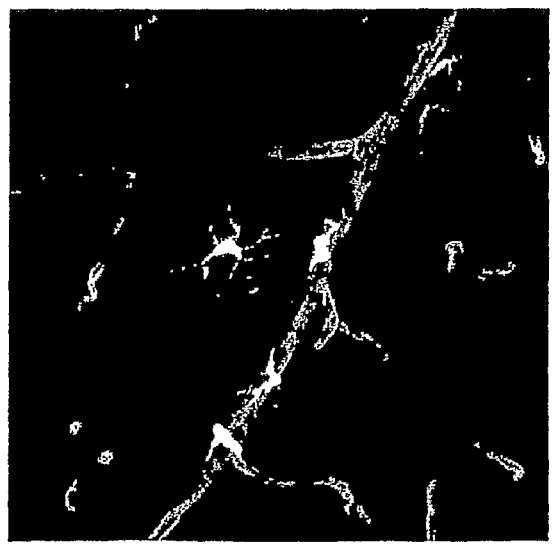
CD11b- Bone Marrow Cells, Injected P2, 20 days Post-injection
FIG. 33

T2 TrpRS (SEQ ID NO: 3)

SAKGIDYDKLIVRFGSSKIDKELINRIERATGQRPHHFLRRGIFFSHRDMNQVLDAYEN
KKPFYLYTGRGPSSEAMHVGHLIPFIFTKWLQDVFNVPLVIQMTDDEKYLWKDLTLDQA
YSYAVENAKDIIACGFDINKTFIFSDLDYMGMSSGFYKNVVKIQKHVTFNQVKGIFGFT
DSDCIGKISFPAIQAAPSFSNSFPQIFRDRTDIQCLIPCAIDQDPYFRMTRDVAPRIGY
PKPALLHSTFFPALQGAQTKMSASDPNSSIFLTDTAKQIKTKVNKHAFSGGRDTIEEHR
QFGGNCDVDVSFMYLTFFLEDDDKLEQIRKDYTSGAMLTGELKKALIEVLQPLIAEHQA
RRKEVTDEIVKEFMTPRKLSFDFQ

T2 TrpRS-GD (SEQ ID NO: 4)

SAKGIDYDKLIVRFGSSKIDKELINRIERATGQRPHHFLRRGIFFSHRDMNQVLDAYEN
KKPFYLYTGRGPSSEAMHVGHLIPFIFTKWLQDVFNVPLVIQMTDDEKYLWKDLTLDQA
YGDAVENAKDIIACGFDINKTFIFSDLDYMGMSSGFYKNVVKIQKHVTFNQVKGIFGFT
DSDCIGKISFPAIQAAPSFSNSFPQIFRDRTDIQCLIPCAIDQDPYFRMTRDVAPRIGY
PKPALLHSTFFPALQGAQTKMSASDPNSSIFLTDTAKQIKTKVNKHAFSGGRDTIEEHR
QFGGNCDVDVSFMYLTFFLEDDDKLEQIRKDYTSGAMLTGELKKALIEVLQPLIAEHQA
RRKEVTDEIVKEFMTPRKLSFDFQ

FIG. 34

Mini TrpRS (SEQ ID NO: 5)

SYKAAAGEDYKADCPPGNPAPTSNHGPDATEAEEDFVDPWTVQTSSAKGIDYDKLIVRF
GSSKIDKELINRIERATGQRPHHFLRRGIFFSHRDMNQVLDAYENKKPFYLYTGRGPSS
EAMHVGHLIPFIFTKWLQDVENVPLVIQMTDDEKYLWKDLTLDQAYSYAVENAKDIIAC
GFDINKTFIFSDLDYMGMSSGFYKNVKIQKHVTFNQVKGIFGFTDSDCIGKISFPAIQ
AAPSFSNSFPQIFRDRTDIQCLIPCAIDQDPYFRMTRDVAPRIGYPKPALLHSTFFPAL
QGAQTKMSASDPNSSIFLTDTTAKQIKTKVNKHAFSGGRDTIEEHRQFGGNCDVDSFMY
LTFFLEDDDKLEQIRKDYTSGAMLTGELKKALIEVLQPLIAEHQARRKEVTDEIVKEFM
TPRKLSFDFQ

FIG. 35

T1-TrpRS (SEQ ID NO: 6)

SNHGPDATEAEEDFVDPWTVQTSSAKGIDYDKLIVRFGSSKIDKELINRIERATGQRPH
HFLRRGIFFSHRDMNQVLDAYENKKPFYLYTGRGPSSEAMHVGHLIPFIFTKWLQDVEN
VPLVIQMTDDEKYLWKDLTLDQAYSYAVENAKDIIACGFDINKTFIFSDLDYMGMSSGF
YKNVVKIQKHVTFNQVKGIFGFTDSDCIGKISFPAIQAAPSFSNSFPQIFRDRTDIQCL
IPCAIDQDPYFRMTRDVAPRIGYPKPALLHSTFFPALQGAQTKMSASDPNSSIFLTDTA
KQIKTKVNKHAFSGGRDTIEEHRQFGGNCDVDSFMYLTFFLEDDKLEQIRKDYTSGA
MLTGELKKALIEVLQPLIAEHQARRKEVTDEIVKEFMTPRKLSFDFQ

FIG. 36

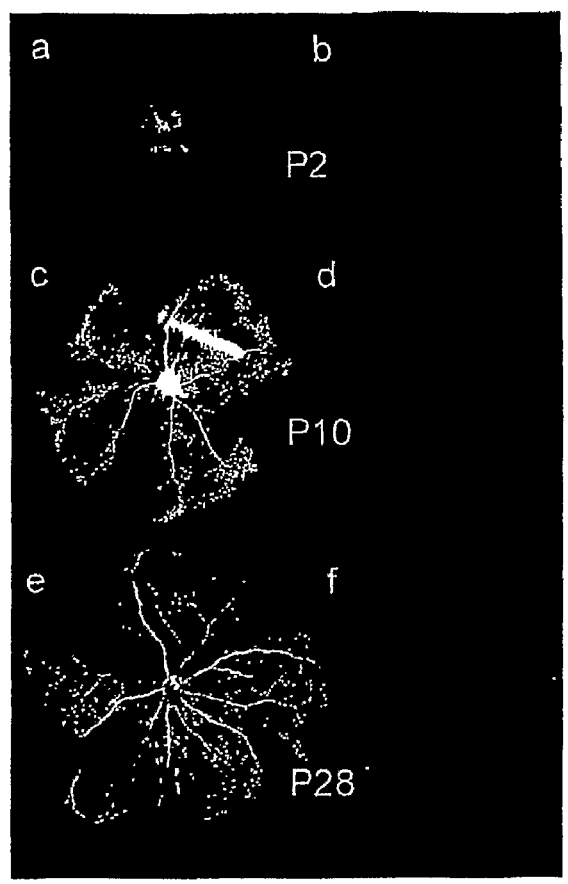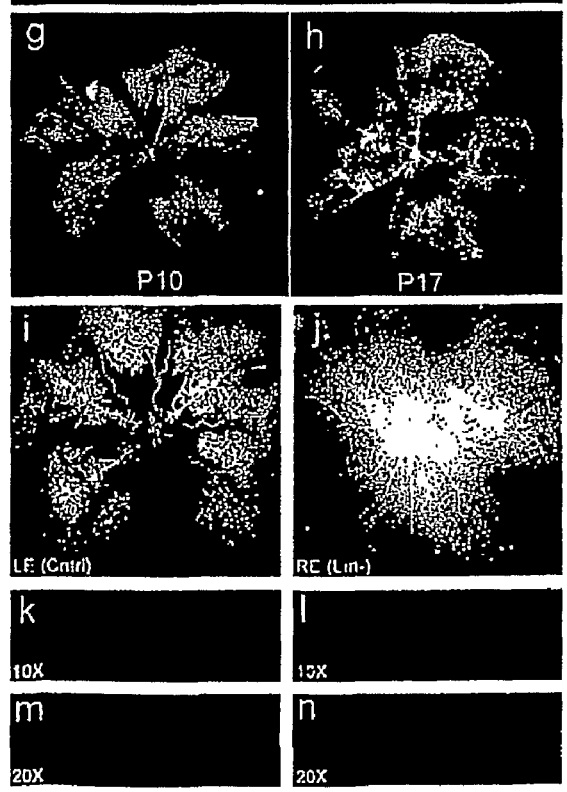
FIG. 37

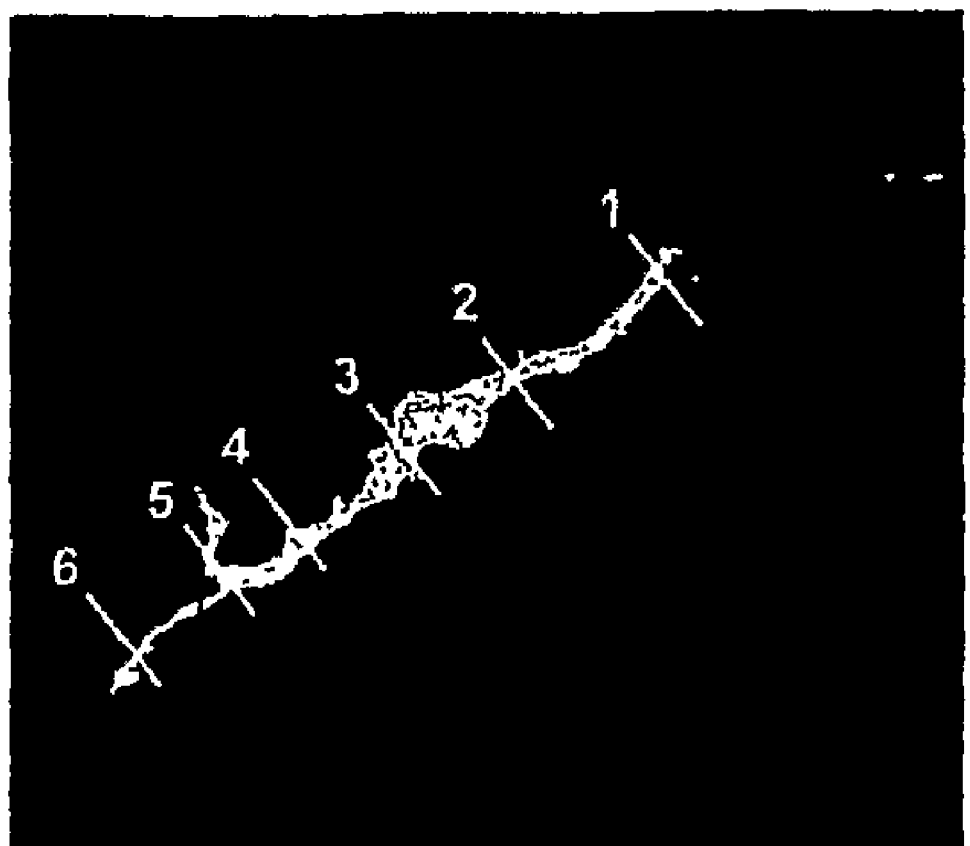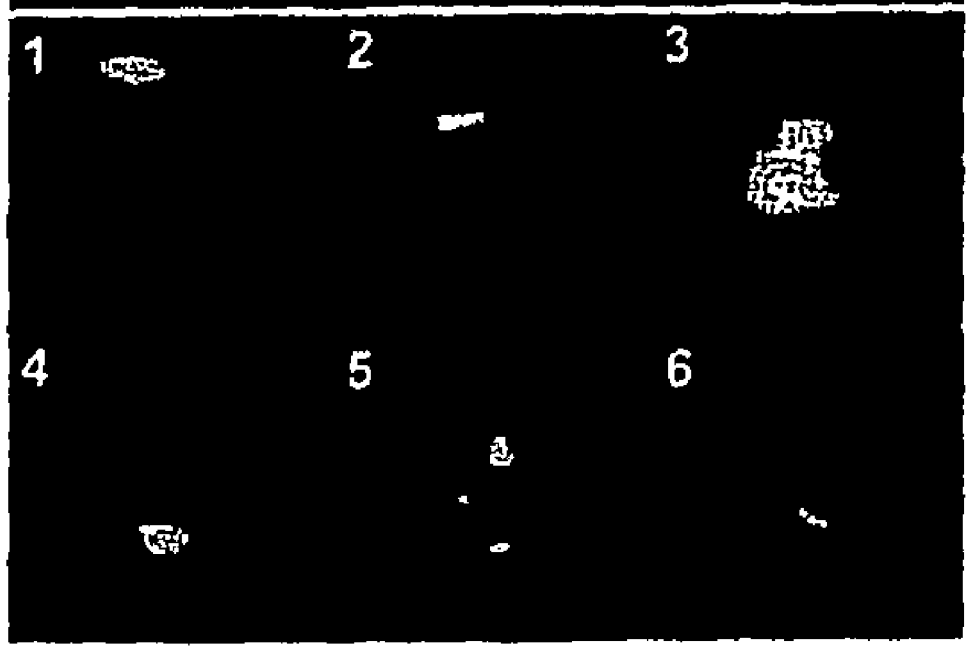
FIG. 42

Genes expressed higher in CD44hi BM cells

|       | CD44hi | CD44low | hi/lo | Genbank ID | expressed by: |
|-------|--------|---------|-------|------------|---------------|
| CD204 | 117.5  | 0.4     | 293.8 | BC003814   | macro |
| CD114 | 1079.5 | 12.2    | 88.5  | NM_007782  | neutrophils, granulocytes |
| CD33  | 2006.3 | 23.2    | 86.5  | NM_021293  | myeloid progenitors |
| CD115 | 2412.3 | 72.6    | 33.2  | AI323359   | monocytic progenitors |
| CD34  | 956.5  | 74.9    | 12.8  | NM_133654  | hematopoietic precursors, ECs, BM stroma, mast cells |
| CD9   | 1072.7 | 115.8   | 9.3   | NM_007657  | myeloid cells, activated T, subset of B |
| CD68  | 783.6  | 101.1   | 7.8   | BC021637   | tissue macro and DCs |
| CD4   | 126.8  | 18.1    | 7.0   | NM_013488  | DC, subset of thymocytes and T |
| CD80  | 92.8   | 17.2    | 5.4   | AA596883   | mono, macro, DCs, activated T and B |
| CD44  | 3497.9 | 679.6   | 5.1   | AW146109   | broad expression |

Genes expressed higher in CD44lo BM cells

|       | CD44hi | CD44lo | lo/hi | Genbank ID | expressed by: |
|-------|--------|--------|-------|------------|---------------|
| CD19  | 9.5    | 4268.3 | 449.3 | NM_009844  | B, follicular DCs |
| CD79a | 14.1   | 5380.2 | 381.6 | NM_007655  | B |
| CD22  | 50 7   | 4114.5 | 81.2  | NM_009845  | B |
| CD2   | 28 6   | 2131.7 | 74.5  | NM_013486  | thymocytes, T, NK, B, myeloid cells, erythro |
| CD72  | 109.7  | 4688.9 | 42.7  | BC003824   | B, follicular DCs, subset of T |
| CD22  | 8.0    | 249.4  | 31.2  | AF102134   | B |
| CD79b | 254.5  | 7414.6 | 29.1  | NM_008339  | B |
| CD1d2 | 5.1    | 114.1  | 22.4  | NM_007640  | leukocytes |
| CD83  | 138.8  | 2262.7 | 16.3  | NM_009856  | DCs, activated T |
| CD38  | 293.2  | 3917.3 | 13.4  | BB256012   | B, activated T, subset of thymocytes, |
| CD1d1 | 123.6  | 1228.9 | 9.9   | NM_007639  | leukocytes |
| CD36  | 11.5   | 107 8  | 9.4   | AK004192   | platelets, adipocytes, mono, macro, ECs, erythro |
| CD160 | 7.8    | 70.3   | 9.0   | AU045688   | T, NK |
| CD3e  | 151.6  | 1222.5 | 8.1   | NM_007648  | T, subset of thymocytes, NKT |

FIG. 44

ISOLATED MYELOID-LIKE BONE MARROW CELL POPULATIONS AND METHODS OF TREATMENT THEREWITH

CROSS-REFERENCE TO RELATED APPLICATIONS

This application is the national stage of International Application No. PCT/US2006/006411, filed on Feb. 24, 2006, which claims the benefit of U.S. Provisional Patent Application No. 60/656,037, filed on Feb. 24, 2005, each of which is incorporated herein by reference.

STATEMENT OF GOVERNMENT INTEREST

A portion of the work described herein was supported by grant numbers EY 11254, EY 12598, and EY 13916 from the National Institutes of Health. The United States Government has certain rights in this invention.

FIELD OF THE INVENTION

This invention relates to isolated, mammalian, bone marrow cells. More particularly the invention is related to isolated bone marrow cell populations that have myeloid cell characteristics and are capable of being incorporated into retinal vasculature when intravitreally injected into the eye. The invention also relates to methods of treating ocular degenerative diseases by administering isolated bone marrow cells to the eye of a mammal.

BACKGROUND OF THE INVENTION

Age related macular degeneration (ARMD) and diabetic retinopathy (DR) are the leading causes of visual loss in industrialized nations and do so as a result of abnormal retinal neovascularization. Since the retina consists of well-defined layers of neuronal, glial, and vascular elements, relatively small disturbances such as those seen in vascular proliferation or edema can lead to significant loss of visual function. Inherited retinal degenerations, such as retinitis pigmentosa (RP), are also associated with vascular abnormalities, such as arteriolar narrowing and vascular atrophy. Most inherited human retinal degenerations specifically affect rod photoreceptors, but there is also a concomitant loss of cones, the principal cellular component of the macula, the region of the retina in humans that is responsible for central, fine visual acuity. Cone-specific survival factors have been described recently (Mohand-Said et al. 1998, *Proc. Natl. Acad. Sci. USA*, 95: 8357-8362) and may facilitate cone survival in mouse models of retinal degeneration.

Inherited degenerations of the retina affect as many as 1 in 3500 individuals and are characterized by progressive night blindness, visual field loss, optic nerve atrophy, arteriolar attenuation, altered vascular permeability and central loss of vision often progressing to complete blindness (Heckenlively, J. R., editor, 1988; *Retinitis Pigmentosa*, Philadelphia: JB Lippincott Co.). Molecular genetic analysis of these diseases has identified mutations in over 110 different genes accounting for only a relatively small percentage of the known affected individuals (Humphries et al., 1992, *Science* 256:804-808; Farrar et al 2002, *EMBO J.* 21:857-864.). Many of these mutations are associated with enzymatic and structural components of the phototransduction machinery including rhodopsin, cGMP phosphodiesterase, rds peripherin, and RPE65. Despite these observations, there are still no effective treatments to slow or reverse the progression of these retinal degenerative diseases. Recent advances in gene therapy have led to successful reversal of the rds (Ali et al. 2000, *Nat. Genet.* 25:306-310) and rd (Takahashi et al. 1999, *J. Virol.* 73:7812-7816) phenotypes in mice and the RPE65 phenotype in dogs (Acland et al. 2001, *Nat. Genet.* 28:92-95) when the wild type transgene is delivered to photoreceptors or the retinal pigmented epithelium (RPE) in animals with a specific mutation.

For many years it has been known that a population of stem cells exists in the normal adult circulation and bone marrow. Different sub-populations of these cells can differentiate along hematopoietic lineage positive (Lin$^+$) or lineage negative (Lin$^-$) lineages. Furthermore, the lineage negative hematopoietic stem cell (HSC) population has recently been shown to contain endothelial progenitor cells (EPC) capable of forming blood vessels in vitro and in vivo (See Asahara et al. 1997, *Science* 275: 964-7). These cells can participate in normal and pathological postnatal angiogenesis (See Lyden et al. 2001 *Nat. Med.* 7, 1194-201; Kalka et al. 2000, *Proc. Natl. Acad. Sci. U.S.A.* 97:3422-7; and Kocher et al. 2001, *Nat. Med.* 7: 430-6) as well as differentiate into a variety of non-endothelial cell types including hepatocytes (See Lagasse et al. 2000, *Nat. Med.* 6:1229-34), microglia (See Priller et al. 2002 *Nat. Med.* 7:1356-61), cardiomyocytes (See Orlic et al. 2001, *Proc. Natl. Acad. Sci. U.S.A.* 98:10344-9) and epithelium (See Lyden et al. 2001, *Nat. Med.* 7:1194-1201). Although these cells have been used in several experimental models of angiogenesis, the mechanism of EPC targeting to neovasculature is not known, and no strategy has been identified that will effectively increase the number of cells that contribute to a particular vasculature.

Hematopoietic stem cells from bone marrow are currently the only type of stem cell commonly used for therapeutic applications. Bone marrow HSC's have been used in transplants for over 40 years. Currently, advanced methods of harvesting purified stem cells are being investigated to develop therapies for treatment of leukemia, lymphoma, and inherited blood disorders. Clinical applications of stem cells in humans have been investigated for the treatment of diabetes and advanced kidney cancer in limited numbers of human patients.

SUMMARY OF THE INVENTION

The present invention provides an isolated myeloid-like bone marrow (MLBM) cell population produced by positively selecting cells that express CD44, CD11b, or both antigens, from bone marrow of a mammal. These cells exhibit beneficial vasculotrophic and neurotrophic activity when intraocularly administered to the eye of a mammal, particularly a mammal suffering from an ocular degenerative disease. The MLBM cell population of the invention can be isolated by treating bone marrow cells with an antibody against CD44 (hyaluronic acid receptor), an antibody against CD11b, or antibodies against both antigens, and positively selecting cells that immunoreact with the antibody or antibodies, as the case may be (e.g., using flow cytometry or antibody-coated or bound beads to separate the cells). A majority of the cells of the MLBM cell population of the invention are lineage negative and express both the CD44 antigen and the CD11b antigen.

The present invention also provides a method of treating vasculotrophic and neurotrophic retinal diseases in a mammal. The method comprises administering isolated cells from the MLBM cell population to the diseased eye of a mammal, preferably by intraocular injection. Preferably, the MLBM cell population is autologous to the mammal being treated (i.e., the MLBM cell population was isolated from the bone marrow of the individual mammal to be treated). The present treatment method ameliorates vascular degeneration and degeneration of photoreceptor neurons in the retina of a mammal that suffers from an ocular disease. The cells are administered in an amount sufficient to retard vascular and neural degeneration in the retina. Beneficially, the cells from the MLBM cell population incorporate into the vasculature of the retina and differentiate into endothelial cells, while at the same time incorporating into the neuronal network and ameliorating the degeneration of cone cells in the retina. The isolated, mammalian, MLBM cell population, includes cells that selectively target activated retinal astrocytes when intravitreally injected into the eye, and remain stably incorporated into neovasculature and neuronal network of the eye. Preferably the mammal is a human.

In a preferred embodiment, at least about 75 percent of the cells in the isolated myeloid-like bone marrow cell population express CD44, more preferably at least about 90 percent.

In one preferred embodiment, cells from the MLBM cell population are transfected with a therapeutically useful gene. For example, the cells can be transfected with polynucleotides that operably encode for neurotrophic agents or anti-angiogenic agents that selectively target neovasculature and inhibit new vessel formation without affecting already established vessels through a form of cell-based gene therapy. In one embodiment, isolated, MLBM cell population of the invention include a gene encoding an angiogenesis inhibiting peptide. The angiogenesis inhibiting cells from the MLBM cell population are useful for modulating abnormal blood vessel growth in diseases such as ARMD, DR and certain retinal degenerations associated with abnormal vasculature. In another preferred embodiment, the isolated, cells from the MLBM cell population of the present invention are transfected to include a gene encoding a neurotrophic peptide. The neurotrophic transfected MLBM cells are useful for promoting neuronal rescue in ocular diseases involving retinal neural degeneration, such as glaucoma, retinitis pigmentosa, and the like.

A particular advantage of ocular treatments with the isolated MLBM cell population of the present invention is a vasculotrophic and neurotrophic rescue effect observed in eyes intravitreally treated with cells from the MLBM cell population. Retinal neurons and photoreceptors, particularly cones, are preserved and some measure of visual function can be maintained in eyes treated with cells from the MLBM cell population of the invention.

The present invention also provides a method for isolating a myeloid-like bone marrow cell population from bone marrow by negative cell marker selection. The method comprises contacting a plurality of bone marrow cells with antibodies specific for Ter119, CD45RB220, and CD3e, removing cells from the plurality of bone marrow cells that immunoreact with Ter119, CD45RB220, and CD3e antibodies, and recovering myeloid-like bone marrow cells that are deleted in Ter119, CD45RB220, and CD3e-expressing cells. Using this method, a cell population can be recovered in which greater than 90 percent of the cells express CD44.

Preferably, the diseased retina to be treated by the MLBM cell population and methods of the invention includes activated astrocytes. This can be accomplished by early treatment of the eye when there is an associated gliosis, or by using a laser to stimulate local proliferation of activated astrocytes.

In addition to therapeutic uses, the isolated myeloid-like bone marrow cell populations of the invention are useful as research tools to investigate the physiology of vascular development in the eye, and to deliver specific genes to specific locations (e.g., astrocytes) within the eye. Such uses provide a valuable tool for investigation of gene function and potential therapeutic mechanisms.

BRIEF DESCRIPTION OF THE DRAWINGS

In the DRAWINGS:

FIG. 7 shows the DNA sequence encoding $His_6$-tagged T2-TrpRS, SEQ ID NO: 1.

FIG. 8 shows the amino acid sequence of $His_6$-tagged T2-TrpRS, SEQ ID NO: 2.

FIG. 20 includes tables of genes that are upregulated in murine retinas that have been treated with the Lin⁻HSCs of the present invention. (A) Genes whose expression is increased 3-fold in mouse retinas treated with murine Lin⁻ HSCs. (B) Crystallin genes that are upregulated in mouse retinas treated with murine Lin⁻HSC. (C) Genes whose expression is increased 2-fold in mouse retinas treated with human Lin⁻HSCs. (D) Genes for neurotrophic factors or growth factors whose expression is upregulated in mouse retinas treated with human Lin⁻HSCs.

FIG. 26 shows scatter plots from flow cytometry characterization of lineage negative and lineage positive stem cell populations (upper left and lower left plots, respectively) showing percentages of cells that express the CD44 antigen (data points in red); as well as plots of CD31 negative and CD31 positive cell populations (upper right and lower right plots, respectively), showing percentages of cells that express the CD44 antigen (data points in red).

FIG. 27 shows scatter plots from flow cytometry characterization of a lineage negative cell population that expresses a significant level of CD44 antigen (left set of plots) and a sub-population of bone marrow cells that do not express a significant level of CD44 antigen (right set of plots) illustrating the relative percentages of cells expressing various other cell surface antigens.

FIG. 28 shows photomicrographic images of a retina from a mouse intravitreally injected with cells from the MLBM cell population of the invention (left panel) compared to a retina from a mouse intravitreally injected with CD44$^{lo}$ cells.

FIG. 29 shows photomicrographic images of retinas from eyes injected with cells from the MLBM cell population (CD44$^{hi}$) and with CD44$^{lo}$ cells.

FIG. 30 shows bar graphs demonstrating the beneficial effects of the MLBM cell population for ameliorating pathogenic angiogensis and promoting beneficial physiological revascularization of mouse retinas in the oxygen induced retinopathy model of retinopathy of prematurity. The upper graph compares pre-retinal neovascular tuft area for control retina (first bar), retina treated with CD44$^{lo}$ cells (middle bar) and retinas treated with cells from the MLBM cell population (right bar). The lower graph compares vascular obliteration area for control retina (first bar), retina treated with CD44$^{lo}$ cells (middle bar) and retinas treated with cells from the MLBM cell population (right bar).

FIG. 31 is a photomicrographic image demonstrating that once cells from the MLBM cell population have incorporated into the vasculature of the retina, the cells express vascular endothelial growth factor (VEGF), as indicated by the green staining of the cells in the lower portion of the image.

FIG. 33 depicts photomicrographic images demonstrating that CD44⁻ CD11b⁻bone marrow cells do not selectively target the vasculature of the retina.

FIG. 34 shows the amino acid residue sequence of the T2 fragment of TrpRS (SEQ ID NO: 3) and of the T2-TrpRS-GD variation thereof (SEQ ID NO: 4).

FIG. 35 shows the amino acid residue sequence of mini-TrpRS (SEQ ID NO: 5).

FIG. 36 shows the amino acid residue sequence of T1-TrpRS (SEQ ID NO: 6).

FIG. 37 shows normal retinal vascular development in the mouse, the oxygen-induced retinopathy (OIR) model, and the rescue effect following intra-vitreal transplantation of Lin-bone-marrow derived-cells. The mouse is born with a largely avascular retina. as shown at postnatal day 2 (P2) (Panel a, retinal whole-mount) where the vessels are found in the superficial retina occupying a single plane as shown in b. Panels b,d and f are images taken from 3D renderings of en face confocal z-series data sets rotated 90 degrees. During the first week after birth, the superficial retinal vasculature grows in a radial fashion from the optic nerve head nearly reaching the periphery by P10 (c). The deep retinal vasculature is then established from branching of the superficial layer during the second week (d). Finally, a third plexus of vessels forms between the first two, and establishes the mature retinal vasculature at around P30 (e,f). Panel g shows that exposure to hyperoxia in the OIR model causes central vaso-obliteration as shown here at P10. Panel h shows that after removal to normoxia at P12, the central retina starts to revascularize and characteristic pre-retinal neovascular tufts are formed at the interface between the vascularized (peripheral) and avascular (central) retina. These tufts stain strongly with isolectin. Panels i-n show that Lin⁻ hematopoietic progenitor cells promote vascular repair in the OIR model. Lin⁻ cells injected intravitreally prior to high oxygen exposure dramatically accelerate revascularization of the central retina when compared to the vehicle-treated fellow eye at P17. While retinas treated with vehicle show partial absence of the superficial vasculature (i) and complete absence of the deep retinal vasculature (k,m), the Lin⁻ cell-treated fellow eye shows relatively normal retinal vasculature (j) with all three plexuses present (k,m). Panel o shows that at P17, OIR eyes treated with Lin⁻ cells are fully revascularized significantly more often than uninjected eyes or those injected with vehicle. Vessels were visualized by cardiac perfusion of fluorescein-dextran, as shown in Panels a-f,i,j and by GS lectin in Panels g,h,k-n. Nuclei in Panels k-n were labeled with DAPI.

FIG. 42 shows that $CD44^{HI}$ cells take on a perivascular localization in the retina. Confocal imaging was used to create a series of images in the z dimension which were then rendered into 3D. In Panel a, a projection of this is shown the CD31-labeled vascular endothelium and GFP expression from the introduced bone marrow cells are shown. The bone marrow cell appears to have assumed a perivascular position. 3D data show that the lumen of the vessel and the relative position of the GFP⁺ bone marrow cell are visualized. The numbers listed in (b) correspond to cross-sectional positions indicated in (a). The GFP signal was detected outside of the lumen in all cases, except Panel b, No. 3, which was a section through the cell body with intense fluorescence where bleed-through of the signal was evident.

FIG. 44 shows an expression array analysis, which revealed a high expression of myeloid-associated genes in the $CD44^{HI}$ population while the $CD44^{LO}$ cells expressed genes associated with lymphoid cells. AFFYMETRIX® arrays were used to compare gene expression profiles between these two bone marrow cell populations. Genes shown had a minimum 5-fold difference in expression. A significantly higher level of CD44 expression in the $CD44^{HI}$ population was observed versus $CD44^{LO}$ cells.

DETAILED DESCRIPTION OF PREFERRED EMBODIMENTS

Figure 1:
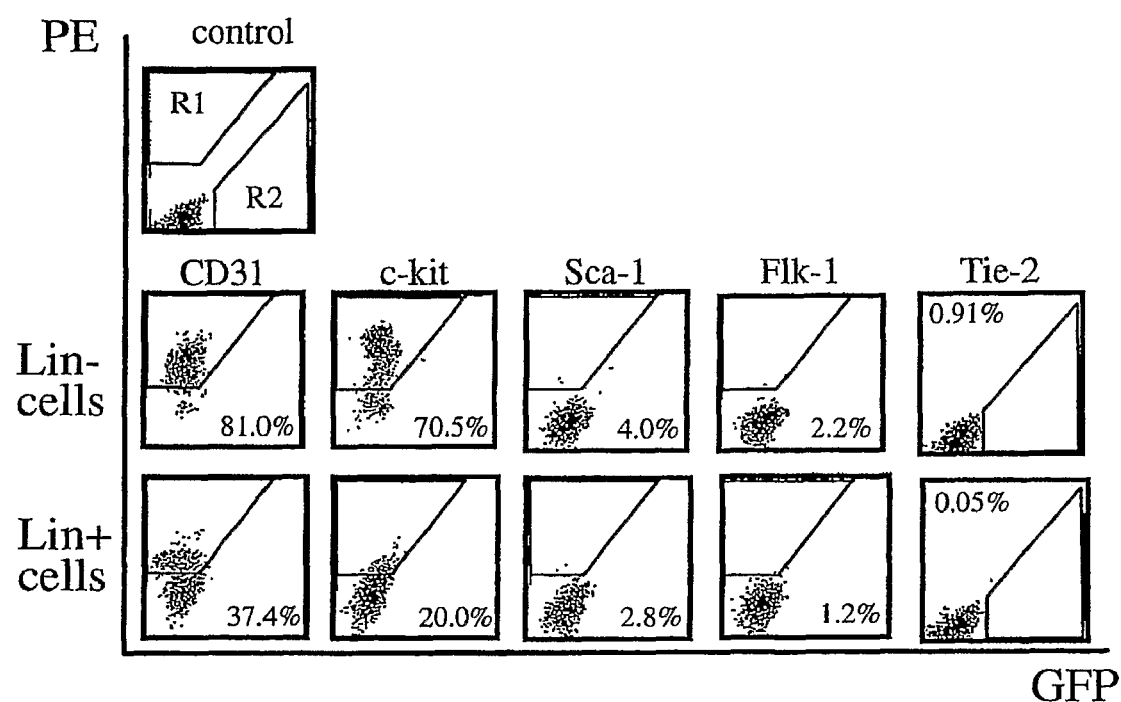
FIG. 1 depicts schematic diagrams of developing mouse retina. (a) Development of primary plexus. (b) The second phase of retinal vessel formation. GCL, ganglion cell layer; IPL, inner plexus layer; INL, inner nuclear layer; OPL, outer plexus layer; ONL, outer nuclear layer; RPE, retinal pigment epithelium; ON, optic nerve; P, periphery. Panel (c) depicts flow cytometric characterization of bone marrow-derived Lin$^+$ HSC and Lin$^-$ HSC separated cells. Top row: Dot plot distribution of non-antibody labeled cells, in which R1 defines the quantifiable-gated area of positive PE-staining; R2 indicates GFP-positive; Middle row: Lin$^-$ HSC (C57B/6) and Bottom row: Lin$^+$ HSC (C57B/6) cells, each cell line labeled with the PE-conjugated antibodies for Sca-1, c-kit, Flk-1/KDR, CD31. Tie-2 data was obtained from Tie-2-GFP mice. Percentages indicate percent of positive-labeled cells out of total Lin$^-$HSC or Lin$^+$ HSC population.

Bone marrow cells include a sub-population of cells that express the CD44 antigen (i.e., the hyaluronic acid receptor) and CD11b (integrin αM). A myeloid-like population of bone marrow cells enriched in CD44 and CD11b expressing cells can be isolated from bone marrow by treating bone marrow cells with an antibody to CD44 antigen (anti-CD44) and/or an antibody to CD11b antigen (anti-CD11b), and then selecting cells that immunoreact with the antibody. The antibody then can be removed from the cells by methods that are well known in the art. The cells can be selected, for example, using by flow cytometry, using antibodies bound to or coated on beads followed by filtration, or other separation methods that are well known in the art. A majority of the selected cells are lineage negative and express both the CD44 antigen and the CD11b antigen, regardless of which antibody is utilized in the isolation.

Bone marrow includes stem cells. Stem cells are typically identified by the distribution of antigens on the surface of the cells (for a detailed discussion see *Stem Cells: Scientific Progress and Future Directions*, a report prepared by the National Institutes of Health, Office of Science Policy, June 2001, Appendix E: Stem Cell Markers, which is incorporated herein by reference to the extent pertinent). Approximately 75% of lineage negative hematopoietic stems cells isolated from bone marrow are also CD44 positive. In a preferred embodiment, a majority of the cells from the MLBM cell population are lineage negative hematopoietic stem cells (i.e., $CD44^+Lin^-HSC$).

The present invention provides a method of ameliorating vascular and neuronal degeneration in the retina of a mammal that suffers from an ocular disease. Isolated MLBM cell population of the invention is administered to the retina of the mammal, preferably by intravitreal injection. The cells are administered in an amount sufficient to ameliorate vascular and/or neuronal degeneration in the retina. Preferably, the isolated MLBM cell population is autologous to the mammal to be treated. Preferably, the cells from the MLBM cell population are administered in a physiologically tolerable medium, such as phosphate buffered saline (PBS).

A preferred method comprises isolating the MLBM cell population from the bone marrow of the mammal to be treated and then administering the cells to the mammal in a number sufficient to ameliorate the vascular and/or neuronal degeneration of the retina. The cells can be isolated from a mammal suffering from an ocular degenerative disease, preferably at an early stage of the ocular disease or from a healthy mammal known to be predisposed to an ocular degenerative disease (i.e., through genetic predisposition). In the latter case, the isolated MLBM cell population can be stored after isolation, and can then be injected prophylactically during early stages of a later developed ocular disease. Preferably the diseased retina includes activated astrocytes, to which the cells from the MLBM cell population are targeted. Accordingly, early treatment of the eye when there is an associated gliosis is beneficial. Alternatively, the retina can be treated with a laser to stimulate local proliferation of activated astrocytes in the retina prior to administering the autologous MLBM cell population.

Hematopoietic stem cells are stem cells that are capable of developing into various blood cell types e.g., B cells, T cells, granulocytes, platelets, and erythrocytes. The lineage surface antigens are a group of cell-surface proteins that are markers of mature blood cell lineages, including CD2, CD3, CD11, CD11a, Mac-1 (CD11b:CD18), CD14, CD16, CD19, CD24, CD33, CD36, CD38, CD45, CD45RA, murine Ly-6G, murine TER-119, CD56, CD64, CD68, CD86 (B7.2), CD66b, human leucocyte antigen DR (HLA-DR), and CD235a (Glycophorin A). Hematopoietic stem cells that do not express significant levels of these antigens are commonly referred to a lineage negative ($Lin^-$). Human hematopoietic stem cells commonly express other surface antigens such as CD31, CD34, CD117 (c-kit) and/or CD133. Murine hematopoietic stem cells commonly express other surface antigens such as CD34, CD117 (c-kit), Thy-1, and/or Sca-1.

Isolated hematopoietic stem cells that do not express significant levels of a "lineage surface antigen" (Lin) on their cell surfaces are referred to herein as "lineage negative" or "$Lin^-$" hematopoietic stem cells i.e., $Lin^-HSC$. A majority of the cells of the MLBM cell populations of the present invention are $Lin^-$ and express both a relatively high amount of the CD44 antigen ($CD44^{hi}$) as well as the CD11b antigen. These $CD44^+CD11b^+Lin^-HSC$ are capable of incorporating into developing vasculature and then differentiating to become vascular endothelial cells.

As used herein and in the appended claims, the phrase "adult" in reference to bone marrow and bone marrow cells, includes bone marrow isolated postnatally, i.e., from juvenile and adult individuals, as opposed to embryos. Accordingly, the term "adult mammal" refers to both juvenile (postnatal) and fully mature mammals, as opposed to an embryo or prenatal individual.

The isolated MLBM cell populations of the present invention selectively target astrocytes and incorporate into the retinal neovasculature when intravitreally injected into the eye of the mammalian species, such as a mouse or a human, from which the cells were isolated.

The isolated MLBM cell populations of the present invention include cells that differentiate to endothelial cells and generate vascular structures within the retina. In particular, the MLBM cell population of the present invention is useful for the treatment of retinal neovascular and retinal vascular degenerative diseases, and for repair of retinal vascular injury. The MLBM cell population of the present invention also promotes neuronal rescue in the retina and promote upregulation of anti-apoptotic genes. Additionally, the MLBM cell population of the invention can be utilized to treat retinal defects in the eyes of neonatal mammals, such as mammals suffering from oxygen induced retinopathy or retinopathy of prematurity.

It has been found that bone marrow cells that do not express CD44 ($CD44^{LO}$ cells) generally express one or more of the following cell markers: Ter119, CD45RB220, and CD3e. Utilizing this fact, $CD44^{HI}$ MLBM cells of the present invention can be isolated by a method involving negative cell-marker selection. The method comprises contacting a plurality of bone marrow cells with antibodies specific for Ter119, CD45RB220, and CD3e, removing cells from the plurality of bone marrow cells that immunoreact with Ter119, CD45RB220, and CD3e antibodies, and recovering myeloid-like bone marrow cells that are deleted in Ter119, CD45RB220, and CD3e-expressing cells. Using this method, a cell population can be recovered in which greater than 90 percent of the cells express CD44.

The present invention also provides a method of treating ocular diseases in a mammal comprising isolating from the bone marrow of the mammal a MLBM cell population, and intravitreally injecting cells from the MLBM cell population into an eye of the mammal in a number sufficient to arrest the disease. The present method can be utilized to treat ocular diseases such as retinal degenerative diseases, retinal vascular degenerative diseases, ischemic retinopathies, vascular hemorrhages, vascular leakage, and choroidopathies in neonatal, juvenile or fully mature mammals. Examples of such diseases include age related macular degeneration (ARMD), diabetic retinopathy (DR), presumed ocular histoplasmosis (POHS), retinopathy of prematurity (ROP), sickle cell anemia, and retinitis pigmentosa, as well as retinal injuries.

The number of cells from the MLBM cell population injected into the eye is sufficient for arresting the disease state of the eye. For example, the amount of injected cells can be effective for repairing retinal damage of the eye, stabilizing retinal neovasculature, maturing retinal neovasculature, and preventing or repairing vascular leakage and vascular hemorrhage.

Cells from the MLBM cell population of the present invention can be transfected with therapeutically useful genes, such as genes encoding antiangiogenic proteins for use in ocular, cell-based gene therapy and genes encoding neurotrophic agents to enhance neuronal rescue effects.

The transfected cells can include any gene which is therapeutically useful for treatment of retinal disorders. In one preferred embodiment, the transfected cells from the MLBM cell population of the present invention include a gene operably encoding an antiangiogenic peptide, including proteins, or protein fragments such as TrpRS or antiangiogenic (i.e., angiostatic) fragments thereof, e.g., the fragments of TrpRS designated T2-TrpRS (SEQ ID NO: 3 in FIG. 34), T2-TrpRS-GD (SEQ ID NO: 4 in FIG. 34), both of which are preferred angiostatic peptides, as well as mini-TrpRS (SEQ ID NO: 5 in FIG. 35), and T1-TrpRS (SEQ ID NO: 6 in FIG. 36). The transfected cells from the MLBM cell population encoding an antiangiogenic peptide of the present invention are useful for treatment of retinal diseases involving abnormal vascular development, such as diabetic retinopathy, and like diseases. Preferably, the cells from the MLBM cell population are human cells.

In another preferred embodiment, the transfected cells from the MLBM cell population of the present invention include a gene operably encoding a neurotrophic agent such as nerve growth factor, neurotrophin-3, neurotrophin-4, neurotrophin-5, ciliary neurotrophic factor, retinal pigmented epithelium-derived neurotrophic factor, insulin-like growth factor, glial cell line-derived neurotrophic factor, brain-derived neurotrophic factor, and the like. Such neurotrophic cells from the MLBM cell population are useful for promoting neuronal rescue in retinal neuronal degenerative diseases such as glaucoma and retinitis pigmentosa, in treatment of injuries to the retinal nerves, and the like. Implants of ciliary neurotrophic factor have been reported as useful for the treatment of retinitis pigmentosa (see Kirby et al. 2001, *Mol Ther.* 3(2):241-8; Farrar et al. 2002, *EMBO Journal* 21:857-864). Brain-derived neurotrophic factor reportedly modulates growth associated genes in injured retinal ganglia (see Fournier, et al., 1997, *J. Neurosci. Res.* 47:561-572). Glial cell line derived neurotrophic factor reportedly delays photoreceptor degeneration in retinitis pigmentosa (see McGee et al. 2001, *Mol Ther.* 4(6):622-9).

The present invention also provides methods for treating ocular angiogenic diseases by administering transfected cells from the MLBM cell population of the present invention by intravitreal injection of the cells into the eye. Such transfected cells from the MLBM cell population comprise cells from the MLBM cell population transfected with a therapeutically useful gene, such as a gene encoding antiangiogenic or neurotrophic gene product. Preferably the transfected cells from the MLBM cell population are human cells.

Preferably, at least about $1 \times 10^5$ cells from the MLBM cell population or transfected cells from the MLBM cell population are administered by intravitreal injection to a mammalian eye suffering from a retinal degenerative disease. The number of cells to be injected may depend upon the severity of the retinal degeneration, the age of the mammal and other factors that will be readily apparent to one of ordinary skill in the art of treating retinal diseases. The cells from the MLBM cell population may be administered in a single dose or by multiple dose administration over a period of time, as determined by the clinician in charge of the treatment.

The MLBM cell populations of the present invention is useful for the treatment of retinal injuries and retinal defects involving an interruption in or degradation of the retinal vasculature or retinal neuronal degeneration. Human MLBM cell populations also can be used to generate a line of genetically identical cells, i.e., clones, for use in regenerative or reparative treatment of retinal vasculature, as well as for treatment or amelioration of retinal neuronal degeneration. Furthermore, the MLBM cell populations of the present invention are useful as research tools to study retinal vascular development and to deliver genes to selected cell targets, such as astrocytes.

Murine Retinal Vascular Development.

A Model for Ocular Angiogenesis. The mouse eye provides a recognized model for the study of mammalian retinal vascular development, such as human retinal vascular development. During development of the murine retinal vasculature, ischemia-driven retinal blood vessels develop in close association with astrocytes. These glial elements migrate onto the third trimester human fetus, or the neonatal rodent, retina from the optic disc along the ganglion cell layer and spread radially. As the murine retinal vasculature develops, endothelial cells utilize this already established astrocytic template to determine the retinal vascular pattern (See FIGS. 1(a and b)). FIGS. 1(a and b) depicts schematic diagrams of developing mouse retina. Panel (a) depicts development of the primary plexus (dark lines at upper left of the diagram) superimposed over the astrocyte template (light lines) whereas, (b) depicts the second phase of retinal vessel formation. In FIG. 1, GCL stands for ganglion cell layer; IPL stands for inner plexus layer; INL stands for inner nuclear layer; OPL stands for outer plexus layer; ONL stands for outer nuclear layer; RPE stands for retinal pigment epithelium; ON stands for optic nerve; and P stands for periphery.

At birth, retinal vasculature is virtually absent. By postnatal day 14 (P14) the retina has developed complex primary (superficial) and secondary (deep) layers of retinal vessels coincident with the onset of vision. Initially, spoke-like peripapillary vessels grow radially over the pre-existing astrocytic network towards the periphery, becoming progressively interconnected by capillary plexus formation. These vessels grow as a monolayer within the nerve fiber through P10 (FIG. 1(a)). Between P7-P8 collateral branches begin to sprout from this primary plexus and penetrate into the retina to the outer plexiform layer where they form the secondary, or deep, retinal plexus. By P21, the entire network undergoes extensive remodeling and a tertiary, or intermediate, plexus forms at the inner surface of inner nuclear layer (FIG. 1(b)).

The neonatal mouse retinal angiogenesis model is useful for studying the role of HSC during ocular angiogenesis for several reasons. In this physiologically relevant model, a large astrocytic template exists prior to the appearance of endogenous blood vessels, permitting an evaluation of the role for cell-cell targeting during a neovascular process. In addition, this consistent and reproducible neonatal retinal vascular process is known to be hypoxia-driven, in this respect having similarities to many retinal diseases in which ischemia is known to play a role.

Enrichment of Endothelial Progenitor Cells (EPC) from Bone Marrow.

Although cell surface marker expression has been extensively evaluated on the EPC population found in preparations of HSC, markers that uniquely identify EPC are still poorly defined. To enrich for EPC, hematopoietic lineage marker positive cells (Lin$^+$), i.e., B lymphocytes (CD45), T lymphocytes (CD3), granulocytes (Ly-6G), monocytes (CD11), and erythrocytes (TER-119), were depleted from bone marrow mononuclear cells of mice. Sca-1 antigen was used to further enrich for EPC. A comparison of results obtained after intravitreal injection of identical numbers of either Lin$^-$ Sca-1$^+$ cells or Lin$^-$ cells, no difference was detected between the two groups. In fact, when only Lin⁻Sca-1⁻ cells were injected, far greater incorporation into developing blood vessels was observed.

Lin⁻HSC populations are enriched with EPCs, based on functional assays. Furthermore, Lin⁺HSC populations functionally behave quite differently from the Lin⁻ HSC populations. Epitopes commonly used to identify EPC for each fraction (based on previously reported in vitro characterization studies) were also evaluated. While none of these markers were exclusively associated with the Lin⁻ fraction, all were increased about 70 to about 1800% in the Lin⁻ HSC, compared to the Lin⁺HSC fraction (FIG. 1(c)). FIG. 1, Panel (c) illustrates flow cytometric characterization of bone marrow-derived Lin⁺ HSC and Lin⁻ HSC separated cells. The top row of Panel (c) shows a hematopoietic stem cell dot plot distribution of non-antibody labeled cells. R1 defines the quantifiable-gated area of positive PE-staining; R2 indicates GFP-positive. Dot plots of Lin⁻ HSC are shown in the middle row and dot plots of Lin⁺ HSC are shown in the bottom row. The C57B/6 cells were labeled with the PE-conjugated antibodies for Sca-1, c-kit, Flk-1/KDR, CD31. Tie-2 data was obtained from Tie-2-GFP mice. The percentages in the corners of the dot plots indicate the percent of positive-labeled cells out of total Lin⁻ or Lin⁺ HSC population. Interestingly, accepted EPC markers like Flk-1/KDR, Tie-2, and Sca-1 were poorly expressed and, thus, not used for further fractionation.

Lin⁻ HSC can be isolated by (a) extracting bone marrow from an adult mammal; (b) separating a plurality of monocytes from the bone marrow; (c) labeling the monocytes with biotin-conjugated lineage panel antibodies to one or more lineage surface antigens, preferably lineage surface antigens selected from the group consisting of CD2, CD3, CD4, CD11, CD11a, Mac-1, CD14, CD16, CD19, CD24, CD33, CD36, CD38, CD45, Ly-6G (murine), TER-119 (murine), CD45RA, CD56, CD64, CD68, CD86 (B7.2), CD66b, human leucocyte antigen DR (HLA-DR), and CD235a (Glycophorin A); (d) removing monocytes that are positive for said one or more lineage surface antigens from the plurality of monocytes; and (e) recovering a population of lineage negative hematopoietic stem cells therefrom.

When the Lin⁻ HSC are isolated from adult human bone marrow, preferably the monocytes are labeled with biotin-conjugated lineage panel antibodies to lineage surface antigens CD2, CD3, CD4, CD11a, Mac-1, CD14, CD16, CD19, CD33, CD38, CD45RA, CD64, CD68, CD86 (B7.2), and CD235a. When the Lin⁻ HSC are isolated from adult murine bone marrow, preferably the monocytes are labeled with biotin-conjugated lineage panel antibodies to lineage surface antigens CD3, CD11, CD45, Ly-6G, and TER-119.

Intravitreally Injected HSC Lin⁻ Cells Contain EPC that Target Astrocytes and Incorporate into Developing Retinal Vasculature.

Figure 2:
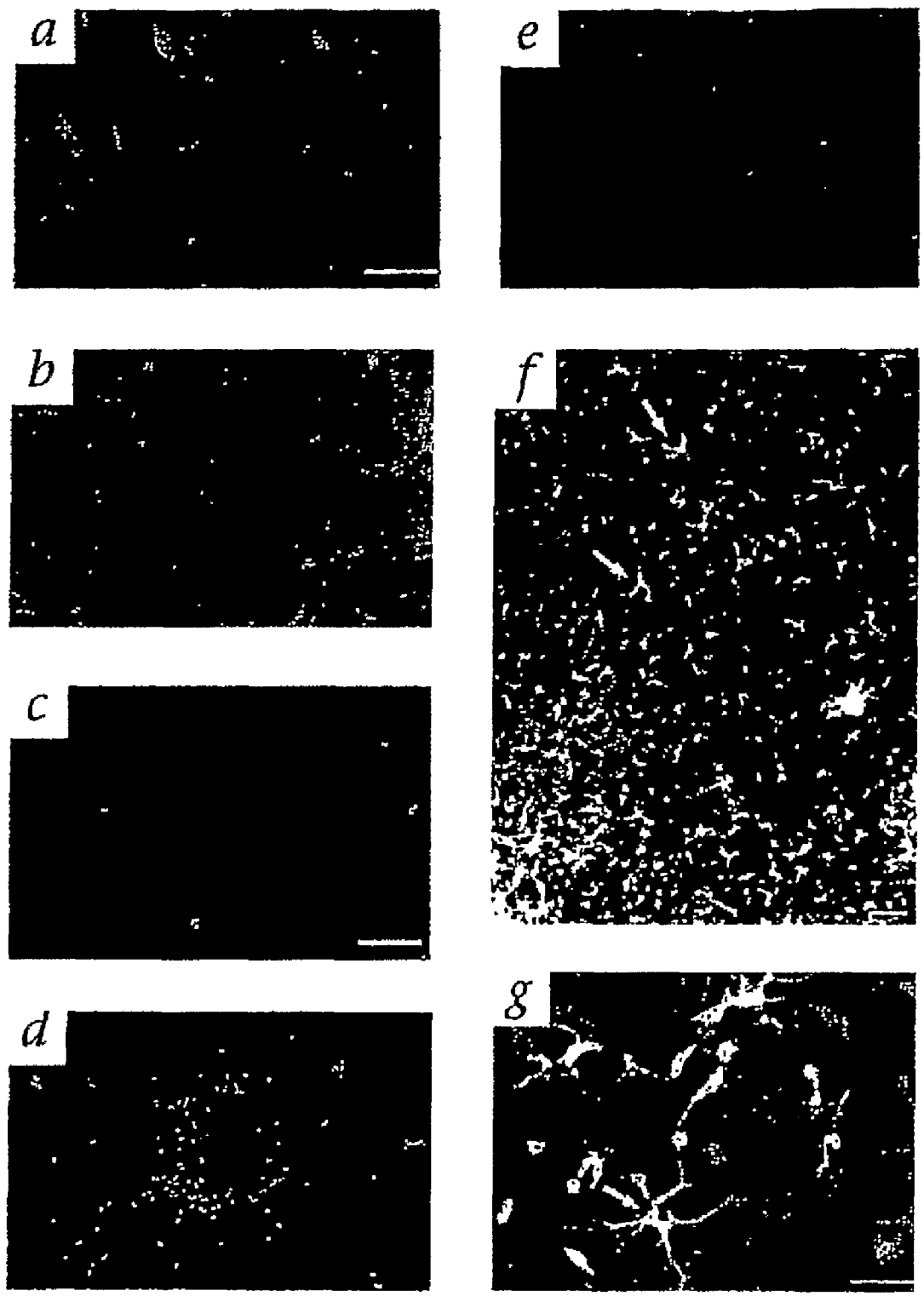
FIG. 2 depicts engraftment of Lin$^-$HSCs into developing mouse retina. (a) At four days post-injection (P6) intravitreally injected eGFP$^+$ Lin$^-$HSC cells attach and differentiate on the retina. (b) Lin$^-$HSC (B6. 129S7-Gtrosa26 mice, stained with β-gal antibody) establish themselves ahead of the vasculature stained with collagen IV antibody (asterisk indicates tip of vasculature). (c) Most of Lin$^+$HSC cells (eGFP$^+$) at four days post-injection (P6) were unable to differentiate. (d) Mesenteric eGFP$^+$ murine EC four days post-injection (P6). (e) Lin$^-$ HSCs (eGFP$^+$) injected into adult mouse eyes. (f) Low magnification of eGFP$^+$ Lin$^-$ HSCs (arrows) homing to and differentiating along the pre-existing astrocytic template in the GFAP-GFP transgenic mouse. (g) Higher magnification of association between Lin$^-$ cells (eGFP) and underlying astrocyte (arrows). (h) Non-injected GFAP-GFP transgenic control. (i) Four days post-injection (P6), eGFP$^+$ Lin$^-$HSCs migrate to and undergo differentiation in the area of the future deep plexus. Left figure captures Lin$^-$ HSC activity in a whole mounted retina; right figure indicates location of the Lin$^-$ cells (arrows) in the retina (top is vitreal side, bottom is scleral side). (j) Double labeling with α-CD31-PE and α-GFP-alexa 488 antibodies. Seven days after injection, the injected Lin$^-$ HSCs (eGFP, red) were incorporated into the vasculature (CD31). Arrowheads indicate the incorporated areas. (k) eGFP$^+$ Lin$^-$ HSC cells form vessels fourteen days post-injection (P17). (l and m) Intra-cardiac injection of rhodamine-dextran indicates that the vessels are intact and functional in both the primary (l) and deep plexus (m).

To determine whether intravitreally injected Lin⁻ HSC can target specific cell types of the retina, utilize the astrocytic template and participate in retinal angiogenesis, approximately 10⁵ cells from a Lin⁻ HSC composition of the present invention or Lin⁺ HSC cells (control, about 10⁵ cells) isolated from the bone marrow of adult (GFP or LacZ transgenic) mice were injected into postnatal day 2 (P2) mouse eyes. Four days after injection (P6), many cells from the Lin⁻ HSC composition of the present invention, derived from GFP or LacZ transgenic mice were adherent to the retina and had the characteristic elongated appearance of endothelial cells (FIG. 2(a)). FIG. 2 illustrates engraftment of Lin⁻ cells into developing mouse retina. As shown in FIG. 2, Panel (a), the four days post-injection (P6) intravitreally injected eGFP+ Lin⁻ HSC attach and differentiate on the retina.

In many areas of the retinas, the GFP-expressing cells were arranged in a pattern conforming to underlying astrocytes and resembled blood vessels. These fluorescent cells were observed ahead of the endogenous, developing vascular network (FIG. 2(b)). Conversely, only a small number of Lin⁺ HSC (FIG. 2(c)), or adult mouse mesenteric endothelial cells (FIG. 2(d)) attached to the retinal surface. In order to determine whether cells from an injected Lin⁻ HSC population could also attach to retinas with already established vessels, a Lin⁻ HSC composition was injected into adult eyes. Interestingly, no cells were observed to attach to the retina or incorporate into established, normal retinal blood vessels (FIG. 2(e)). This indicates that the Lin⁻ HSC compositions of the present invention do not disrupt a normally developed vasculature and will not initiate abnormal vascularization in normally developed retinas.

In order to determine the relationship between an injected Lin⁻ HSC compositions of the present invention and retinal astrocytes, a transgenic mouse was used, which expressed glial fibrillary acidic protein (GFAP, a marker of astrocytes) and promoter-driven green fluorescent protein (GFP). Examination of retinas of these GFAP-GFP transgenic mice injected with Lin⁻ HSC from eGFP transgenic mice demonstrated co-localization of the injected eGFP EPC and existing astrocytes (FIG. 2(f-h), arrows). Processes of eGFP+Lin⁻ HSC were observed to conform to the underlying astrocytic network (arrows, FIG. 2(g)). Examination of these eyes demonstrated that the injected, labeled cells only attached to astrocytes; in P6 mouse retinas, where the retinal periphery does not yet have endogenous vessels, injected cells were observed adherent to astrocytes in these not yet vascularized areas. Surprisingly, injected, labeled cells were observed in the deeper layers of the retina at the precise location where normal retinal vessels will subsequently develop (FIG. 2(i), arrows).

To determine whether injected Lin⁻ HSC are stably incorporated into the developing retinal vasculature, retinal vessels at several later time points were examined. As early as P9 (seven days after injection), Lin⁻ HSC incorporated into CD31⁺ structures (FIG. 2(j)). By P16 (14 days after injection), the cells were already extensively incorporated into retinal vascular-like structures (FIG. 2(k)). When rhodamine-dextran was injected intravascularly (to identify functional retinal blood vessels) prior to sacrificing the animals, the majority of Lin⁻ HSC were aligned with patent vessels (FIG. 2(l)). Two patterns of labeled cell distribution were observed: (1) in one pattern, cells were interspersed along vessels in between unlabeled endothelial cells; and (2) the other pattern showed that vessels were composed entirely of labeled cells. Injected cells were also incorporated into vessels of the deep vascular plexus (FIG. 2(m)). While sporadic incorporation of Lin⁻ HSC-derived EPC into neovasculature has been previously reported, this is the first report of vascular networks being entirely composed of these cells. This demonstrates that cells from a population of bone marrow-derived Lin⁻ HSC, injected intravitreally, can efficiently incorporate into any layer of the forming retinal vascular plexus.

Histological examination of non-retinal tissues (e.g., brain, liver, heart, lung, bone marrow) did not demonstrate the presence of any GFP positive cells when examined up to 5 or 10 days after intravitreal injection. This indicates that a subpopulation of cells within the Lin⁻ HSC fraction selectively target to retinal astrocytes and stably incorporate into developing retinal vasculature. Since these cells have many characteristics of endothelial cells (association with retinal astrocytes, elongate morphology, stable incorporation into patent vessels and not present in extravascular locations), these cells represent EPC present in the Lin⁻ HSC population. The targeted astrocytes are of the same type observed in many of the hypoxic retinopathies. It is well known that glial cells are a prominent component of neovascular fronds of tufts observed in DR and other forms of retinal injury. Under conditions of reactive gliosis and ischemia-induced neovascularization, activated astrocytes proliferate, produce cytokines, and up-regulate GFAP, similar to that observed during neonatal retinal vascular template formation in many mammalian species including humans.

Figure 3:
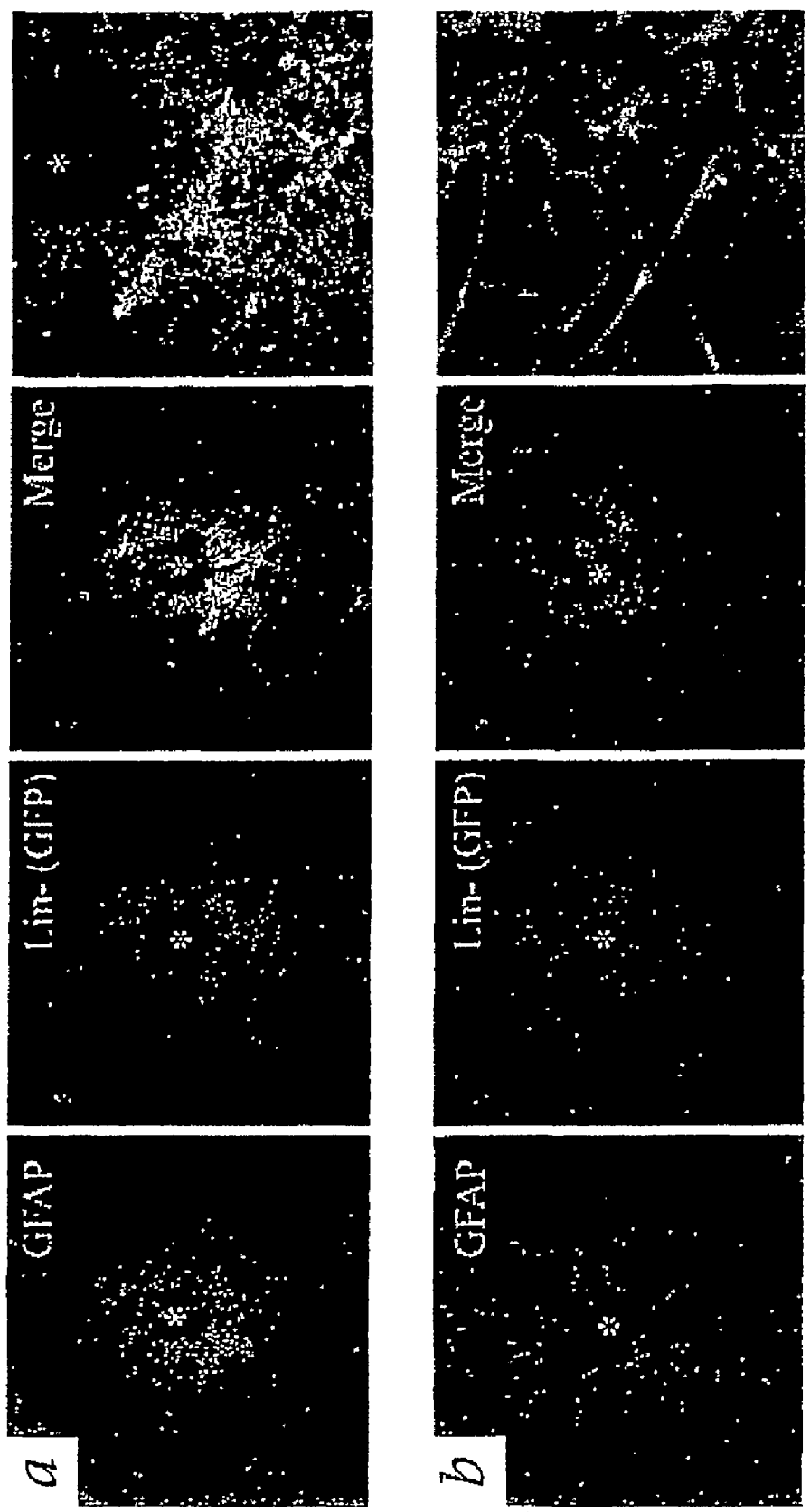
FIG. 3 shows that eGFP$^+$ Lin$^-$HSC cells home to the gliosis (indicated by GFAP expressing-astrocytes, far left image) induced by both laser (a) and mechanical (b) induced injury in the adult retina (asterisk indicates injured site). Far right images are a higher magnification, demonstrating the close association of the Lin$^-$HSCs and astrocytes. Calibration bar=20 μM.

Lin⁻ HSC populations will target activated astrocytes in adult mouse eyes as they do in neonatal eyes, Lin⁻ HSC cells were injected into adult eyes with retinas injured by photocoagulation (FIG. 3(a)) or needle tip (FIG. 3(b)). In both models, a population of cells with prominent GFAP staining was observed only around the injury site (FIGS. 3(a and b)). Cells from injected Lin⁻ HSC compositions localized to the injury site and remained specifically associated with GFAP-positive astrocytes (FIGS. 3(a and b)). At these sites, Lin⁻ HSC cells were also observed to migrate into the deeper layer of retina at a level similar to that observed during neonatal formation of the deep retinal vasculature. Uninjured portions of retina contained no Lin⁻ HSC cells, identical to that observed when Lin⁻ HSC were injected into normal, uninjured adult retinas (FIG. 2(e)). These data indicate that Lin⁻ HSC compositions can selectively target activated glial cells in injured adult retinas with gliosis as well as neonatal retinas undergoing vascularization.

Intravitreally Injected Lin⁻ HSC can Rescue and Stabilize Degenerating Vasculature.

Since intravitreally injected Lin⁻ HSC compositions target astrocytes and incorporate into the normal retinal vasculature, these cells also stabilize degenerating vasculature in ischemic or degenerative retinal diseases associated with gliosis and vascular degeneration. The rd/rd mouse is a model for retinal degeneration that exhibits profound degeneration of photoreceptor and retinal vascular layers by one month after birth. The retinal vasculature in these mice develops normally until P16 at which time the deeper vascular plexus regresses; in most mice the deep and intermediate plexuses have nearly completely degenerated by P30.

Figure 4:
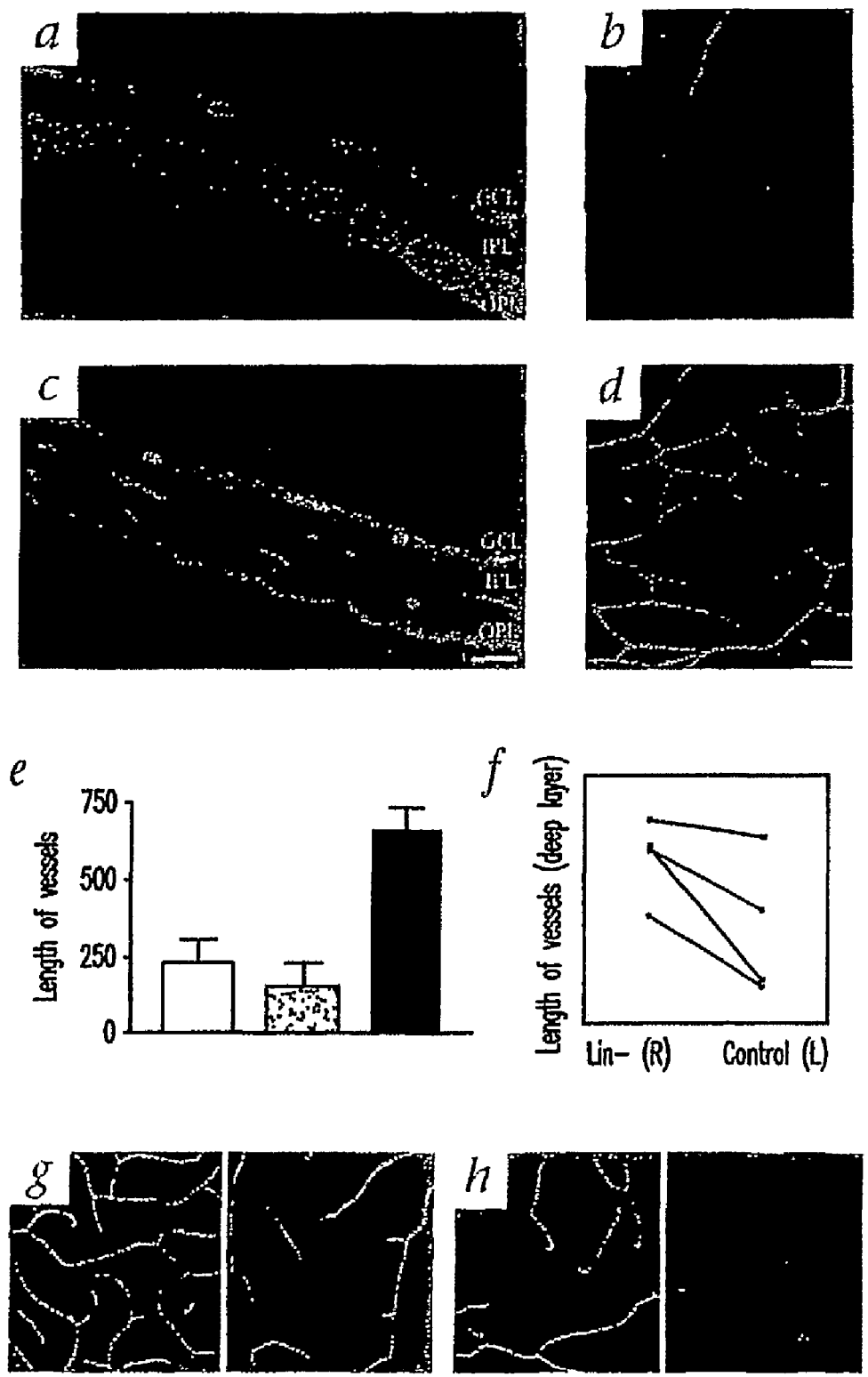
FIG. 4 shows that Lin$^-$HSC cells rescue the vasculature of the retinal degeneration mouse. (a-d) Retinas at 27 days post-injection (P33) with collagen IV staining; (a) and (b), retinas injected with Lin$^+$ HSC cells (Balb/c) showed no difference in vasculature from normal FVB mice; (c) and (d) retinas injected with Lin$^-$HSCs (Balb/c) exhibited a rich vascular network analogous to a wild-type mouse; (a) and (c), frozen sections of whole retina (top is vitreal side, bottom is scleral side) with DAPI staining; (b) and (d), deep plexus of retinal whole amount; (e) bar graph illustrating the increase in vascularity of the deep vascular plexus formed in the Lin⁻HSC cell-injected retinas (n=6). The extent of deep retinal vascularization was quantified by calculating the total length of vessels within each image. Average total length of vessels/high power field (in microns) for Lin⁻HSC, Lin⁺HSC or control retinas were compared. (f) Comparison of the length of deep vascular plexus after injection with Lin⁻HSC (R, right eye) or Lin⁺HSC (L, left eye) cells from rd/rd mouse. The results of six independent mice are shown (each color represents a separate mouse). (g) and (h) Lin⁻HSC cells also (Balb/c) rescued the rd/rd vasculature when injected into P15 eyes. The intermediate and deep vascular plexus of Lin⁻HSC (G) or Lin⁺HSC (H) cell injected retinas (one month after injection) are shown.

To determine whether HSC can rescue the regressing vessels, Lin⁺ or Lin⁻ HSC (from Balb/c mice) were injected into rd/rd mice intravitreally at P6. By P33, after injection with Lin⁺ cells, vessels of the deepest retinal layer were nearly completely absent (FIGS. 4(a and b)). In contrast, most Lin⁻ HSC-injected retinas by P33 had a nearly normal retinal vasculature with three parallel, well-formed vascular layers (FIGS. 4(a and d)). Quantification of this effect demonstrated that the average length of vessels in the deep vascular plexus of Lin⁻ injected rd/rd eyes was nearly three times greater than untreated or Lin⁺ cell-treated eyes (FIG. 4(e)). Surprisingly, injection of a Lin⁻ HSC composition derived from rd/rd adult mouse (FVB/N) bone marrow also rescued degenerating rd/rd neonatal mouse retinal vasculature (FIG. 4(f)). Degeneration of the vasculature in rd/rd mouse eyes in observed as early as 2-3 weeks post-natally. Injection of Lin⁻ HSC as late as P15 also resulted in partial stabilization of the degenerating vasculature in the rd/rd mice for at least one month (FIGS. 4(g and h)).

Figure 5:
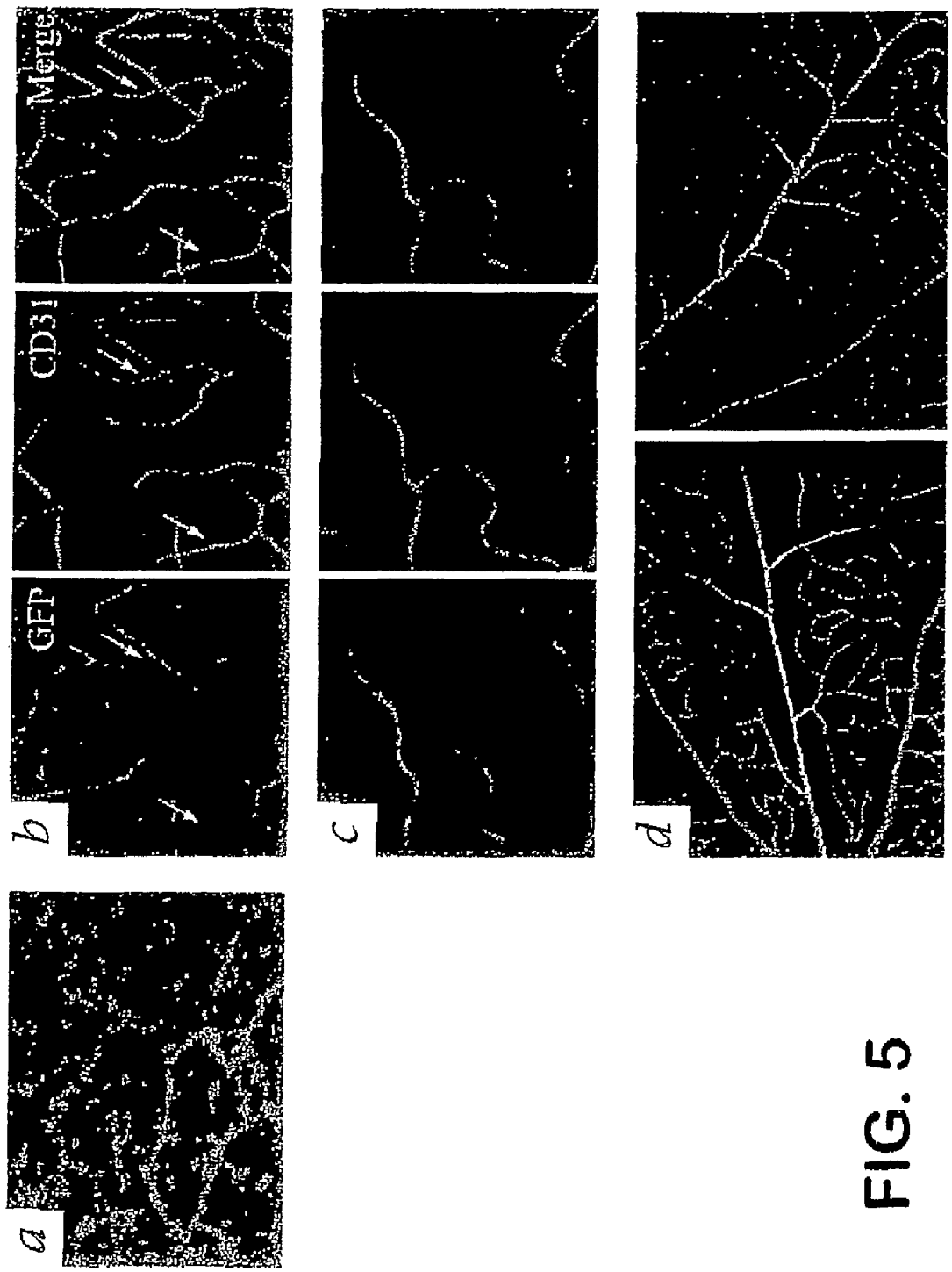
FIG. 5 depicts photomicrographs of mouse retinal tissue: (a) deep layer of retinal whole mount (rd/rd mouse), five days post-injection (P11) with eGFP⁺ Lin⁻HSCs visible (gray). (b) and (c) P60 retinal vasculature of Tie-2-GFP (rd/rd) mice that received Balb/c Lin⁻ cells (b) or Lin⁺HSC cell (c) injection at P6. Only endogenous endothelial cells (GFP-stained) are visible in the left panels of (b) and (c). The middle panels of (b) and (e) are stained with CD31 antibody; arrows indicate the vessels stained with CD31 but not with GFP, the right panels of (b) and (e) show staining with both GFP and CD31. (d) α-SMA staining of Lin⁻ HSC injected (left panel) and control retina (right panel).

A Lin⁻ HSC composition injected into younger (e.g., P2) rd/rd mice also incorporated into the developing superficial vasculature. By P11, these cells were observed to migrate to the level of the deep vascular plexus and form a pattern identical to that observed in the wild type outer retinal vascular layer (FIG. 5(a)). In order to more clearly describe the manner in which cells from injected Lin⁻ HSC compositions incorporate into, and stabilize, degenerating retinal vasculature in the rd/rd mice, a Lin⁻ HSC composition derived from Balb/c mice was injected into Tie-2-GFP FVB mouse eyes. The FVB mice have the rd/rd genotype and because they express the fusion protein Tie-2-GFP, all endogenous blood vessels are fluorescent.

When non-labeled cells from a Lin⁻ HSC composition are injected into neonatal Tie-2-GFP FVB eyes and are subsequently incorporated into the developing vasculature, there should be non-labeled gaps in the endogenous, Tie-2-GFP labeled vessels that correspond to the incorporated, non-labeled Lin⁻ HSC that was injected. Subsequent staining with another vascular marker (e.g., CD-31) then delineates the entire vessel, permitting determination as to whether non-endogenous endothelial cells are part of the vasculature. Two months after injection, CD31-positive, Tie-2-GFP negative, vessels were observed in the retinas of eyes injected with the Lin⁻ HSC composition (FIG. 5(b)). Interestingly, the majority of rescued vessels contained Tie-2-GFP positive cells (FIG. 5(c)). The distribution of pericytes, as determined by staining for smooth muscle actin, was not changed by Lin⁻ HSC injection, regardless of whether there was vascular rescue (FIG. 5(d)). These data clearly demonstrate that intravitreally injected Lin⁻ HSC cells migrate into the retina, participate in the formation of normal retinal blood vessels, and stabilize endogenous degenerating vasculature in a genetically defective mouse.

Inhibition of Retinal Angiogenesis by Transfected Cells from Lin⁻ HSC.

The majority of retinal vascular diseases involve abnormal vascular proliferation rather than degeneration. Transgenic cells targeted to astrocytes can be used to deliver an anti-angiogenic protein and inhibit angiogenesis. Cells from Lin⁻ HSC compositions were transfected with T2-tryptophanyl-tRNA synthetase (T2-TrpRS). T2-TrpRS is a 43 kD fragment of TrpRS that potently inhibits retinal angiogenesis (FIG. 6(a)). On P12, retinas of eyes injected with a control plasmid-transfected Lin⁻ HSC composition (no T2-TrpRS gene) on P2 had normal primary (FIG. 6(c)) and secondary (FIG. 6(d)) retinal vascular plexuses. When the T2-TrpRS transfected Lin⁻ HSC composition of the present invention was injected into P2 eyes and evaluated 10 days later, the primary network had significant abnormalities (FIG. 6(e)) and formation of the deep retinal vasculature was nearly completely inhibited (FIG. 6(f)). The few vessels observed in these eyes were markedly attenuated with large gaps between vessels. The extent of inhibition by T2-TrpRS-secreting Lin⁻ HSCs is detailed in Table 1.

Figure 6:
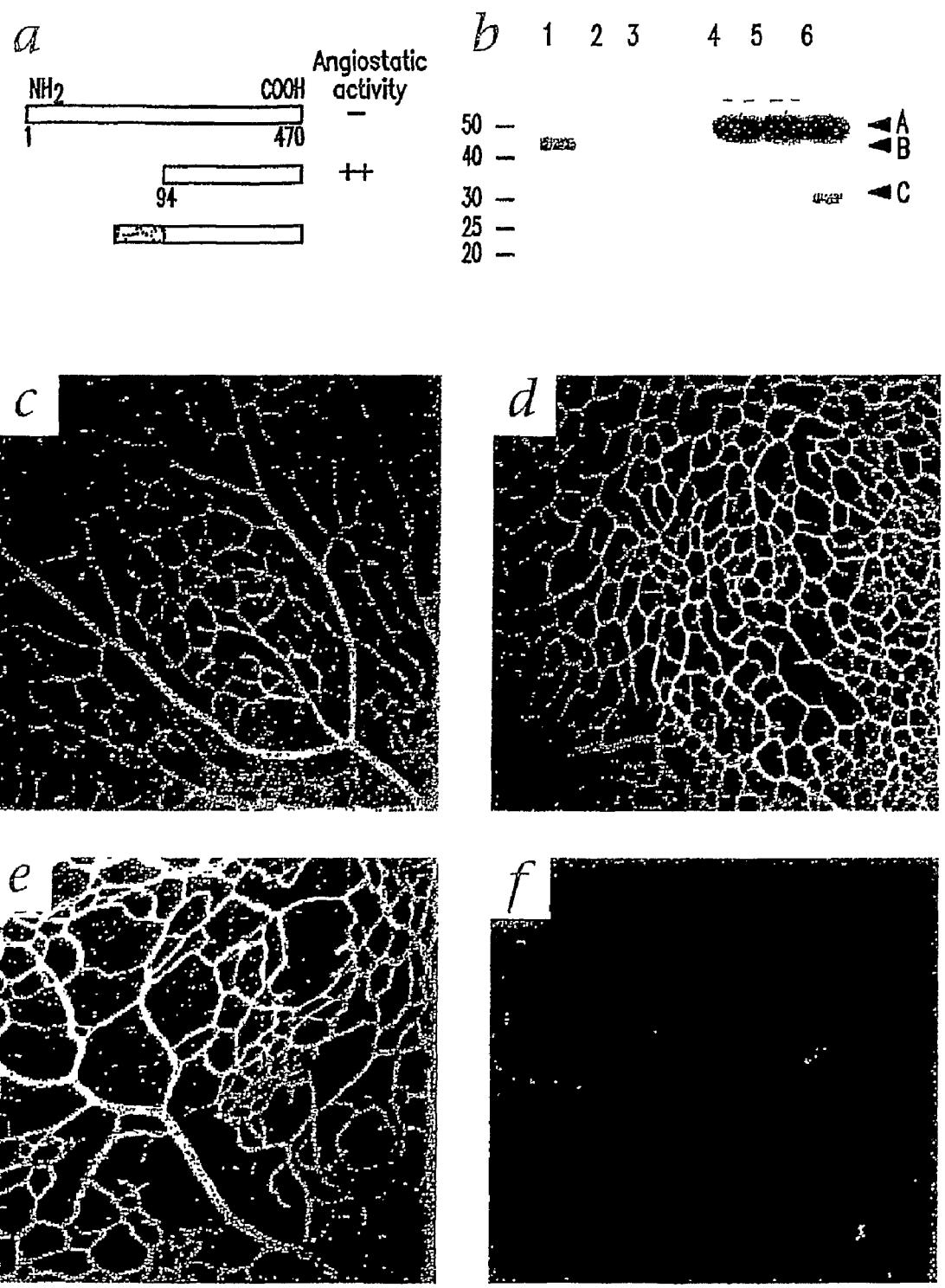
FIG. 6 shows that T2-TrpRS-transfected Lin⁻ HSCs inhibit the development of mouse retinal vasculature. (a) Schematic representation of human TrpRS, T2-TrpRS and T2-TrpRS with an Igk signal sequence at the amino terminus. (b) T2-TrpRS transfected Lin⁻HSC-injected retinas express T2-TrpRS protein in vivo. (1) Recombinant T2-TrpRS produced in *E. coli*; (2) Recombinant T2-TrpRS produced in *E. coli*; (3) Recombinant T2-TrpRS produced in *E. coli*; (4) control retina; (5) Lin⁻HSC+pSecTag2A (vector only) injected retina; (6) Lin⁻HSC+pKLe135 (Igk-T2-TrpRS in pSecTag) injected retina. (a) Endogenous TrpRS. (b) Recombinant T2-TrpRS. (c) T2-TrpRS of Lin⁻HSC injected retina. (c-f) Representative primary (superficial) and secondary (deep) plexuses of injected retinas, seven days post-injection; (c) and (d) Eyes injected with empty plasmid-transfected Lin⁻HSC developed normally; (e) and (f) the majority of T2-TrpRS-transfected Lin⁻HSC injected eyes exhibited inhibition of deep plexus; (c) and (e) primary (superficial) plexus; (d) and (f) secondary (deep) plexus. Faint outline of vessels observed in (f) are "bleed-through" images of primary network vessels shown in (e).

T2-TrpRS is produced and secreted by cells in the Lin⁻ HSC composition in vitro and after injection of these transfected cells into the vitreous, a 30 kD fragment of T2-TrpRS in the retina (FIG. 6(b)) was observed. This 30 kD fragment was specifically observed only in retinas injected with transfected Lin⁻ HSC and this decrease in apparent molecular weight compared to the recombinant or in vitro-synthesized protein may be due to processing or degradation of the T2-TrpRS in vivo. These data indicate that Lin⁻ HSC compositions can be used to deliver functionally active genes, such as genes expressing angiostatic molecules, to the retinal vasculature by targeting to activated astrocytes. While it is possible that the observed angiostatic effect is due to cell-mediated activity this is very unlikely since eyes treated with identical, but non-T2-transfected Lin⁻ HSC compositions had normal retinal vasculature.

TABLE 1

Vascular Inhibition by T2-TrpRS-secreting Lin⁻ HSCs

| | Primary Plexus | | Deep Plexus | | |
|---|---|---|---|---|---|
| | Inhibited | Normal | Complete | Partial | Normal |
| T2-TrpRS (15 eyes) | 60% (9 eyes) | 40% (6 eyes) | 33.3% (5 eyes) | 60% (9 eyes) | 6.7% (1 eye) |
| Control (13 eyes) | 0% (0 eyes) | 100% (13 eyes) | 0% (0 eyes) | 38.5% (5 eyes) | 61.5% (8 eyes) |

Intravitreally injected Lin⁻ HSC populations localize to retinal astrocytes, incorporate into vessels, and can be useful in treating many retinal diseases. While most cells from injected HSC compositions adhere to the astrocytic template, small numbers migrate deep into the retina, homing to regions where the deep vascular network will subsequently develop. Even though no GFAP-positive astrocytes were observed in this area prior to 42 days postnatally, this does not rule out the possibility that GFAP-negative glial cells are already present to provide a signal for Lin⁻ HSC localization. Previous studies have shown that many diseases are associated with reactive gliosis. In DR, in particular, glial cells and their extracellular matrix are associated with pathological angiogenesis.

Since cells from injected Lin⁻ HSC compositions specifically attached to GFAP-expressing glial cells, regardless of the type of injury, Lin⁻ HSC compositions of the present invention can be used to target pre-angiogenic lesions in the retina. For example, in the ischemic retinopathies, such as diabetes, neovascularization is a response to hypoxia. By targeting Lin⁻ HSC compositions to sites of pathological neovascularization, developing neovasculature can be stabilized preventing abnormalities of neovasculature such as hemorrhage or edema (the causes of vision loss associated with DR) and can potentially alleviate the hypoxia that originally stimulated the neovascularization. Abnormal blood vessels can be restored to normal condition. Furthermore, angiostatic proteins, such as T2-TrpRS can be delivered to sites of pathological angiogenesis by using transfected Lin⁻ HSC compositions and laser-induced activation of astrocytes. Since laser photocoagulation is commonly used in clinical ophthalmology, this approach has application for many retinal diseases. While such cell-based approaches have been explored in cancer therapy, their use for eye diseases is more advantageous since intraocular injection makes it possible to deliver large numbers of cells directly to the site of disease.

Neurotrophic and Vasculotrophic Rescue by Lin⁻HSC.

MACS was used to separate Lin⁻ HSC from bone marrow of enhanced green fluorescent protein (eGFP), C3H (rd/rd), FVB (rd/rd) mice as described above. Lin⁻ HSC containing EPC from these mice were injected intravitreally into P6 C3H or FVB mouse eyes. The retinas were collected at various time points (1 month, 2 months, and 6 months) after injection. The vasculature was analyzed by scanning laser confocal microscope after staining with antibodies to CD31 and retinal histology after nuclear staining with DAPI. Microarray gene expression analysis of mRNA from retinas at varying time points was also used to identify genes potentially involved in the effect.

Figure 12:
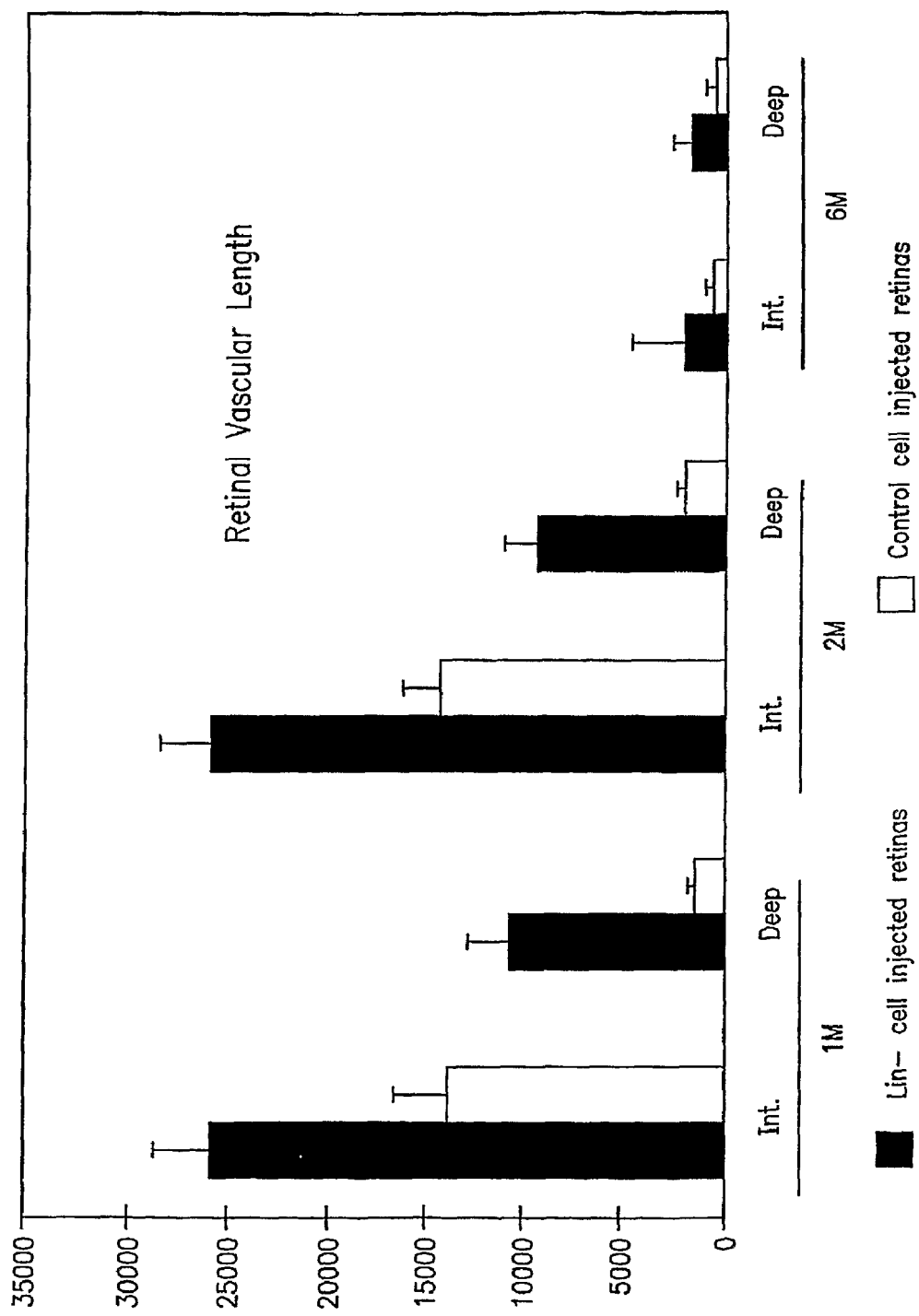
FIG. 12 is a bar graph of vascular length (y-axis) in arbitrary relative units for rd/rd mouse eyes treated with the Lin⁻HSC (dark bars) and untreated (light bars) rd/rd mouse eyes at time points of 1 month (1M), 2 months (2M), and 6 months (6M) post-injection.

Eyes of rd/rd mice had profound degeneration of both neurosensory retina and retinal vasculature by P21. Eyes of rd/rd mice treated with Lin⁻ HSC on P6 maintained a normal retinal vasculature for as long as 6 months; both deep and intermediate layers were significantly improved when compared to the controls at all time points (1M, 2M, and 6M) (see FIG. 12). In addition, we observed that retinas treated with Lin⁻HSC were also thicker (1M; 1.2-fold, 2M; 1.3-fold, 6M; 1.4-fold) and had greater numbers of cells in the outer nuclear layer (1M; 2.2-fold, 2M; 3.7-fold, 6M; 5.7-fold) relative to eyes treated with Lin⁺ HSC as a control. Large scale genomic analysis of "rescued" (e.g., Lin⁻ HSC) compared to control (untreated or non-Lin⁻ treated) rd/rd retinas demonstrated a significant upregulation of genes encoding sHSPs (small heat shock proteins) and specific growth factors that correlated with vascular and neural rescue, including genes encoding the proteins listed in FIG. 20, panels A and B.

The bone marrow derived Lin⁻ HSC populations significantly and reproducibly induced maintenance of a normal vasculature and dramatically increased photoreceptor and other neuronal cell layers in the rd/rd mouse. This neurotrophic rescue effect correlated with significant upregulation of small heat shock proteins and growth factors and provides insights into therapeutic approaches to currently untreatable retinal degenerative disorders.

Rd1/Rd1 Mouse Retinas Exhibit Profound Vascular and Neuronal Degeneration.

Figure 15:
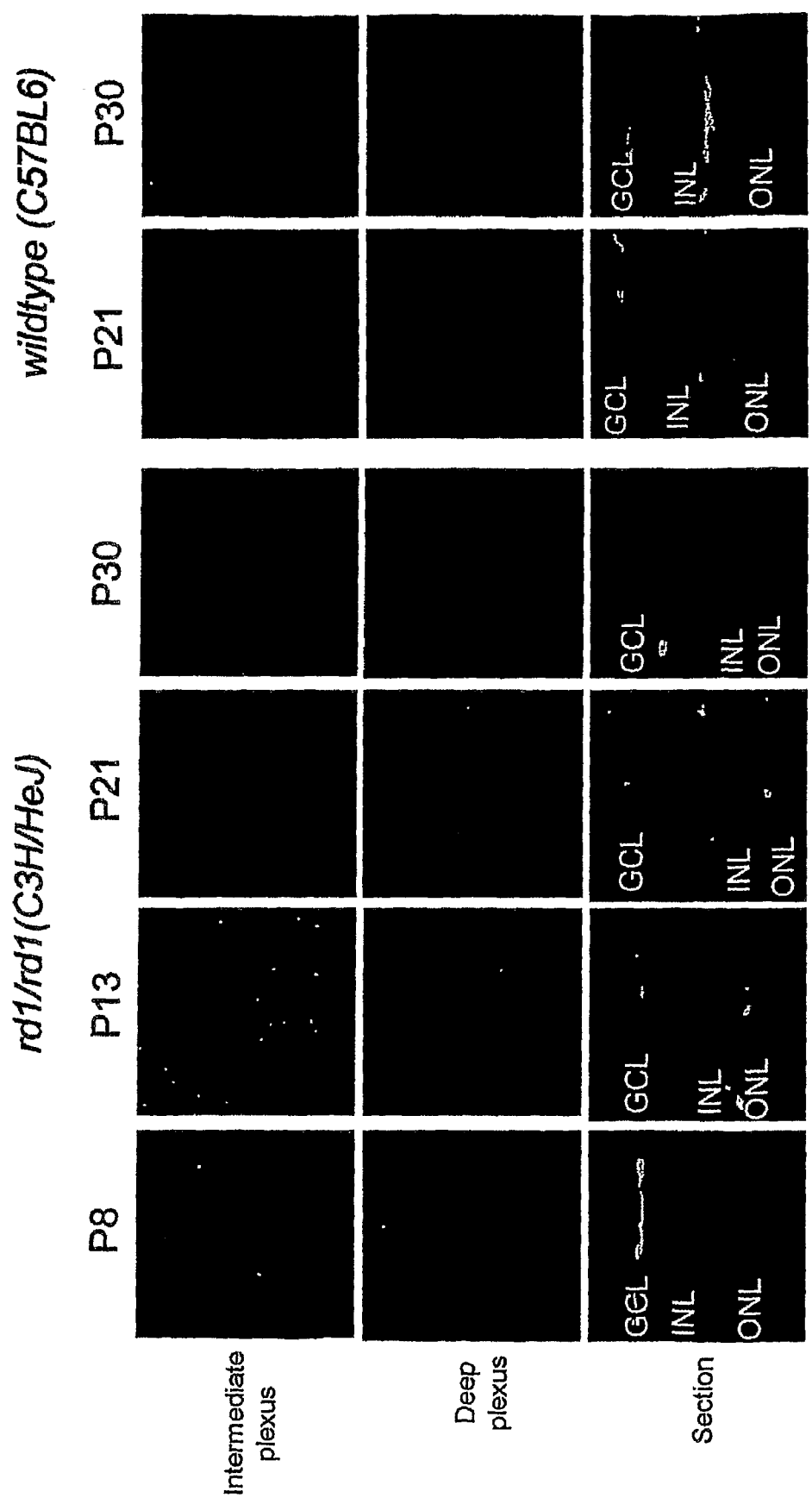
FIG. 15 depicts retinal vasculature and neural cell changes in rd1/rd1 (C3H/HeJ, left panels) or wild type mice (C57BL/6, right panels). Retinal vasculature of intermediate (upper panels) or deep (middle panels) vascular plexuses in whole-mounted retinas (red: collagen IV, green: CD31) and sections (red: DAPI, green: CD31, lower panels) of the same retinas are shown (P: postnatal day). (GCL: ganglion cell layer, INL: inter nuclear layer, ONL: outer nuclear layer).

Normal postnatal retinal vascular and neuronal development in mice has been well described and is analogous to changes observed in the third trimester human fetus (Dorrell et al., 2002, *Invest. Ophthalmol. Vis. Sci.* 43:3500-3510). Mice homozygous for the rd1 gene share many characteristics of human retinal degeneration (Frasson et al., 1999, *Nat. Med.* 5:1183-1187) and exhibit rapid photoreceptor (PR) loss accompanied by severe vascular atrophy as the result of a mutation in the gene encoding PR cGMP phosphodiesterase (Bowes et al. 1990, *Nature* 347:677-680). To examine the vasculature during retinal development and its subsequent degeneration, antibodies against collagen IV (CIV), an extracellular matrix (ECM) protein of mature vasculature, and CD31 (PECAM-1), a marker for endothelial cells, were used (FIG. 15). Retinas of rd1/rd1 (C3H/HeJ) developed normally until approximately postnatal day (P) 8 when degeneration of the photoreceptor-containing outer nuclear layer (ONL) began. The ONL rapidly degenerated and cells died by apoptosis such that only a single layer of nuclei remained by P20. Double staining of the whole-mounted retinas with antibodies to both CIV and CD31 revealed details of the vascular degeneration in rd1/rd1 mice similar to that described by others (Blanks et al., 1986, *J. Comp. Neurol.* 254:543-553). The primary and deep retinal vascular layers appeared to develop normally though P12 after which there is a rapid loss of endothelial cells as evidenced by the absence of CD31 staining. CD31 positive endothelial cells were present in a normal distribution through P12 but rapidly disappeared after that. Interestingly, CIV positive staining remained present throughout the time points examined, suggesting that the vessels and associated ECM formed normally, but only the matrix remained after P13 by which time no CD31 positive cells were observed. (FIG. 15, middle panels). The intermediate vascular plexus also degenerates after P21, but the progression is slower than that observed in the deep plexus (FIG. 15, upper panel). Retinal vascular and neural cell layers of a normal mouse are shown for comparison to the rd1/rd1 mouse (right panels, FIG. 15).

Neuroprotective Effect of Bone Marrow-Derived Lin⁻ HSCs in rd1/rd1 Mice.

Figure 16:
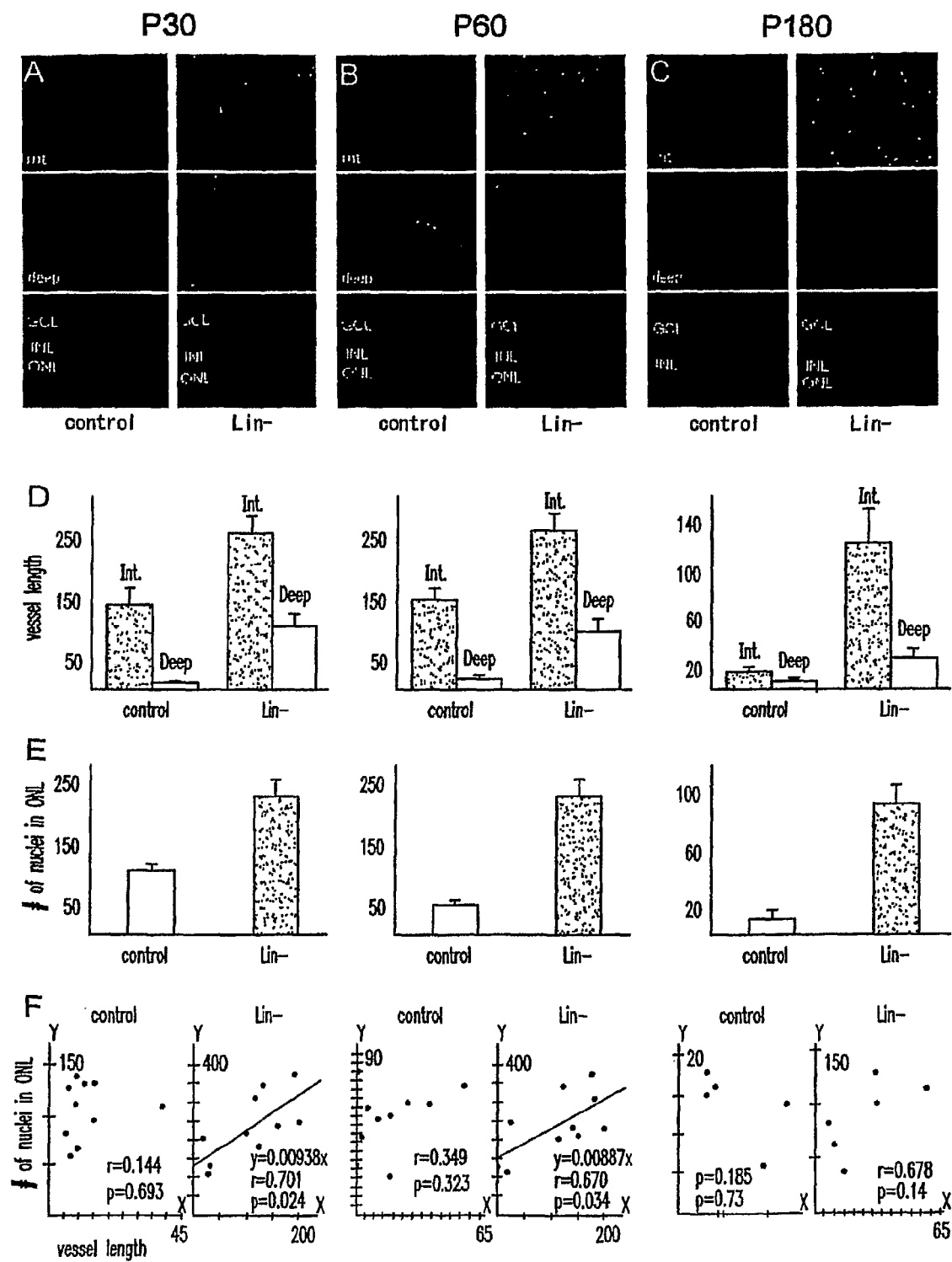
FIG. 16 shows that Lin⁻HSC injection rescues the degeneration of neural cells in rd1/rd1 mice. (A, B and C), retinal vasculature of intermediate (Int.) or deep plexus and sections of Lin⁻HSC injected eye (right panels) and contralateral control cell (CD31⁻) injected eye (left panels) at P30 (A), P60 (B), and P180 (C). (D), the average total length of vasculature (+ or − standard error of the mean) in Lin⁻HSC injected or control cell (CD31⁻) injected retinas at P30 (left, n=10), P60 (middle, n=10), and P180 (right, n=6). Data of intermediate (Int.) and deep vascular plexus are shown separately (Y axis: relative length of vasculature). (E), the average numbers of cell nuclei in the ONL at P30 (left, n=10), P60 (middle, n=10), or P180 (right, n=6) of control cell (CD31⁻) or Lin⁻HSC injected retinas (Y axis: relative number of cell nuclei in the ONL). (F), Linear correlations between the length of vasculature (X axis) and the number of cell nuclei in the ONL (Y axis) at P30 (left), P60 (middle), and P180 (right) of Lin⁻HSC or control cell injected retinas.

Intravitreally injected Lin⁻ HSCs incorporate into endogenous retinal vasculature in all three vascular plexuses and prevent the vessels from degenerating. Interestingly, the injected cells are virtually never observed in the outer nuclear layer. These cells either incorporate into the forming retinal vessels or are observed in close proximity to these vessels. Murine Lin⁻ HSCs (from C3H/HeJ) were intravitreally injected into C3H/HeJ (rd1/rd1) mouse eyes at P6, just prior to the onset of degeneration. By P30, control cell (CD31⁻)-injected eyes exhibited the typical rd1/rd1 phenotype, i.e., nearly complete degeneration of the deep vascular plexus and ONL was observed in every retina examined. Eyes injected with Lin⁻ HSCs maintained normal-appearing intermediate and deep vascular plexuses. Surprisingly, significantly more cells were observed in the internuclear layer (INL) and ONL of Lin⁻ HSC-injected eyes than in control cell-injected eyes (FIG. 16(A)). This rescue effect of Lin⁻ HSCs could be observed at 2 months (FIG. 16(B)) and for as long as 6 months after injection (FIG. 16(C)). Differences in the vasculature of the intermediate and deep plexuses of Lin⁻ HSC-injected eyes, as well as the neuronal cell-containing INL and ONL, were significant at all time points measured when rescued and non-rescued eyes were compared (FIGS. 16(B and C)). This effect was quantified by measuring the total length of the vasculature (FIG. 16(D)) and counting the number of DAPI-positive cell nuclei observed in the ONL (FIG. 16(E)). Simple linear-regression analysis was applied to the data at all time points.

A statistically significant correlation was observed between vascular rescue and neuronal (e.g., ONL thickness) rescue at P30 ($p<0.024$) and P60 ($p<0.034$) in the Lin⁻ HSC-injected eyes (FIG. 16(F)). The correlation remained high, although not statistically significant ($p<0.14$) at P180 when comparing Lin⁻ HSC-injected retinas to control cell-injected retinas (FIG. 16(F)). In contrast, control cell-injected retinas showed no significant correlation between the preservation of vasculature and ONL at any time point (FIG. 16(F)). These data demonstrate that intravitreal injection of Lin⁻ HSCs results in concomitant retinal vascular and neuronal rescue in retinas of rd1/rd1 mice. Injected cells were not observed in the ONL or any place other than within, or in close proximity to, retinal blood vessels.

Functional Rescue of Lin⁻ HSC-Injected rd/rd Retinas.

Figure 17:
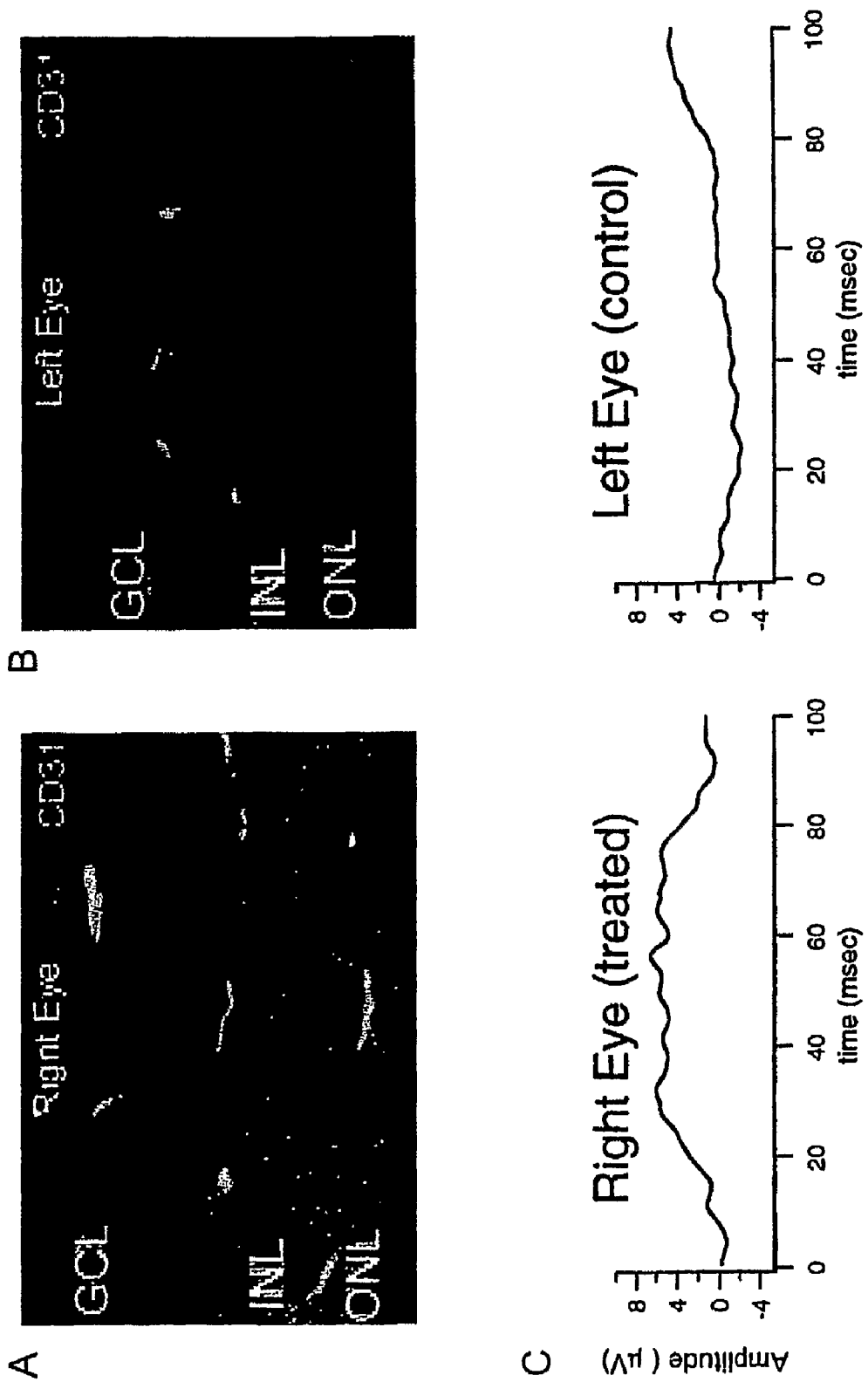
FIG. 17 demonstrates that retinal function is rescued by Lin⁻HSC injection. Electroretinographic (ERG) recordings were used to measure the function of Lin⁻HSC or control cell (CD31⁻) injected retinas. (A and B), Representative cases of rescued and non-rescued retinas 2 months after injection. Retinal section of Lin⁻HSC injected right eye (A) and CD31⁻ control cell injected left eye (B) of the same animal are shown (green: CD31 stained vasculature, red: DAPI stained nuclei). (C), ERG results from the same animal shown in (A) and (B).

Electroretinograms (ERGs) were performed on mice 2 months after injection of control cells or murine Lin⁻ HSCs (FIG. 17). Immunohistochemical and microscopic analysis was done with each eye following ERG recordings to confirm that vascular and neuronal rescue had occurred. Representative ERG recordings from treated, rescued and control, non-rescued eyes show that in the rescued eyes, the digitally subtracted signal (treated minus untreated eyes) produced a clearly detectable signal with an amplitude on the order of 8-10 microvolts (FIG. 17). Clearly, the signals from both eyes are severely abnormal. However, consistent and detectable ERGs were recordable from the Lin⁻ HSC-treated eyes. In all cases the ERG from the control eye was non-detectable. While the amplitudes of the signals in rescued eyes were considerably lower than normal, the signals were consistently observed whenever there was histological rescue and were on the order of magnitude of those reported by other, gene based, rescue studies. Overall these results are demonstrate of some degree of functional rescue in the eyes treated with the Lin⁻ HSCs.

Rescued rd/rd Retinal Cell Types are Predominantly Cones.

Figure 25:
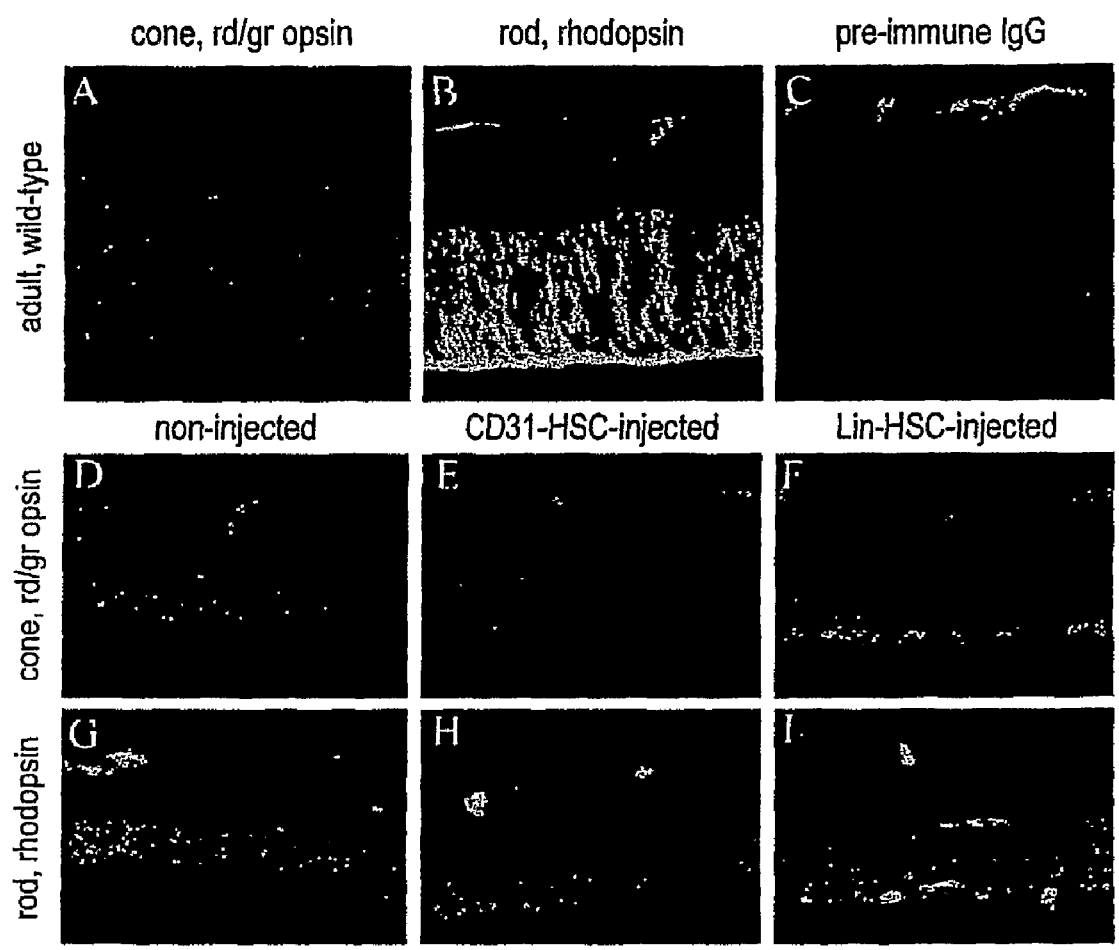
FIG. 25 shows rescued photoreceptors in rd1 mouse outer nuclear layer (ONL) following intravitreal injection of Lin-HSC are predominantly cones. A small percentage of photoreceptors in the wild type mouse retina (upper panel) were cones as evidenced by expression of red/green cone opsin (A) while most cells of the ONL were positive for rod specific rhodopsin (B). Retinal vasculature autofluoresces with pre-immune serum (C) but nuclear layers were completely negative for staining with rod or cone-specific opsins. Rd/rd mouse retinas (lower panels) had a diminished inner nuclear layer and a nearly completely atrophic ONL, both of which were negative for cone (D) or rod (Panel G) opsin. Control, CD31-HSC treated eyes are identical to non-injected rd/rd retinas, without any staining for cone (E) or rod (H) opsin. Lin-HSC treated contralateral eyes exhibited a markedly reduced, but clearly present ONL that is predominantly comprised of cones, as evidenced by positive immunoreactivity for cone red/green opsin (F). A small number of rods were also observed (I).

Rescued and non-rescued retinas were analyzed immunohistochemically with antibodies specific for rod or cone opsin. The same eyes used for the ERG recordings presented in FIG. 17 were analyzed for rod or cone opsin. In wild type mouse retinas, less than about 5% of photoreceptors present are cones (Soucy et al. 1998, *Neuron* 21: 481-493) and the immunohistochemical staining patterns observed with red/green cone opsin as shown in FIG. 25(A) or rod rhodopsin as shown in FIG. 25(B), were consistent with this percentage of cone cells. When wild type retinas were stained with pre-immune IgG, no staining was observed anywhere in the neurosensory retinas other than autoflouresence of the blood vessels (FIG. 25(C)). Two months after birth, retinas of non-injected rd/rd mice had an essentially atrophic outer nuclear layer that does not exhibit any staining with antibodies to red green cone opsin (FIG. 25(D)) or rhodopsin (FIG. 25(G)). Eyes injected with control, CD31-HSC also did not stain positively for the presence of either cone (FIG. 25(E))) or rod (FIG. 25(H)) opsin. In contrast, contralateral eyes injected with Lin-HSC had about 3 to about 8 rows of nuclei in a preserved outer nuclear layer; most of these cells were positive for cone opsin (FIG. 25(F)) with approximately 1-3% positive for rod opsin (FIG. 25(I)). Remarkably, this is nearly the reverse of what is ordinarily observed in the normal mouse retina, which is rod-dominated. These data demonstrate that the injection of Lin-HSC preserves cones for extended periods of time during which they would ordinarily degenerate.

Human Bone Marrow (hBM)-Derived Lin⁻ HSCs also Rescue Degenerating Retinas.

Figure 18:
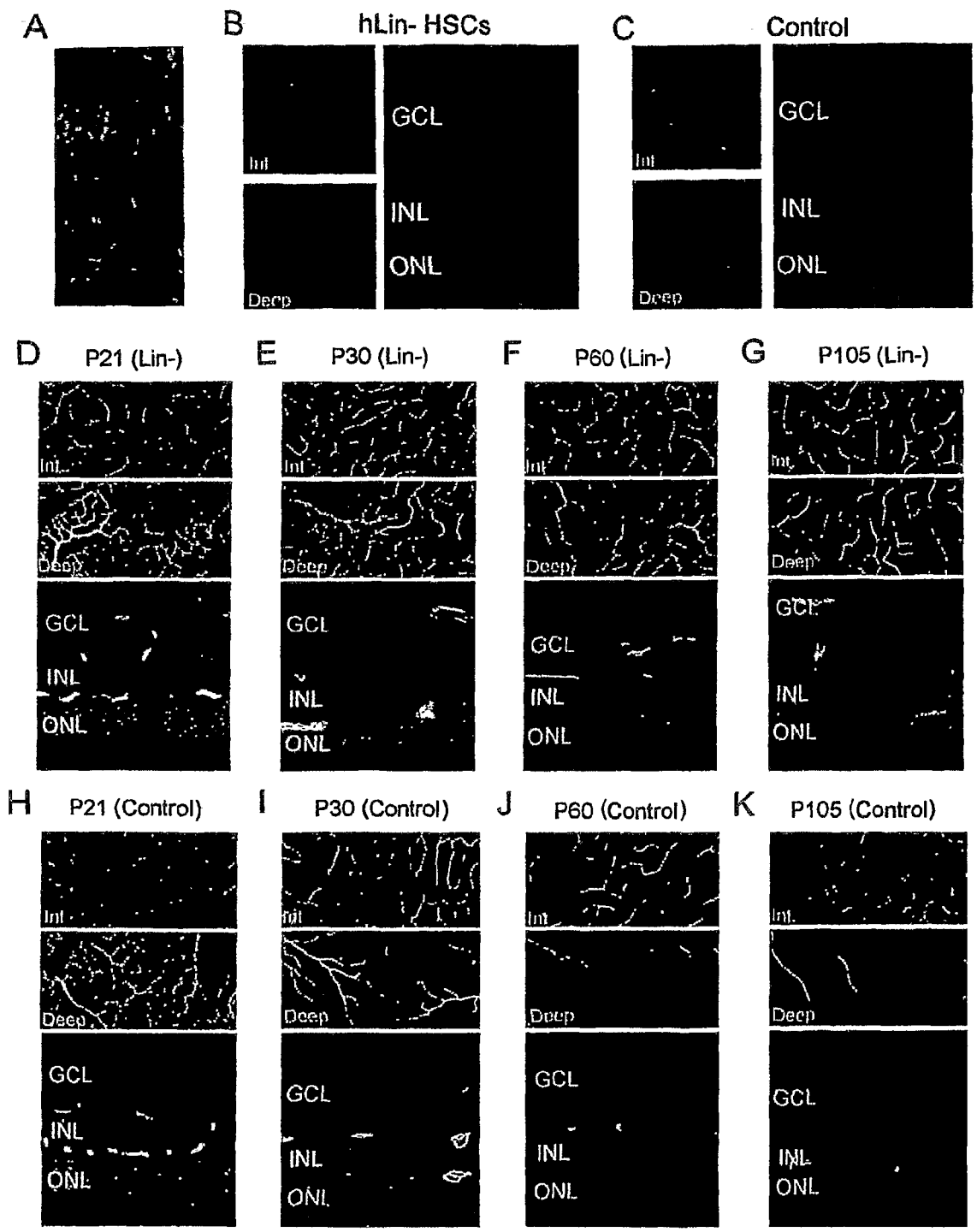
FIG. 18 shows that a population of human bone marrow cells can rescue degenerating retinas in the rd1 mouse (A-C). The rescue is also observed in another model of retinal degeneration, rd10 (D-K). A, human Lin⁻HSCs (hLin⁻HSCs) labeled with green dye can differentiate into retinal vascular cells after intravitreal injection into C3SnSmn.CB17-Prkdc SCID mice. (B and C), Retinal vasculature (left panels; upper: intermediate plexus, lower: deep plexus) and neural cells (right panel) in hLin⁻HSC injected eye (B) or contralateral control eye (C) 1.5 months after injection. (D-K), Rescue of rd10 mice by Lin⁻HSCs (injected at P6). Representative retinas at P21 (D: Lin⁻HSCs, H: control cells), P30 (E: Lin⁻HSCs, I: control cells), P60 (F: Lin⁻HSCs, J: control cells), and P105 (G: Lin⁻HSCs, K: control cells) are shown (treated and control eyes are from the same animal at each time point). Retinal vasculature (upper image in each panel is the intermediate plexus; the middle image in each panel is the deep plexus) was stained with CD31 (green) and Collagen IV (red). The lower image in each panel shows a cross section made from the same retina (red: DAPI, green: CD31).

Lin⁻ HSCs isolated from human bone marrow behave similarly to murine Lin⁻ HSCs. Bone marrow was collected from human donors and the Lin⁺ HSCs were depleted, producing a population of human Lin⁻ HSCs (hLin⁻ HSCs). These cells were labeled ex-vivo with fluorescent dye and injected into C3SnSmn.CB17-Prkdc SCID mouse eyes. The injected hLin⁻ HSCs migrated to, and targeted, sites of retinal angiogenesis in a fashion identical to that observed when murine Lin⁻ HSCs were injected (FIG. 18(A)). In addition to the vascular targeting, the human Lin⁻ HSCs also provided a robust rescue effect on both the vascular and neuronal cell layers of the rd1/rd1 mice (FIGS. 18(B and C)). This observation confirms the presence of cells in human bone marrow that target retinal vasculature and can prevent retinal degeneration.

Lin⁻ HSCs have Vasculo- and Neurotrophic Effects in the rd10/rd10 Mouse.

While the rd1/rd1 mouse is the most widely used and best characterized model for retinal degeneration (Chang et al. 2002, *Vision Res.* 42:517-525), the degeneration is very rapid and in this regard differs from the usual, slower time course observed in the human disease. In this strain, photoreceptor cell degeneration begins around P8, a time when the retinal vasculature is still rapidly expanding (FIG. 15). Subsequent degeneration of the deep retinal vasculature occurs even while the intermediate plexus is still forming and, thus, the retinas of rd1/rd1 mice never completely develops, unlike that observed in most humans with this disease. An rd10 mouse model, which has a slower time course of degeneration and more closely resembles the human retinal degenerative condition, was used to investigate Lin⁻ HSC-mediated vascular rescue. In the rd10 mouse, photoreceptor cell degeneration begins around P21 and vascular degeneration begins shortly thereafter.

Since normal neurosensory retinal development is largely complete by P21, the degeneration is observed to start after the retina has completed differentiation and in this way is more analogous to human retinal degenerations than the rd1/rd1 mouse model. Lin⁻ HSCs or control cells from rd10 mice were injected into P6 eyes and the retinas were evaluated at varying time points. At P21 the retinas from both Lin⁻ HSC and control cell-injected eyes appeared normal with complete development of all vascular layers and normal development of the INL and ONL (FIGS. 18(D and H)). At approximately P21 the retinal degeneration began and progressed with age. By P30, the control cell-injected retinas exhibited severe vascular and neuronal degeneration (FIG. 18(I)), while the Lin⁻ HSC-injected retinas maintained nearly normal vascular layers and photoreceptor cells (FIG. 18(E)). The difference between the rescued and non-rescued eyes was more pronounced at later time points (compare FIGS. 18(F and G) to 18(J and K)). In the control treated eyes, the progression of vascular degeneration was very clearly observed by immunohistochemical staining for CD31 and collagen IV (FIG. 18(I-K)). The control-treated eyes were nearly completely negative for CD31, whereas collagen IV-positive vascular "tracks" remained evident, indicating that vascular regression, rather than incomplete vascular formation, had occurred. In contrast, Lin⁻HSC-treated eyes had both CD31 and collagen IV-positive vessels that appeared very similar to normal, wild-type eyes (compare FIGS. 18(F and I)).

Gene Expression Analysis of rd/rd Mouse Retinas after Lin⁻ HSC Treatment.

Figure 19:
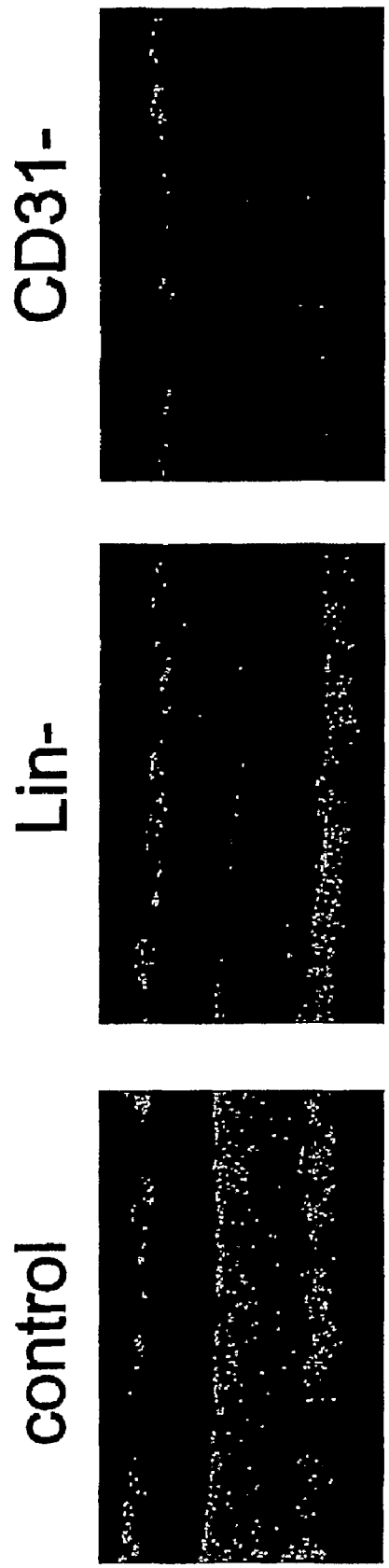
FIG. 19 demonstrates that crystallin αA is up regulated in rescued outer nuclear layer cells after treatment with Lin⁻ HSCs but not in contralateral eyes treated with control cells. Left panel; IgG control in rescued retina, Middle panel; crystallin αA in rescued retina, Right panel; crystallin αA in non-rescued retina.

Large scale genomics (microarray analysis) was used to analyze rescued and non-rescued retinas to identify putative mediators of neurotrophic rescue. Gene expression in rd1/rd1 mouse retinas treated with Lin⁻ HSCs was compared to uninjected retinas as well as retinas injected with control cells (CD31⁻). These comparisons each were performed in triplicate. To be considered present, genes were required to have expression levels at least 2-fold higher than background levels in all three triplicates. Genes that were upregulated 3-fold in Lin⁻ HSC-protected retinas compared to control cell-injected and non-injected rd/rd mouse retinas are shown in FIG. 20, panels A and B. Coefficient of variance (COV) levels were calculated for the expressed genes by dividing the standard deviation by the mean expression level of each cRNA replicate. In addition, the correlation between expression levels and noise variance was calculated by correlating the mean and standard deviation (SD). A correlation between gene expression level and standard deviation for each gene was obtained, allowing background levels and reliable expression level thresholds to be determined. As a whole, the data fell well within acceptable limits (Tu et al. 2002, *Proc. Natl. Acad. Sci. USA* 99: 14031-14036). The genes that are discussed individually, below, exhibited expression levels above these critical expression levels. Paired "t-test" values for the discussed genes were also determined. In each case, p-values are reasonable (near or below 0.05), which demonstrates that there are similarities between replicates and probable significant differences between the different test groups. Many of the significantly upregulated genes, including MAD and Ying Yang-1 (YY-1) (Austen et al. 1997, *Curr. Top. Microbiol. Immunol.* 224: 123-130.), encode proteins with functions involving the protection of cells from apoptosis. A number of crystallin genes, which have sequence homology and similar functions to known heat-shock proteins involving protection of cells from stress, were also upregulated by Lin-HSC treatment. Expression of α-crystallin was localized to the ONL by immunohistochemical analysis (FIG. 19). FIG. 19 shows that crystallin αA is upregulated in rescued outer nuclear layer cells after treatment with Lin⁻ HSCs but not in contralateral eyes treated with control cells. The left panel shows IgG staining (control) in rescued retina. The middle panel shows crystallin αA in a rescued retina. The right panel shows crystallin αA in non-rescued retina.

Messenger RNA from rd1/rd1 mouse retinas rescued with human Lin⁻ HSCs were hybridized to human specific Affymetrix U133A microarray chips. After stringent analysis, a number of genes were found whose mRNA expression was human specific, above background, and significantly higher in the human Lin⁻ HSC rescued retinas compared to the murine Lin⁻ HSC rescued retinas and the human control cell-injected non-rescued retinas (FIG. 20, panel C). CD6, a cell adhesion molecule expressed at the surface of primitive and newly differentiated CD34+ hematopoietic stem cells, and interferon alpha 13, another gene expressed by hematopoietic stem cells, were both found by the microarray bioinformatics technique, validating the evaluation protocol. In addition, several growth factors and neurotrophic factors were expressed above background by human Lin⁻ HSC rescued mouse retina samples (FIG. 20, panel D).

Markers for lineage-committed hematopoietic cells were used to negatively select a population of bone marrow-derived Lin⁻ HSC containing EPC. While the sub-population of bone marrow-derived Lin⁻ HSC that can serve as EPC is not characterized by commonly used cell surface markers, the behavior of these cells in developing or injured retinal vasculature is entirely different than that observed for Lin⁺ or adult endothelial cell populations. These cells selectively target to sites of retinal angiogenesis and participate in the formation of patent blood vessels.

Inherited retinal degenerative diseases are often accompanied by loss of retinal vasculature. Effective treatment of such diseases requires restoration of function as well as maintenance of complex tissue architecture. While several recent studies have explored the use of cell-based delivery of trophic factors or stem cells themselves, some combination of both may be necessary. For example, use of growth factor therapy to treat retinal degenerative disease resulted in unregulated overgrowth of blood vessels resulting in severe disruption of the normal retinal tissue architecture. The use of neural or retinal stem cells to treat retinal degenerative disease may reconstitute neuronal function, but a functional vasculature will also be necessary to maintain retinal functional integrity. Incorporation of cells from a Lin⁻ HSC population into the retinal vessels of rd/rd mice stabilized the degenerative vasculature without disrupting retinal structure. This rescue effect was also observed when the cells were injected into P15 rd/rd mice. Since vascular degeneration begins on P16 in rd/rd mice, this observation expands the therapeutic window for effective Lin⁻ HSC treatment. Retinal neurons and photoreceptors are preserved and visual function is maintained in eyes injected with the Lin⁻ HSC cells.

Adult bone marrow-derived Lin⁻ HSCs exert profound vasculo- and neurotrophic effects when injected intravitreally into mice with retinal degenerative disease. This rescue effect persists for up to 6 months after treatment and is most efficacious when the Lin⁻ HSCs are injected prior to complete retinal degeneration (up to 16 days after birth in mice that ordinarily exhibit complete retinal degeneration by 30 days postnatally). This rescue is observed in two mouse models of retinal degeneration and, remarkably, can be accomplished with adult human bone marrow-derived HSCs when the recipient is an immunodeficient rodent with retinal degeneration (e.g., the SCID mouse) or when the donor is a mouse with retinal degeneration. While several recent reports have described a partial phenotypic rescue in mice or dogs with retinal degeneration after viral based gene rescue with the wild type gene (Ali, et al. 2000, *Nat Genet* 25:306-310; Takahashi et al. 1999, *J. Virol.* 73:7812-7816; Acland et al. 2001, *Nat. Genet.* 28:92-95.), the present invention is the first generic cell-based therapeutic effect achieved by vascular rescue. Thus, the potential utility of such an approach in treating a group of diseases (e.g., retinitis pigmentosa) with over 100 known associated mutations is more practical than creating individual gene therapies to treat each known mutation.

The precise molecular basis of the neurotrophic rescue effect remains unknown, but is observed only when there is concomitant vascular stabilization/rescue. The presence of injected stem cells, per se, is not sufficient to generate a neurotrophic rescue and the clear absence of stem cell-derived neurons in the outer nuclear layer rules out the possibility that the injected cells are transforming into photoreceptors. Data obtained by microarray gene expression analysis demonstrated a significant up-regulation of genes known to have anti-apoptotic effects. Since most neuronal death observed in retinal degenerations is by apoptosis, such protection may be of great therapeutic benefit in prolonging the life of photoreceptors and other neurons critical to visual function in these diseases. C-myc is a transcription factor that participates in apoptosis by upregulation of various downstream apoptosis-inducing factors. C-myc expression was increased 4.5 fold in rd/rd mice over wild-type indicating potential involvement in the photoreceptor degeneration observed in the rd1/rd1 mouse. Mad1 and YY-1, two genes dramatically upregulated in Lin⁻HSC-protected retinas (FIG. 20, panel A), are known to suppress the activity of c-myc, thus inhibiting c-myc induced apoptosis. Overexpression of Mad1 has also been shown to suppress Fas-induced activation of caspase-8, another critical component of the apoptotic pathway. Upregulation of these two molecules may play a role in protection of the retina from vascular and neural degeneration by preventing the initiation of apoptosis that normally leads to degeneration in rd/rd mice.

Another set of genes that were greatly upregulated in Lin⁻ HSC protected retinas includes members of the crystallin family (FIG. 20, panel B).

Similar to heat-shock and other stress-induced proteins, crystallins may be activated by retinal stress and provide a protective effect against apoptosis. Abnormally low expression of crystallin αA is correlated with photoreceptor loss in a rat model of retinal dystrophy and a recent proteomic analysis of the retina in the rd/rd mouse demonstrated induction of crystallin upregulation in response to retinal degeneration. Based on our microarray data of EPC-rescued rd/rd mouse retinas, upregulation of crystallins appear to play a key role in EPC mediated retinal neuroprotection.

Genes such as c-myc, Mad1, Yx-1 and the crystallins are likely to be downstream mediators of neuronal rescue. Neurotrophic agents can regulate anti-apoptotic gene expression, although our microarray analysis of retinas rescued with mouse stem cells did not demonstrate induction of increased levels of known neurotrophic factors. Analysis of human bone marrow-derived stem cell-mediated rescue with human specific chips did, on the other hand, demonstrate low, but significant increases in the expression of multiple growth factor genes.

The upregulated genes include several members of the fibroblast growth factor family and otoferlin. Mutations in the otoferlin gene are associated with genetic disorders leading to deafness due to auditory neuropathy. It is possible that otoferlin production by injected Lin⁻HSCs contributes to the prevention of retinal neuropathy as well. Historically, it has long been assumed that vascular changes observed in patients and animals with retinal degeneration were secondary to decreased metabolic demand as the photoreceptors die. The present data indicate that, at least for mice with inherited retinal degeneration, preserving normal vasculature can help maintain components of the outer nuclear layer as well.

Recent reports in the literature would support the concept that tissue-specific vasculature has trophic effects that go beyond that expected from simply providing vascular "nourishment." For example, liver endothelial cells can be induced to produce, after VEGFR1 activation, growth factors critical to hepatocyte regeneration and maintenance in the face of hepatic injury (LeCouter et al. 2003, Science 299:890-893). Similar indicative interactions between vascular endothelial cells and adjacent hepatic parenchymal cells are reportedly involved in liver organogenesis, well before the formation of functional blood vessels. Endogenous retinal vasculature in individuals with retinal degeneration may not facilitate so dramatic a rescue, but if this vasculature is buttressed with endothelial progenitors derived from bone marrow hematopoietic stem cell populations, they may make the vasculature more resistant to degeneration and at the same time facilitate retinal neuronal, as well as vascular, survival. In humans with retinal degeneration, delaying the onset of complete retinal degeneration may provide years of additional sight. The animals treated with Lin⁻HSCs had significant preservation of an ERG, which may be sufficient to support vision.

Clinically, it is widely appreciated that there may be substantial loss of photoreceptors and other neurons while still preserving functional vision. At some point, the critical threshold is crossed and vision is lost. Since nearly all of the human inherited retinal degenerations are of early, but slow, onset, an individual with retinal degeneration can be identified and treated intravitreally with a graft of autologous bone marrow stem cells of the invention to delay retinal degeneration and concomitant loss of vision. To enhance targeting and incorporation of the stem cells of the invention, the presence of activated astrocytes is desirable (Otani et al. 2002, Nat. Med 8: 1004-1010); this can be accomplished by early treatment when there is an associated gliosis, or by using a laser to stimulate local proliferation of activated astrocytes. Optionally, ex vivo transfection of the stem cells with one or more neurotrophic substances prior to intraocular injection can be used to enhance the rescue effect. This approach can be applied to the treatment of other visual neuronal degenerative disorders, such as glaucoma, in which there is retinal ganglion cell degeneration.

The Lin⁻ HSC populations from adult bone marrow contain a population of EPC that can promote angiogenesis by targeting reactive astrocytes and incorporate into an established template without disrupting retinal structure. The Lin⁻ HSC also provide a long-term neurotrophic rescue effect in eyes suffering from retinal degeneration. In addition, genetically modified, autologous Lin⁻ HSC compositions containing EPC can be transplanted into ischemic or abnormally vascularized eyes and can stably incorporate into new vessels and neuronal layers and continuously deliver therapeutic molecules locally for prolonged periods of time. Such local delivery of genes that express pharmacological agents in physiologically meaningful doses represents a new paradigm for treating currently untreatable ocular diseases.

Photoreceptors in the normal mouse retina, for example, are predominantly rods, but the outer nuclear layer observed after rescue with Lin-HSCs of the invention contained predominantly cones. Most inherited human retinal degenerations occur as a result of primary rod-specific defects, and loss of the cones is believed to be secondary to rod dysfunction, which is likely related to the loss of some trophic factor expressed by rods.

EXAMPLES

Example 1

Cell Isolation and Enrichment; Preparation of Murine Lin⁻ HSC Populations A and B General Procedure. All in vivo evaluations were performed in accordance with the NIH Guide for the Care and Use of Laboratory Animals, and all evaluation procedures were approved by The Scripps Research Institute (TSRI, La Jolla, Calif.) Animal Care and Use Committee. Bone marrow cells were extracted from B6.129S7-Gtrosa26, Tie-2GFP, ACTbE-GFP, FVB/NJ (rd/rd mice) or Balb/cBYJ adult mice (The Jackson Laboratory, ME).

Monocytes were then separated by density gradient separation using HISTOPAQUE® polysucrose gradient (Sigma, St. Louis, Mo.) and labeled with biotin conjugated lineage panel antibodies (CD45, CD3, Ly-6G, CD11, TER-119, Pharmingen, San Diego, Calif.) for Lin$^-$ selection in mice. Lineage positive (Lin$^+$) cells were separated and removed from Lin$^-$ HSC using a magnetic separation device (AU-TOMACS™ sorter, Miltenyi Biotech, Auburn, Calif.). The resulting Lin$^-$ HSC population, containing endothelial progenitor cells was further characterized using a FACS™ Calibur flow cytometer (Becton Dickinson, Franklin Lakes, N.J.) using the following antibodies: PE-conjugated-Sca-1, c-kit, KDR, and CD31 (Pharmingen, San Diego, Calif.). Tie-2-GFP bone marrow cells were used for the characterization of Tie-2.

To harvest adult mouse endothelial cells, mesenteric tissue was surgically removed from ACTbEGFP mouse and placed in collagenase (Worthington, Lakewood, N.J.) to digest the tissue, followed by filtration using a 45 μm filter. Flow-through was collected and incubated with Endothelial Growth Media (Clonetics, San Diego, Calif.). Endothelial characteristics were confirmed by observing morphological cobblestone appearance, staining with CD31 mAb (Pharmingen) and examining cultures for the formation of tube-like structures in MATRIGEL™ matrix (Beckton Dickinson, Franklin Lakes, N.J.).

Murine Lin$^-$ HSC Population A. Bone marrow cells were extracted from ACTbEGFP mice by the General Procedure described above. The Lin$^-$ HSC cells were characterized by FACS flow cytometry for CD31, c-kit, Sca-1, Flk-1, and Tie-2 cell surface antigen markers. The results are shown in FIG. 1(c). About 81% of the Lin$^-$ HSC exhibited the CD31 marker, about 70.5% of the Lin$^-$ HSC exhibited the c-kit marker, about 4% of the Lin$^-$ HSC exhibited the Sca-1 marker, about 2.2% of the Lin$^-$ HSC exhibited the Flk-1 marker and about 0.91% of the Lin$^-$ HSC cell exhibited the Tie-2 marker. In contrast, the Lin$^+$ HSC that were isolated from these bone marrow cells had a significantly different cell marker profile (i.e., CD31: 37.4%; c-kit: 20%; Sca-1: 2.8%; Flk-: 0.05%).

Murine Lin$^-$ HSC Population B. Bone marrow cells were extracted from Balb/C, ACTbEGFP, and C3H mice by the General Procedure described above. The Lin$^-$ HSC cells were analyzed for the presence of cell surface markers (Sca-1, Flk-1/KDR, c-kit (CD117), CD34, CD31 and various integrins: $\alpha1, \alpha2, \alpha3, \alpha4, \alpha5, \alpha6, \alpha_L, \alpha_M \alpha_V, \alpha_{IIb}, \beta_1, \beta_2, \beta_3, \beta_5,$ and $\beta_7$). The results are shown in Table 2.

TABLE 2

Characterization of Lin$^-$ HSC Population B.

| Cell Marker | Lin$^-$ HSC |
|---|---|
| α1 | 0.10 |
| α2 | 17.57 |
| α3 | 0.22 |
| α4 | 89.39 |
| α5 | 82.47 |
| α6 | 77.70 |
| αL | 62.69 |
| αM | 35.84 |
| αX | 3.98 |
| αV | 33.64 |
| αIIb | 0.25 |
| β1 | 86.26 |
| β2 | 49.07 |
| β3 | 45.70 |
| β4 | 0.68 |
| β5 | 9.44 |
| β7 | 11.25 |
| CD31 | 51.76 |
| CD34 | 55.83 |
| Flk-1/KDR | 2.95 |
| c-kit (CD117) | 74.42 |
| Sca-1 | 7.54 |

Example 2

Intravitreal Administration of Cells in a Murine Model

An eyelid fissure was created in a mouse eyelid with a fine blade to expose the P2 to P6 eyeball. Lineage negative HSC Population A of the present invention (approximately $10^5$ cells in about 0.5 μl to about 1 μl of cell culture medium) was then injected intravitreally using a 33-gauge (Hamilton, Reno, N.V.) needled-syringe.

Example 3

EPC Transfection

Murine Lin$^-$ HSC (Population A) were transfected with DNA encoding the T2 fragment of TrpRS also enclosing a His$_6$ tag (SEQ ID NO: 1, FIG. 7) using FuGENE™ 6 Transfection Reagent (Roche, Indianapolis, Ind.) according to manufacturer's protocol. Lin$^-$ HSC cells (about $10^6$ cell per ml) were suspended in OPTI-MEM® medium (Invitrogen, Carlsbad, Calif.) containing stem cell factor (PeproTech, Rocky Hill, N.J.). DNA (about 1 μg) and FuGENE reagent (about 3 μl) mixture was then added, and the mixtures were incubated at about 37° C. for about 18 hours. After incubation, cells were washed and collected. The transfection rate of this system was approximately 17% as confirmed by FACS analysis. T2-TrpRS production was confirmed by western blotting. The amino acid sequence of His$_6$-tagged T2-TrpRS is shown as SEQ ID NO: 2, FIG. 8.

Example 4

Immunohistochemistry and Confocal Analysis

Mouse retinas were harvested at various time points and were prepared for either whole mounting or frozen sectioning. For whole mounts, retinas were fixed with 4% paraformaldehyde, and blocked in 50% fetal bovine serum (FBS) and 20% normal goat serum for one hour at ambient room temperature. Retinas were processed for primary antibodies and detected with secondary antibodies. The primaries used were: anti-Collagen IV (Chemicon, Temecula, Calif., anti-β-gal (Promega, Madison, Wis.), anti-GFAP (Dako Cytomation, Carpenteria, Calif.), anti-α-smooth muscle actin (α-SMA, Dako Cytomation). Secondary antibodies used were conjugated either to Alexa 488 or 594 fluorescent markers (Molecular Probes, Eugene, Oreg.). Images were taken using an MRC 1024 Confocal microscope (Bio-Rad, Hercules, Calif.). Three-dimensional images were created using LASERSHARP® software (Bio-Rad) to examine the three different layers of vascular development in the whole mount retina. The difference in GFP pixel intensity between enhanced GFP (eGFP) mice and GFAP/wtGFP mice, distinguished by confocal microscopy, was utilized to create the 3 dimensional images.

Example 5

In vivo Retinal Angiogenesis Quantification Assay in Mice

For T2-TrpRS analysis, the primary and deep plexus were reconstructed from the three dimensional images of mouse retinas. The primary plexus was divided into two categories: normal development, or halted vascular progression. The categories of inhibition of deep vascular development were construed based upon the percentage of vascular inhibition including the following criteria: complete inhibition of deep plexus formation was labeled "Complete", normal vascular development (including less than 25% inhibition) was labeled "Normal" and the remainder labeled "Partial." For the rd/rd mouse rescue data, four separate areas of the deeper plexus in each whole mounted retina was captured using a 10× lens. The total length of vasculature was calculated for each image, summarized and compared between the groups. To acquire accurate information, Lin− HSC were injected into one eye and Lin+ HSC into another eye of the same mouse. Non-injected control retinas were taken from the same litter.

Example 6

Adult Retinal Injury Murine Models

Laser and scar models were created using either a diode laser (150 mW, 1 second, 50 mm) or mechanically by puncturing the mouse retina with a 27 gauge needle. Five days after injury, cells were injected using the intravitreal method. Eyes were harvested from the mice five days later.

Example 7

Neurotrophic Rescue of Retinal Regeneration

Figure 9:
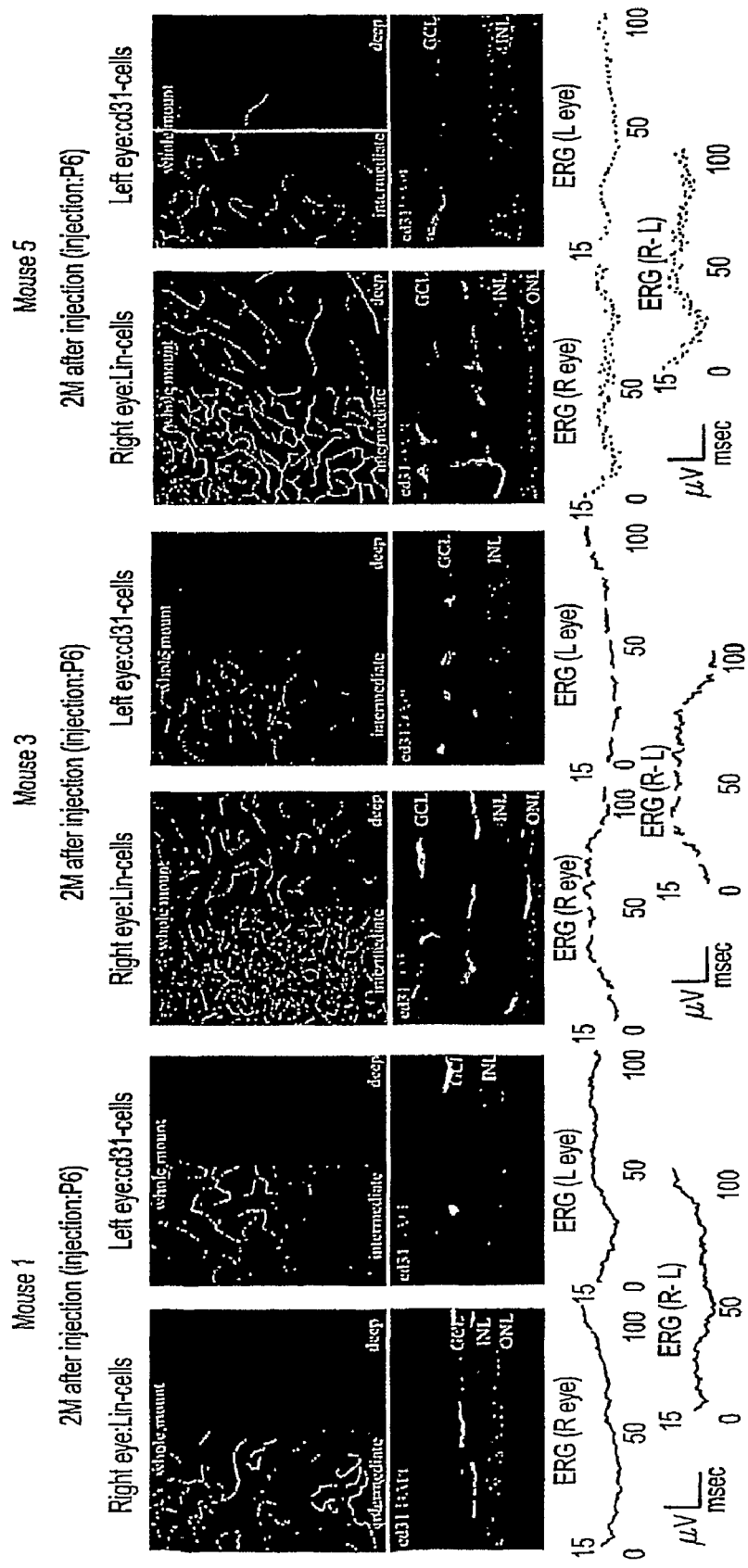
FIG. 9 illustrates photomicrographs and electroretinograms (ERG) of retinas from mice whose eyes were injected with the Lin⁻HSC and with Lin⁺HSC (controls).

Adult murine bone marrow derived lineage negative hematopoietic stem cells (Lin− HSC) have a vasculotrophic and neurotrophic rescue effect in a mouse model of retinal degeneration. Right eyes of 10-day old mice were injected intravitreally with about 0.5 microliters containing about $10^5$ Lin−HSC of the present invention and evaluated 2 months later for the presence of retinal vasculature and neuronal layer nuclear count. The left eyes of the same mice were injected with about the same number of Lin+HSC as a control, and were similarly evaluated. As shown in FIG. 9, in the Lin−HSC treated eyes, the retinal vasculature appeared nearly normal, the inner nuclear layer was nearly normal and the outer nuclear layer (ONL) had about 3 to about 4 layers of nuclei. In contrast, the contralateral Lin+HSC treated eye had a markedly atrophic middle retinal vascular layer, a completely atrophic outer retinal vascular layer; the inner nuclear layer was markedly atrophic and the outer nuclear layer was completely gone. This was dramatically illustrated in Mouse 3 and Mouse 5. In Mouse 1, there was no rescue effect and this was true for approximately 15% of the injected mice.

Figure 10:
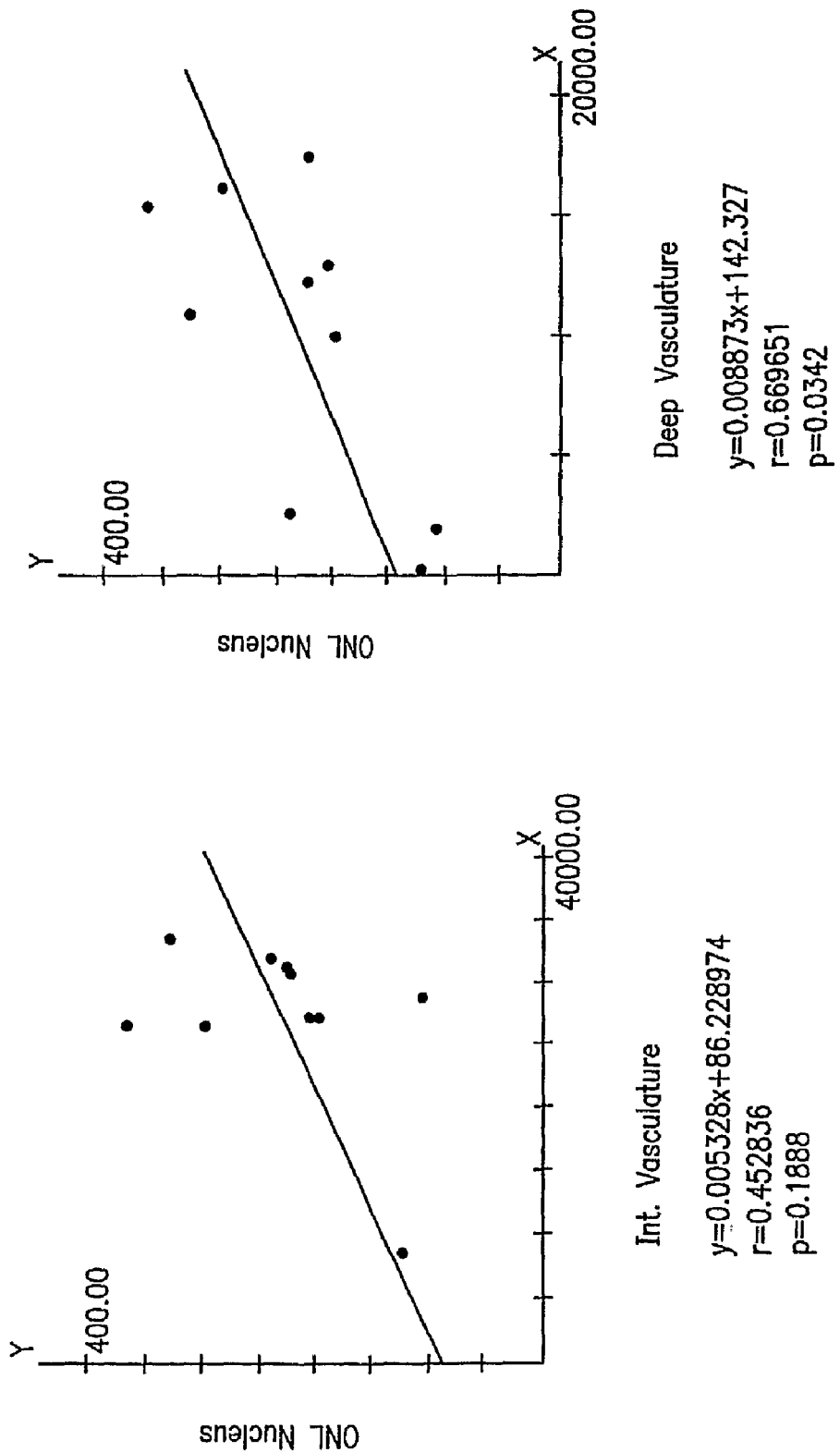
FIG. 10 depicts statistical plots showing a correlation between neuronal rescue (y-axis) and vascular rescue (x-axis) for both the intermediate (Int.) and deep vascular layers of rd/rd mouse eyes treated with Lin⁻HSC.

When visual function was assessed with electroretinograms (ERG), the restoration of a positive ERG was observed when both the vascular and neuronal rescue was observed (Mice 3 and 5). Positive ERG was not observed when there was no vascular or neuronal rescue (Mouse 1). This correlation between vascular and neurotrophic rescue of the rd/rd mouse eyes by the Lin−HSC of the present invention is illustrated by a regression analysis plot shown in FIG. 10. A correlation between neuronal (y-axis) and vascular (x-axis) recovery was observed for the intermediate vasculature type (r=0.45) and for the deep vasculature (r=0.67).

Figure 11:
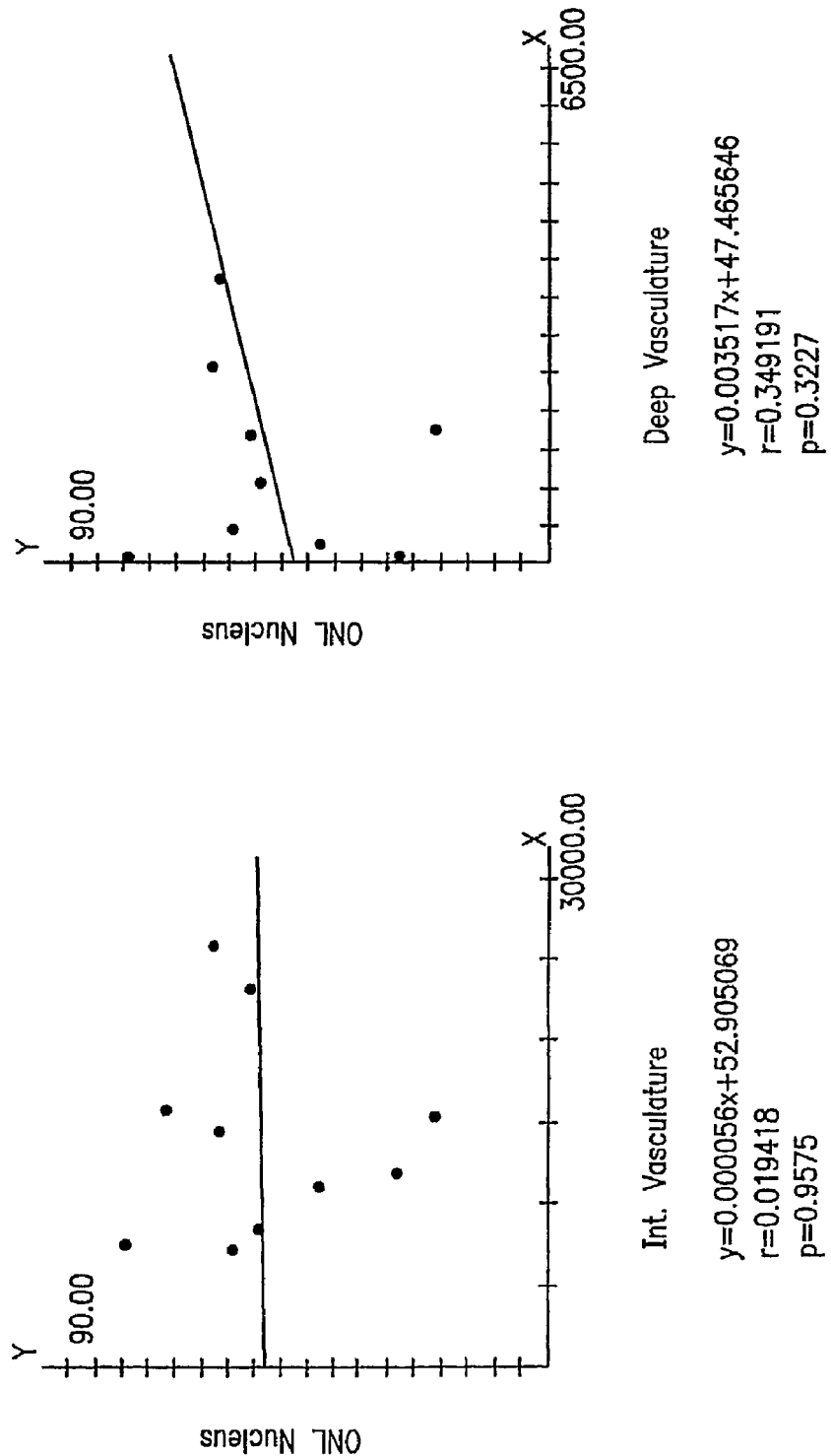
FIG. 11 depicts statistical plots showing no correlation between neuronal rescue (y-axis) and vascular rescue (x-axis) for rd/rd mouse eyes that were treated with Lin⁺HSC.
Figure 13:
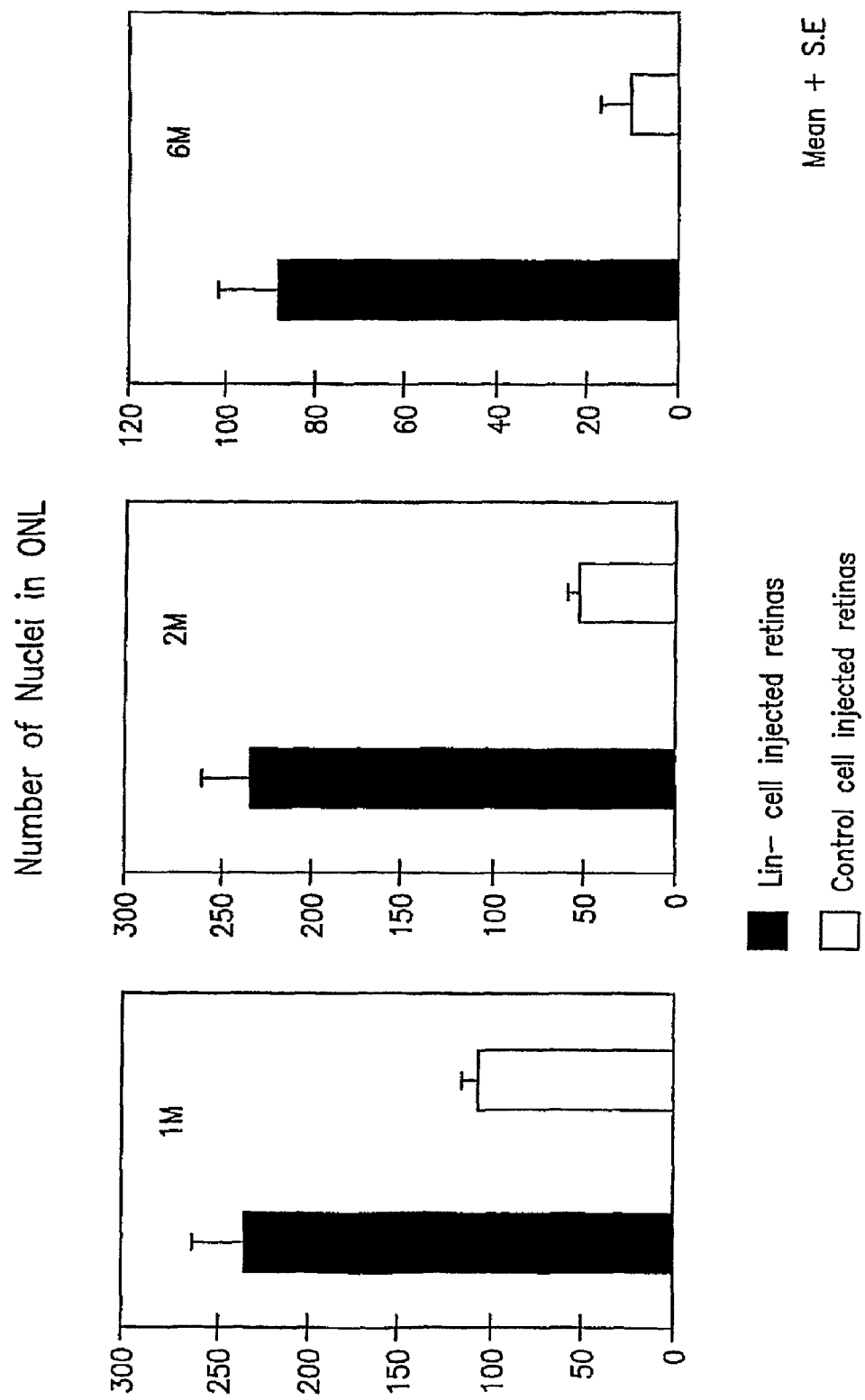
FIG. 13 includes three bar graphs of the number of nuclei in the outer neural layer (ONR) of rd/rd mice at 1 month (1M), 2 months (2M) and 6 months (6M), post-injection, and demonstrates a significant increase in the number of nuclei for eyes treated with Lin⁻HSC (dark bars) relative to control eyes treated with Lin⁺ HSC (light bars).
Figure 14:
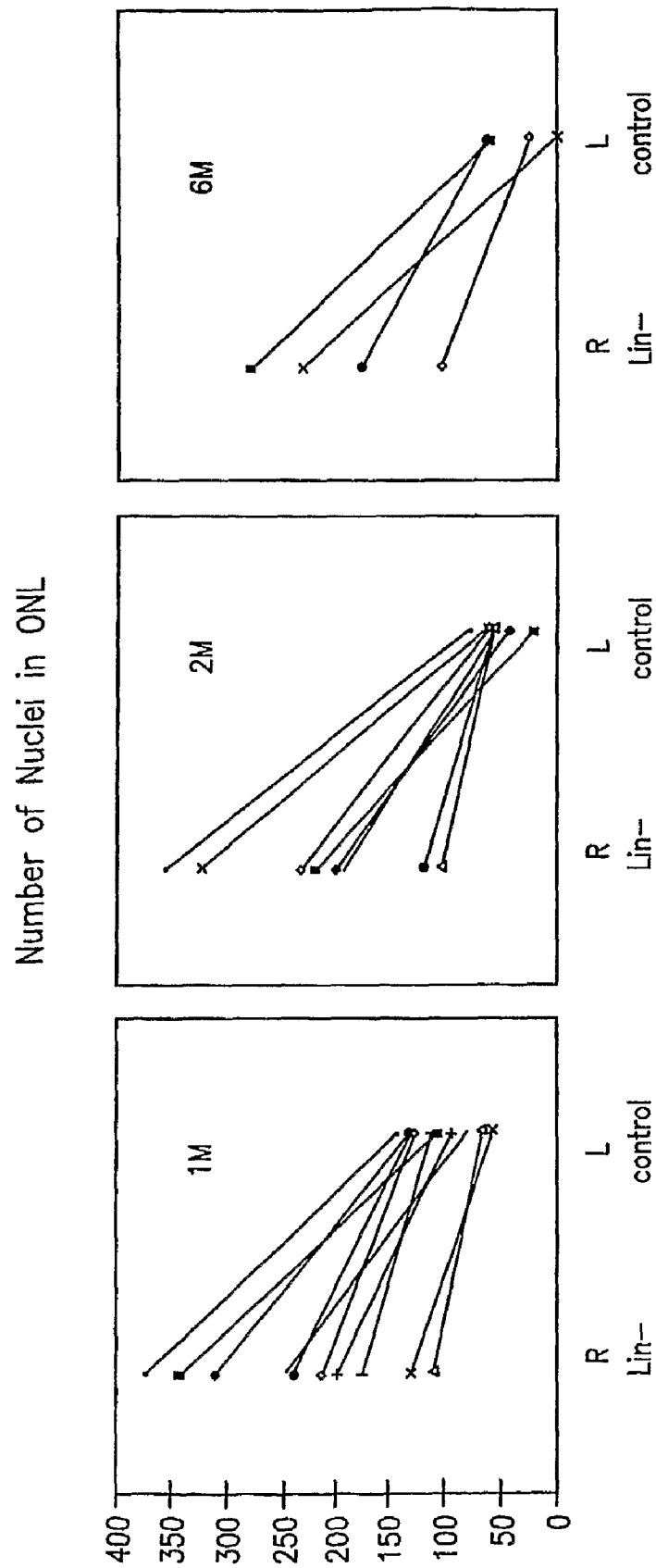
FIG. 14 depicts plots of the number of nuclei in the outer neural layer for individual rd/rd mice, comparing the right eye (R, treated with Lin⁻ HSC) relative to the left eye (L, control eye treated with Lin⁺ HSC) at time points (post injection) of 1 month (1M), 2 months (2M), and 6 months (6M); each line in a given plot compares the eyes of an individual mouse.

FIG. 11 shows the absence of any statistically significant correlation between vascular and neuronal rescue by Lin+ HSC. The vascular rescue was quantified and the data are presented in FIG. 12. Data for mice at 1 month (1M), 2 months (2M), and 6 months (6M), post-injection shown in FIG. 12, demonstrate that vascular length was significantly increased in eyes treated with the Lin−HSC of the present invention (dark bars) relative to the vascular length in untreated eyes from the same mouse (light bars), particularly at 1 month and 2 months, post-injection. The neurotrophic rescue effect was quantified by counting nuclei in the inner and outer nuclear layers about two months after injection of Lin− HSC or Lin+HSC. The results are presented in FIGS. 13 and 14.

Example 8

Human Lin− HSC Population

Bone marrow cells were extracted from healthy adult human volunteers by the General Procedure described above. Monocytes were then separated by density gradient separation using HISTOPAQUE® polysucrose gradient (Sigma, St. Louis, Mo.). To isolate the Lin− HSC population from human bone marrow mononuclear cells the following biotin conjugated lineage panel antibodies were used with the magnetic separation system (AUTOMACS™ sorter, Miltenyi Biotech, Auburn, Calif.): CD2, CD3, CD4, CD11a, Mac-1, CD14, CD16, CD19, CD33, CD38, CD45RA, CD64, CD68, CD86, CD235a (Pharmingen).

The human Lin− HSC population was further separated into two sub-populations based on CD133 expression. The cells were labeled with biotin-conjugated CD133 antibodies and separated into CD133 positive and CD133 negative sub-populations.

Example 9

Intravitreal Administration of Human and Murine Cells in Murine Models for Retinal Degeneration C3H/HeJ, C3SnSmn.CB17-Prkdc SCID, and rd10 mouse strains were used as retinal degeneration models. C3H/HeJ and C3SnSmn.CB17-Prkdc SCID mice (The Jackson Laboratory, Maine) were homozygous for the retinal degeneration 1 (rd1) mutation, a mutation that causes early onset severe retinal degeneration. The mutation is located in exon 7 of the Pde6b gene encoding the rod photoreceptor cGMP phosphodiesterase β subunit. The mutation in this gene has been found in human patients with autosomal recessive retinitis pigmentosa (RP). C3SnSmn.CB17-Prkdc SCID mice are also homozygous for the severe combined immune deficiency spontaneous mutation (Prkdc SCID) and were used for human cell transfer experiments. Retinal degeneration in rd10 mice is caused by a mutation in exon 13 of Pde6b gene. This is also a clinically relevant RP model with later onset and milder retinal degeneration than rd1/rd1). All evaluations were performed in accordance with the NIH Guide for the Care and Use of Laboratory Animals, and all procedures were approved by The Scripps Research Institute Animal Care and Use Committee.

An eyelid fissure was created in a mouse eyelid with a fine blade to expose the P2 to P6 eyeball. Lineage negative HSC cells for murine population A or human population C (approximately $10^5$ cells in about 0.5 µl to about 1 µl of cell culture medium) were then injected in the mouse eye intravitreally using a 33-gauge (Hamilton, Reno, N.V.) needled-syringe. To visualize the injected human cells, cells were labeled with dye (Cell tracker green CMFDA, Molecular Probes) before injection.

Retinas were harvested at various time points and fixed with 4% paraformaldehyde (PFA) and methanol followed by blocking in 50% FBS/20% NGS for one hour at room temperature. To stain retinal vasculature, retinas were incubated with anti-CD31 (Pharmingen) and anti-collagen IV (Chemicon) antibodies followed by Alexa 488 or 594 conjugated secondary antibodies (Molecular Probes, Eugene, Oreg.). The retinas were laid flat with four radial relaxing incisions to obtain a whole mount preparation. Images of vasculature in intermediate or deep retinal vascular plexuses (see Dorrell et al. 2002 *Invest Ophthalmol Vis. Sci.* 43:3500-3510) were obtained using a Radiance MP2100 confocal microscope and LASERSHARP® software (Biorad, Hercules, Calif.). For quantification of vasculature, four independent fields (900 µm×900 µm) were chosen randomly from the mid portion of the intermediate or deep vascular layer and the total length of vasculature was measured using LASERPIX® analyzing software (Biorad). The total lengths of these four fields in the same plexus were used for further analysis.

The flat-mounted retinas were re-embedded for cryostat sections. Retinas were placed in 4% PFA overnight followed by incubation with 20% sucrose. The retinas were embedded in optimal cutting temperature compound (OCT: Tissue-Tek; Sakura FineTech, Torrance, Calif.). Cryostat sections (10 µm) were re-hydrated in PBS containing the nuclear dye DAPI (Sigma-Aldrich, St. Louis, Mo.). DAPI-labeled nuclear images of three different areas (280 µm width, unbiased sampling) in a single section that contained optic nerve head and the entire peripheral retina were taken by confocal microscope. The numbers of the nuclei located in ONL of the three independent fields in one section were counted and summed up for analysis. Simple linear-regression analysis was performed to examine the relationship between the length of vasculature in the deep plexus and the number of cell nuclei in the ONL.

Following overnight dark-adaptation, mice were anesthetized by intraperitoneal injection of 15 µg/gm ketamine and 7 µg/gm xylazine. Electroretinograms (ERGs) were recorded from the corneal surface of each eye after pupil dilation (1% atropine sulfate) using a gold loop corneal electrode together with a mouth reference and tail ground electrode. Stimuli were produced with a Grass Photic Stimulator (PS33 Plus, Grass Instruments, Quincy, Mass.) affixed to the outside of a highly reflective Ganzfeld dome. Rod responses were recorded to short-wavelength (Wratten 47A; $\lambda$max=470 nm) flashes of light over a range of intensities up to the maximum allowable by the photic stimulator (0.668 cd-s/m$^2$). Response signals were amplified (CP511 AC amplifier, Grass Instruments), digitized (PCI-1200, National Instruments, Austin, Tex.) and computer-analyzed. Each mouse served as its own internal control with ERGs recorded from both the treated and untreated eyes. Up to 100 sweeps were averaged for the weakest signals. The averaged responses from the untreated eye were digitally subtracted from the responses from the treated eye and this difference in signal was used to index functional rescue.

Microarray analysis was used for evaluation of Lin$^-$ HSC-targeted retinal gene expression. P6 rd/rd mice were injected with either Lin$^-$ or CD31$^-$ HSCs. The retinas of these mice were dissected 40 days post-injection in RNase free medium (rescue of the retinal vasculature and the photoreceptor layer is obvious at this time point after injection). One quadrant from each retina was analyzed by whole mount to ensure that normal HSC targeting as well as vasculature and neural protection had been achieved. RNA from retinas with successful injections was purified using a TRIzol (Life Technologies, Rockville, Md.), phenol/chloroform RNA isolation protocol. RNA was hybridized to Affymetrix Mu74Av2 chips and gene expression was analyzed using GENESPRING® software (SiliconGenetics, Redwood City, Calif.). Purified human or mouse HSCs were injected intravitreally into P6 mice. At P45 the retinas were dissected and pooled into fractions of 1) human HSC-injected, rescued mouse retinas, 2) human HSC-injected, non-rescued mouse retinas, and 3) mouse HSC-injected, rescued mouse retinas for purification of RNA and hybridization to human-specific U133A Affymetrix chips. GENESPRING® software was used to identify genes that were expressed above background and with higher expression in the human HSC-rescued retinas. The probe-pair expression profiles for each of these genes were then individually analyzed and compared to a model of normal human U133A microarray experiments using dChip to determine human species specific hybridization and to eliminate false positives due to cross-species hybridization.

Figure 21:
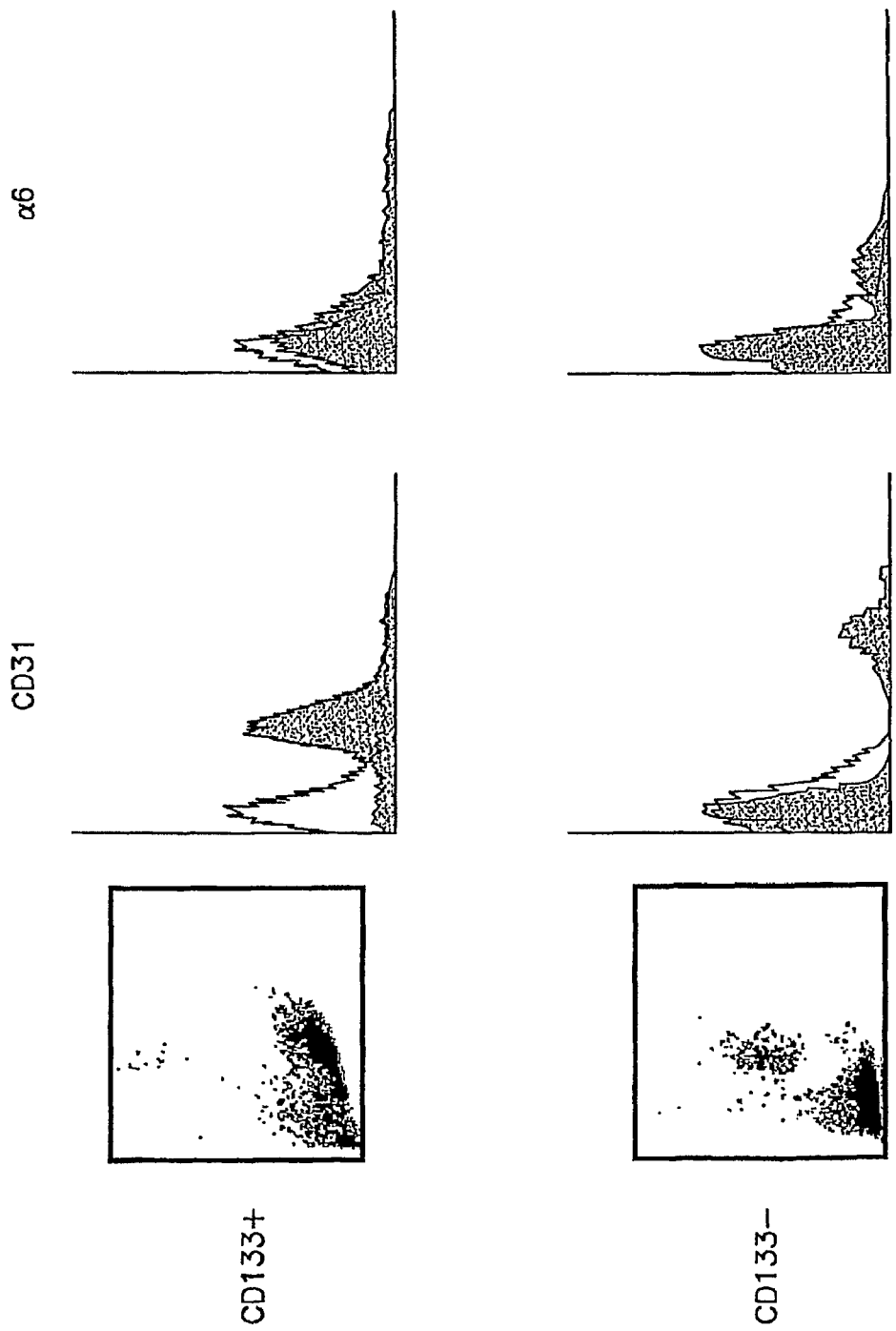
FIG. 21 illustrates the distribution of CD31 and integrin α6 surface antigens on CD133 positive (DC133⁺) and CD133 negative (CD133⁻) human Lin⁻HSC populations. The left panels show flow cytometry scatter plots. The center and right panels are histograms showing the level of specific antibody expression on the cell population. The Y axis represents the number of events and the X axis shows the intensity of the signal. A filled histogram shifted to the right of the outlined (control) histogram represents an increased fluorescent signal and expression of the antibody above background level.

FIG. 21 illustrates flow cytometry data comparing the expression of CD31 and integrin alpha 6 surface antigens on CD133 positive (CD133$^+$) and CD133 negative (CD133$^-$) human Lin$^-$ HSC populations of the present invention. The left panels show flow cytometry scatter plots. The center and right panels are histograms showing the level of specific antibody expression on the cell population. The Y axis represents the number of events and the X axis shows the intensity of the signal. The outlined histograms are isotype IgG control antibodies showing the level of non-specific background staining. The filled histograms show the level of specific antibody expression on the cell population. A filled histogram shifted to the right of the outlined (control) histogram represents an increased fluorescent signal and expression of the antibody above background level. Comparing the position of the peaks of the filled histograms between the two cell populations represents the difference in protein expression on the cells. For example, CD31 is expressed above background on both CD133$^+$ and CD133$^-$ cells of the invention; however, there are more cells expressing lower levels of CD31 in the CD133$^+$ cell population than there are in the CD133$^-$ population. From this data it is evident that CD31 expression varies between the two populations and that the alpha 6 integrin expression is largely limited to cells in the Lin$^-$ population, and thus may serve as a marker of cells with vasculo- and neurotrophic rescue function.

When the CD133 positive and CD133 negative Lin$^-$ HSC sub-population was intravitreally injected into the eyes of neonatal SCID mice, the greatest extent of incorporation into the developing vasculature was observed for the CD133 negative sub-population, which expresses both CD31 and integrin $\alpha$6 surface antigens (see FIG. 21, bottom). The CD133 positive sub-population, which does not express CD31 or integrin $\alpha$6 (FIG. 21, top) appears to target sites of peripheral ischemia-driven neovascularization, but not when injected into eyes undergoing angiogenesis.

Rescued and non-rescued retinas were analyzed immunohistochemically with antibodies specific for rod or cone opsin. The same eyes used for the ERG recordings presented in FIG. 17 were analyzed for rod or cone opsin. In wild type mouse retinas, less than 5% of photoreceptors present are cones (Soucy et al. 1998, *Neuron* 21: 481-493) and the immunohistochemical staining patterns observed with red/green cone opsin as shown in FIG. 25(A) or rod rhodopsin as shown in FIG. 25(B), were consistent with this percentage of cone cells. Antibodies specific for rod rhodopsin (rho4D2) were provided by Dr. Robert Molday of the University of British Columbia and used as described previously (Hicks et al. 1986, *Exp. Eye Res.* 42: 55-71). Rabbit antibodies specific for cone red/green opsin were purchased from Chemicon (AB5405) and used according to the manufacturer's instructions.

Example 10

Figure 22:
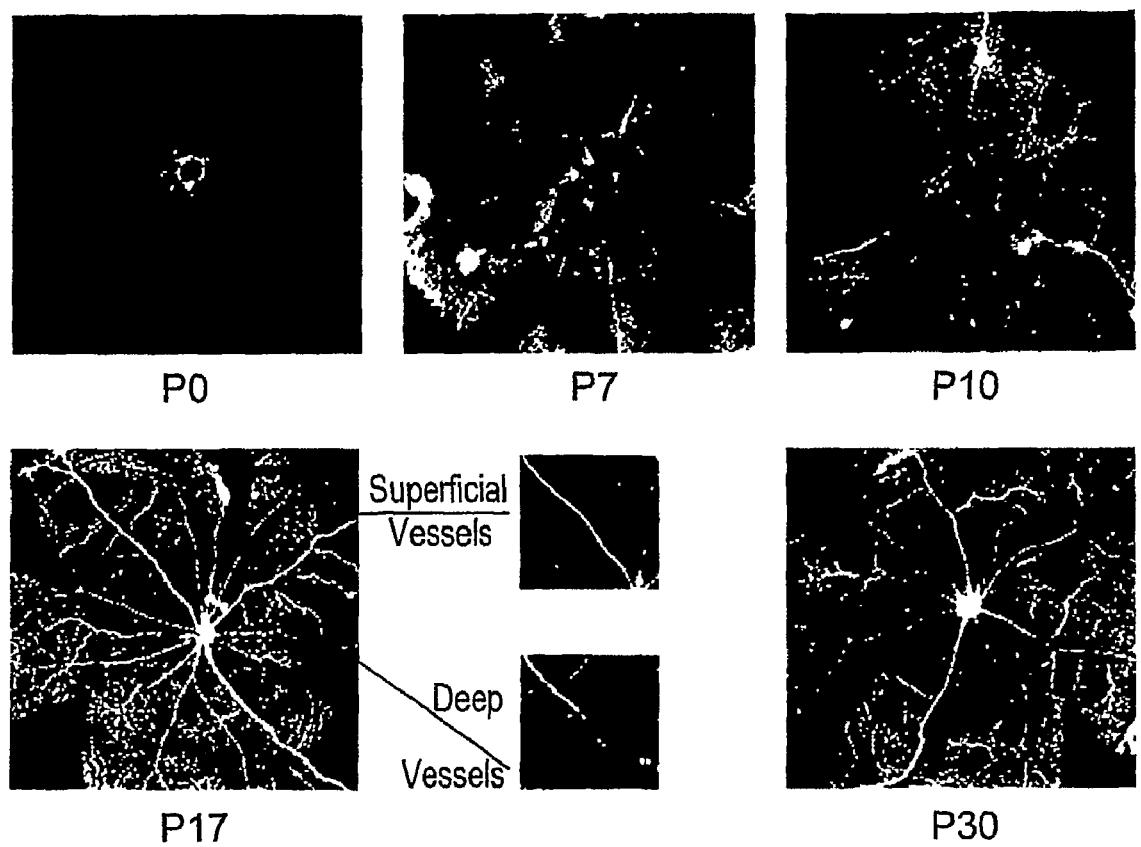
FIG. 22 illustrates postnatal retinal development in wild-type C57/B16 mice raised in normal oxygen levels (normoxia), at post natal days P0 through P30.

Intravitreal Administration of Murine Cells in Murine Models for Oxygen Induced Retinal Degeneration New born wild-type C57B16 mice were exposed to hyperoxia (75% oxygen) between postnatal days P7 to P12 in an oxygen-induced retinal degeneration (OIR) model. FIG. 22 illustrates normal postnatal vascular development in C57B16 mice from P0 to P30. At P0 only budding superficial vessels can be observed around the optic disc. Over the next few days, the primary superficial network extends toward the periphery, reaching the far periphery by day P10. Between P7 and P12, the secondary (deep) plexus develops. By P17, an extensive superficial and deep network of vessels is present (FIG. 22, insets). In the ensuing days, remodeling occurs along with development of the tertiary (intermediate) layer of vessels until the adult structure is reached approximately at P21.

Figure 23:
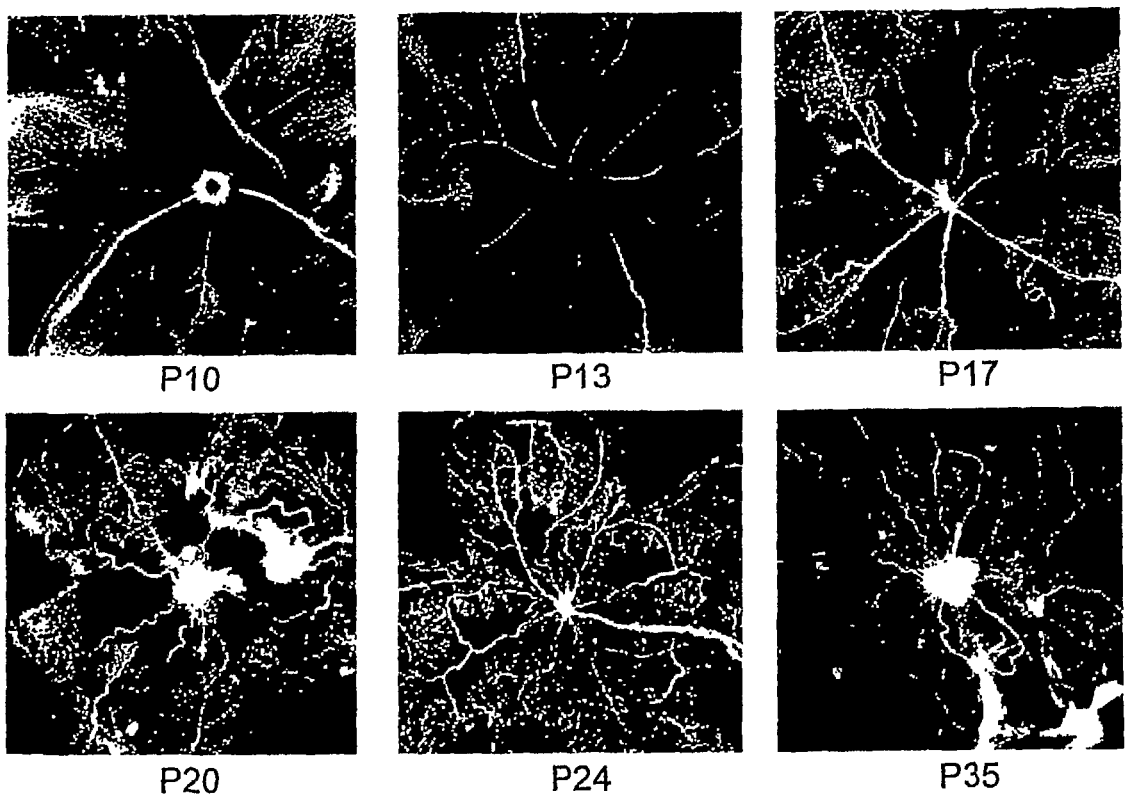
FIG. 23 illustrates oxygen-induced retinopathy model in C57/B16 mice raised in high oxygen levels (hyperoxia; 75% oxygen) between P7 and P12, followed by normoxia from P12-P17.
Figure 24:
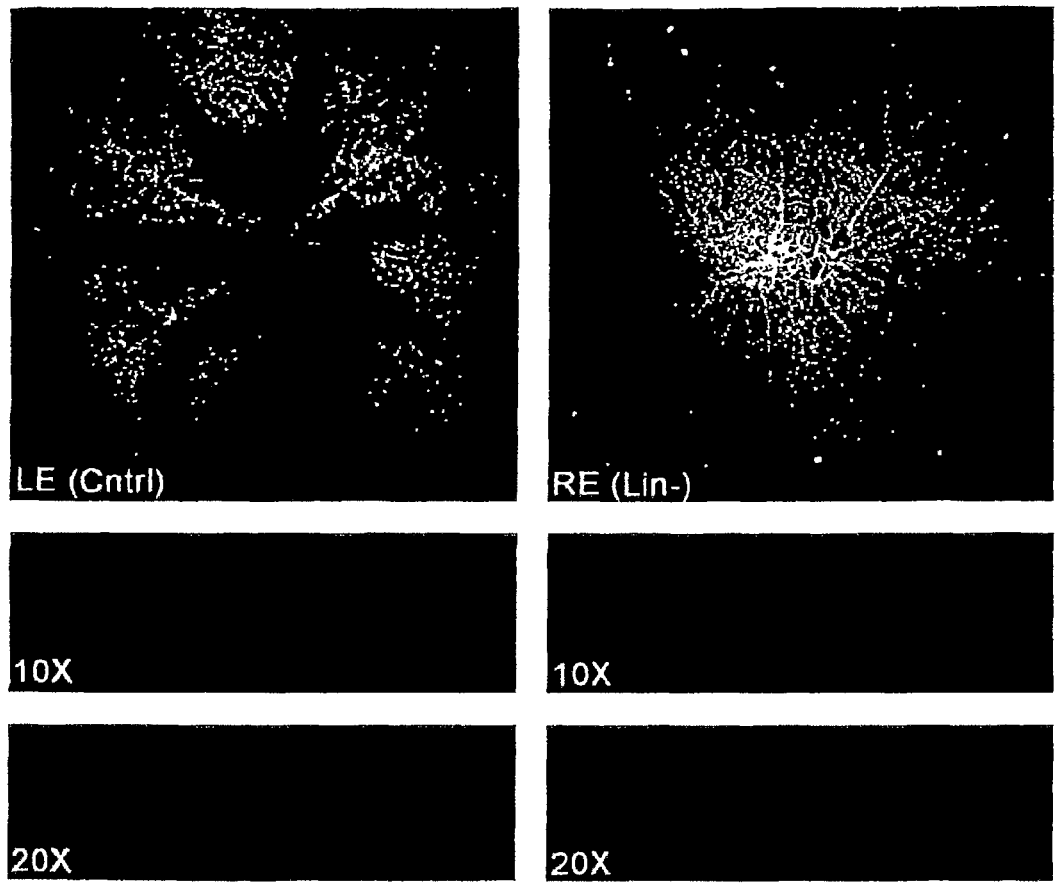
FIG. 24 demonstrates vascular rescue by treatment with the Lin⁻HSC populations in the oxygen-induced retinopathy (OIR) model.

In contrast, in the OIR model described herein, following exposure to 75% oxygen at P7-P12, the normal sequence of events is severely disrupted (FIG. 23). Adult murine Lin⁻ HSC populations of the invention were intravitreally injected at P3 in an eye of a mouse that was subsequently subjected to OIR, the other eye was injected with PBS or CD31 negative cells as a control. FIG. 24 illustrates that the Lin⁻ HSC populations can reverse the degenerative effects of high oxygen levels in the developing mouse retina. Fully developed superficial and deep retinal vasculature was observed at P17 in the treated eyes, whereas the control eyes showed large avascular areas with virtually no deep vessels (FIG. 24). Approximately 100 eyes of mice in the OIR model were observed. Normal vascularization was observed in 58% of the eyes treated with the Lin⁻ HSC populations, compared to 12% of the control eyes treated with CD31⁻ cells and 3% of the control eyes treated with PBS.

Example 11

Isolation of Myeloid-Like Bone Marrow Cells from Murine Bone Marrow by CD44 Selection Bone marrow cells were extracted from adult mice (The Jackson Laboratory, Me.). The whole bone marrow was treated with a murine CD44 antibody and flow cytometry was used to isolate CD44 expressing cells from the bone marrow. The cells were separated from the antibody and stored in a buffer solution for future use. A population of cells that do not significantly express CD44 was also isolated (CD44$^{lo}$BM).

Example 12

Isolation of Myeloid-Like Bone Marrow Cells from Murine Bone Marrow by CD44 Selection Bone marrow cells were also positively selected using an antibody to CD11b in place of CD44, as described in Example 11. A myeloid-like bone marrow cell population that was CD44$^{hi}$ and CD11b+ was isolated, which had similar activity characteristics to the CD44$^{hi}$ population isolated in Example 11 using CD44. A CD44$^{lo}$ CD11b⁻ population was also isolated, which was found to be inactive.

Example 13

Characterization of the MLBM Cell Populations

Although the role of CD44 in this context is not clear, it is possible that this receptor mediates cell survival, cell migration and/or cell differentiation in the hyaluronic acid-rich vitreous following injection of cells into the eye. Distinct populations of CD44$^{hi}$ (i.e., MLBM) and CD44$^{lo}$ cells were present in unfractionated mouse bone marrow. The MLBM cell population represents 76% of the Lin⁻ population used in previous examples, whereas only about 37% and 4%, respectively, of Lin⁺ and CD31⁻/CD34⁻/CD11b⁻ cell populations from bone marrow expressed CD44 (FIG. 26). Accordingly, there is an excellent correlation between CD44 expression and the vasculotrophic and neurotrophic activities observed in these three populations, i.e. Lin⁻ cells were the most effective while CD31⁻/CD34⁻/CD11b⁻ cells were consistently the least effective. Using a panel of lineage-specific antibodies, the majority of CD44$^{hi}$ cells were determined to have strongly myeloid characteristics (FIG. 27). Similarly, nearly all of the CD44$^{hi}$ bone marrow cells are also CD11b⁺ (FIG. 27).

MLBM positively selected using CD11b antibody in Example 12 (CD44$^{hi}$ CD11b⁺) gave activity results similar to those obtained with MLBM isolated using CD44 antibody selection in the vascular targeting experiments.

The cell surface antigen characteristics of the MLBM cell population of Example 12 and of the CD44$^{lo}$ CD11b+ cells isolated in Example 12 are shown in Table 3, below. In Table 3, a greater number of plus signs (+) indicates relatively higher expression of the antigen. A minus sign (−) indicates no expression detected.

TABLE 3

| Antigen | CD44$^{hi}$/CD11b+ | CD44$^{lo}$/CD11b− |
|---|---|---|
| CD11a | +++ | + |
| CD31 | + | ++ |
| CD34 | + | − |
| alpha 6 | ++ | − |
| KDR | + | − |
| Sca-1 | + | + |
| c-Kit | + | − |
| CD115 | + | − |
| CD45R/B220 | + | ++ |
| TER119 | − | +++ |
| Ly6G&C (GR-1) | +++ | − |
| Ly6G | +++ | − |

Example 14

Vasculotrophic and Neurotrophic Effects of The MLBM Cell Population

The MLBM cell population of Example 11 retained the properties of Lin⁻ cells in terms of vascular targeting and vasculo- and neurotrophic effects, while CD44$^{lo}$BM cells showed little or no activity. Vascular targeting activity was demonstrated by injecting cells from a GFP$^+$ MLBM cell population intravitreally into postnatal day 7 (P7) mice and analyzing retinas at P14. After labeling blood vessels with GS isolectin, GFP$^+$ cells were observed to target the retinal vasculature and assume a perivascular localization, without evidence of incorporation. These events were common when using MLBM, but infrequent or absent in eyes treated with CD44$^{lo}$BM (FIG. 28).

Vasculo- and neurotrophic activity of the MLBM cell population of Example 11 was evaluated using a mouse model of retinal degeneration as described above for Lin$^-$ HSC. The rd1/rd1 mouse shows characteristic features of retinal degenerative disease including photoreceptor death and atrophy of the deep retinal vasculature. As described above, Lin$^-$ HSC bone marrow cells preserved the deep retinal vasculature and partially rescued photoreceptors. The MLBM cell population of the present invention performs the same function (FIG. 29).

The oxygen-induced retinopathy model shares features with retinopathy of prematurity. The pathology associated with this model is significantly reduced when eyes are treated with cells from the MLBM cell population. The effects of cells from the MLBM cell population in this model were similar to those observed using Lin$^-$ HSCs described above. Eyes treated with cells from the MLBM cell population showed significant reduction in the two parameters used to quantify the degree of pathology in this model: vascular obliteration area and neovascular tuft area. In contrast, eyes treated with CD44$^{lo}$BM cells showed no improvement over eyes treated with vehicle controls (FIG. 30).

In addition to targeting retinal vasculature, cells from the MLBM cell population differentiate into macrophage-like (F4/80$^+$) cells, penetrate the retina, and take a position closely opposed to the retinal pigment epithelium (RPE). This localization facilitates the observed vascular and photoreceptor rescue effects of the cells from the MLBM cell population. Furthermore, once in place near the RPE, the cells from the MLBM cell population produce vascular endothelial growth factor (VEGF), as demonstrated by injection of cells from a MLBM cell population derived from a VEGF-GFP mouse, in which green fluorescent protein (GFP) is expressed upon VEGF gene activation (FIG. 31). Thus, the cells from the MLBM cell population appear to be in a VEGF "activated" state. The introduced cells from the MLBM cell population appear to recruit endogenous cells of the same type, since both GFP$^+$ (introduced) and GFP$^-$ (endogenous) cells were observed in the RPE region. This localization has been observed in wild type mice during normal retinal vascular development, in rescued retinas in the rd1/rd1 mouse and in the oxygen-induced retinopathy model.

Figure 32:
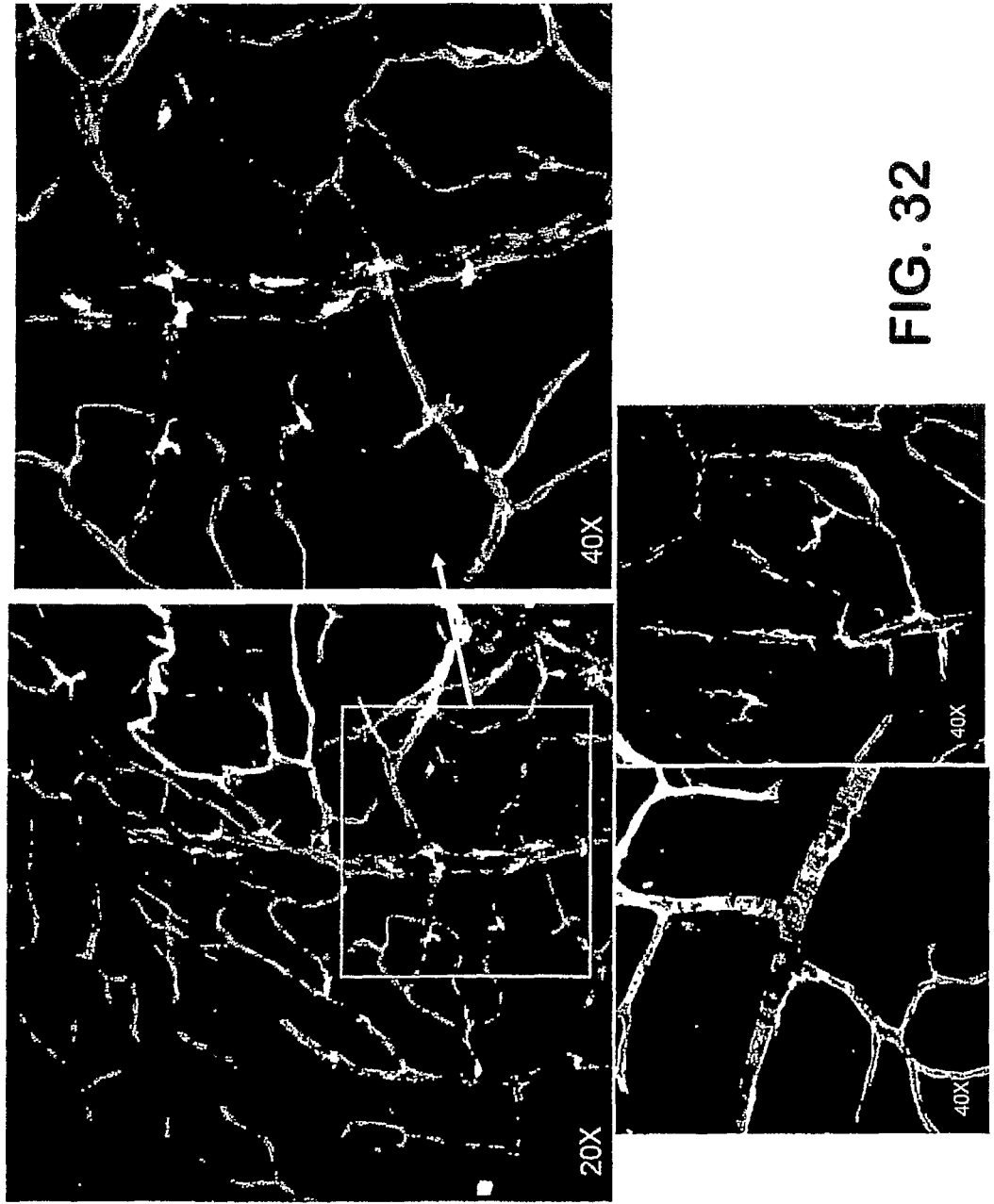
FIG. 32 depicts photomicrographic images demonstrating that cells from the CD11b⁺ MLBM cell population of the invention selectively target the vasculature of the retina.

Similar vascular targeting results were found for the MLBM cell population of Example 12. FIG. 32 shows that by P20, CD44$^{hi}$CD11b$^+$ cells of Example 12 (green) specifically targeted the vasculature (red) when injected at P2, in a manner similar to the CD44-high population of Example 11. FIG. 33 shows that the CD44$^{lo}$CD11b$^-$ of Example 12 did not specifically target the vasculature.

The MLBM cell population of the present invention provide an effective and versatile treatment for ocular diseases. The cells are readily isolated from autologous bone marrow, thus minimizing potential immunogenicity often observed in cell-based therapies. In addition, the MLBM cell population of the invention can be transfected with useful genes for delivering functional genes to the retina.

Example 15

Further Characterization of Bone Marrow Cell Subpopulations

As described in the previous examples, all experiments were performed in accordance with the NIH Guide for the Care and Use of Laboratory Animals, and all experimental procedures were approved by the TSRI Animal Care and Use Committee. OIR was induced in C57B16 mice according to the protocol described above. Post-natal day 7 pups and their mothers were transferred from room air to an environment of 75% oxygen for 5 days, and afterwards returned to room air. Oxygen levels were monitored using an FDA-approved oxygen analyzer (AX-300, Teledyne Analytical Instruments, CA, USA). Under these conditions, large hypovascular areas are formed in the central retina during hyperoxia and abnormal pre-retinal neovascularization occurs after return to normoxia, peaking at around P17 and ultimately resolving (FIG. 37, Panels g-i; FIG. 2, Panels a,c).

Cell Preparation: Mouse bone marrow cell extraction was performed substantially as follows: Bone marrow cells were harvested from femurs and tibia of actGFP mice and were processed using two different methods. In the first method, mononuclear cells were separated by density gradient using FICO/LITE LM® (Atlanta Biologicals, Norcross, Ga.) and labeled with biotin-conjugated lineage antibodies (CD45R/B220, CD3e, Ly-6G/C, CD11b, TER119, Pharmingen, San Diego, Calif.). This was followed by incubation with strepavidin or anti-biotin magnetic beads and sorting using the MACS cell sorting system (Miltenyi Biotech, Auburn, Calif.) to obtain Lin$^-$ HSC populations. In the second method, whole bone marrow was incubated with an antibody directed against CD44, which was conjugated to a fluorescent label. Fluorescence activated cell sorting (FACS) was then used to isolate CD44$^{HI}$ cells (i.e., an MLBM cell population cell population in which as majority of the cells express CD44) and CD44$^{LO}$ cells (i.e., a cell population in which as minority of the cells express CD44).

Bone Marrow Cell Characterization: Further analysis of the cell subpopulations obtained by the above methods was performed using two procedures: (1) two-color flow cytometry in combination with antibodies against various lineage and progenitor cell surface markers, including CD11a, CD11b, Ly6G/C, CD43, F4/80, CD14, cKit, CD34, α6 integrin, and CD115 (all from Pharmingen, San Diego, Calif.); and (2) gene expression analysis using AFFYMETRIX® Mu430 Chips (Affymetrix, Santa Clara, Calif.) using standard methods known in the art. Gene expression was analyzed using GENESPRING® software (Agilent Technologies, Palo Alto, Calif.).

Intravitreal injection: An eyelid fissure was created by gentle dissection to expose the globe in P2-P7 (pre-hyperoxia) mice. In one eye of each animal, about 150,000 to 250,000 bone marrow-derived cells in 0.5 μl vehicle (PBS containing 0.5% BSA and 2 mM EDTA) were injected into the vitreous using a Hamilton syringe and a 33 gauge needle (Hamilton, Reno, Nev.). In the contra lateral control eye, an approximately equal number of control cells or vehicle alone was injected, and in some cases no injection was performed at all to observe the natural course of disease. In subsets of experiments, cell transplantation was performed at later ages, between P9 and P12.

Staining of retinal vasculature: Retinas were harvested at P17 for imaging of the vasculature and to localize and characterize the injected cells. In some cases, animals were anesthetized and intra-cardiac flourescein-labeled high molecular weight dextran (FITC Dextran, Sigma) was injected prior to dissection of the retinas to visualize patent vessels. In other cases, immunohistological techniques to stain blood vessels and GFP-expressing cells were used. The retinas were fixed in 4% perfluoroacetic acid (PFA) and methanol, followed by blocking in 20% FBS/20% NGS for one hour at room temperature. This was followed by overnight incubation with isolectin GS-IB4 conjugated to ALEXA® 594 to identify vessels (Molecular Probes, Eugene, Oreg.). Retinas were laid flat with radial relaxing incisions to obtain whole-mount preparations, or embedded in OCT and cryo-sectioned to obtain cross sections of the retina which are counter-stained with DAPI prior to mounting.

In order to characterize the transplanted cells, immunohistological techniques were used to identify the following cellular markers in subsets of eyes: F4/80 (Caltag, Burlingame, Calif.), CD44, CD31 (Pharmingen, San Diego, Calif.), and NG2 (Chemicon, Temecula, Calif.). All retinas were triple stained with lectin, anti-GFP and one of the above described markers.

Imaging and Image Analysis: Images of the retinal vasculature were obtained using a RADIANCE® 2100MP laser scanning confocal microscope (Biorad, Hercules, Calif.). Quantification of vaso-obliteration and neovascularization was carried out as follows: The area of vascular obliteration was measured by carefully outlining the avascular zones in the central retina of GS lectin-stained retinas and calculating the total area using PHOTOSHOP® (Adobe) or VOLOCITY® software (Improvision, Lexington, Mass.). Similarly, the area of pre-retinal neovascularization ("tufts") was calculated by using confocal images focused at the pre-retinal plane and selecting tufts based on pixel intensities (tufts label more brightly that normal vasculature). Selected regions were then summed to generate total area of neovascularization. A T-test was used to statistically compare the different experimental groups.

Three dimensional images of retinal vasculature and perivascular bone marrow cells were generated by collecting a z-series of confocal images and rendering them into volumes using VOLOCITY® software. It was then possible to view retinal vessels in cross section and determine the position of transplanted bone marrow cells relative to the vascular lumen Retinal vascular development and the mouse model of oxygen-induced retinopathy. Normal retinal vascular development in post-natal mice grown under normoxic conditions is shown in FIG. 37, Panels a-f. At post natal day 2 (P2) only budding superficial vessels are observed occupying a single plane around the optic disc (FIG. 37, Panels a,b). Over the course of the next week, the primary superficial network extends towards the periphery, reaching the far periphery at approximately P12 (FIG. 37, Panel c). Between P7-P12, the secondary (deep) plexus develops (FIG. 37, Panel d). By the end of the first month, remodeling occurs in the fully vascularized retina (FIG. 37, Panel e) along with development of the tertiary (intermediate) layer of vessels, and the adult structure is reached (FIG. 37, Panel f).

In contrast, in the OIR model, exposure to 75% oxygen from P7-P12 severely disrupts the normal sequence of events: marked regression of the superficial network of vessels that have already formed in the central retina occurs, especially along the arteries (FIG. 37, Panel g (P10) and Panels h,i (P17)), and development of the deep plexus is severely delayed (FIG. 37, Panels k,m, retinal cross sections at P17). Vascular growth, in an abnormal fashion, commences again only after returning to normoxic conditions at P12. In essence, these are now relatively hypoxic conditions for the severely hypovascular retina. At P17, some deep vessels can be identified in the periphery, but abnormal pre-retinal neovascular tufts, associated with leak of intravascular dye, can be seen in the mid periphery, at the border between the hypovascular central retina and the more vascularized periphery (FIG. 37, Panel h). Over the ensuing days, the superficial and deep vessels slowly develop in the avascular areas, but neovascular tufts protruding above the inner limiting membrane (ILM) of the retina into the vitreous often persist until P21 or even later. By P25-P30, the retinal vasculature has remodeled and resembles the normal vasculature at this time.

Injection of hematopoietic progenitor cells prior to hyperoxia promotes vascular repair in the retina following oxygen-induced vaso-obliteration. Injection of Lin⁻HSCs of the invention at P2-P7 dramatically changed the ability of the retinal vasculature to recover following hyperoxic exposure (FIG. 37, Panels j,l,n,o, and FIG. 38, Panels b,d,e,f,g). Injection of vehicle alone did not induce such changes. In over 50% of cases, fully developed superficial and deep retinal vasculature was seen in Lin⁻ HSC-injected eyes at P17 while contra lateral vehicle-injected eyes show large avascular areas and practically no deep vessels (FIG. 37, Panels l,n, compared to Panels h,i,k,m, and to Panel o). In some cases, especially when the injury in the contra lateral control eye was very severe, recovery was not complete by P17 in the Lin⁻ cell-injected eye, but was significantly better in the large majority of cases. This comparison between fellow eyes in the same animal provides further support for the efficacy of the Lin⁻ HSCs, effectively equalizing most other genetic and environmental factors.

Figure 38:
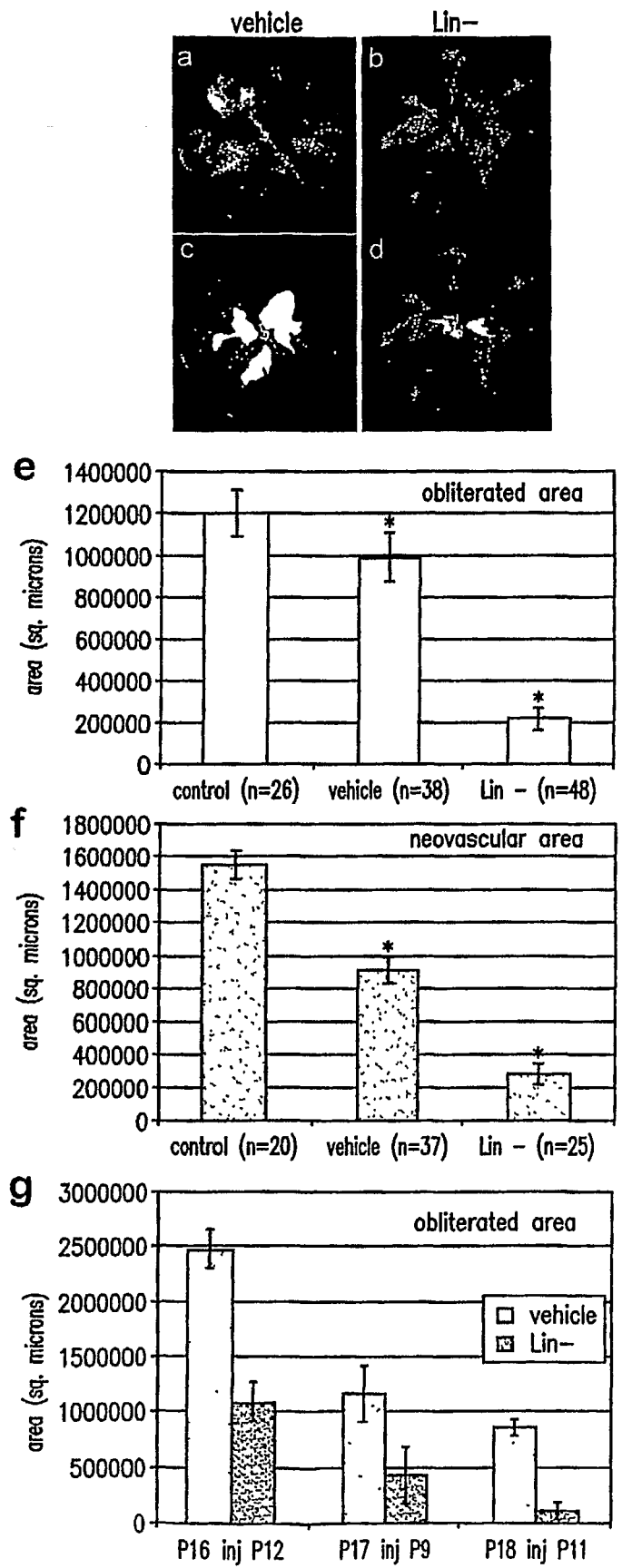
FIG. 38 shows Lin⁻ cells accelerate retinal revascularization and reduce pre-retinal neovascular tuft formation in OIR. Panels a-d show a computer image analysis method was used to calculate the area of retinal vessel obliteration, as well as pre-retinal neovascular tuft formation (red) in retinal wholemounts from OIR eyes at postnatal day 17. Panel e shows retinas treated with Lin-cells prior to hyperoxia showed an almost 6-fold reduction in obliterated area versus uninjected controls and an approximately 5-fold reduction compared to eyes treated with vehicle alone. Panel f shows Lin⁻ cell treatment significantly reduced two-dimensional area of neovascular tufts compared to uninjected eyes and vehicle-treated eyes. Panel g shows Lin⁻ cell-transplantation is effective at reducing the area of obliteration not only when administered prior to hyperoxia, but also at P9-P12 during hyperoxia and just after return to normoxia. (graphs represent Mean±SEM; *p<0.001).

Vascular obliteration has been an underappreciated feature in this model, since most studies have only analyzed pre-retinal neovascular tuft formation in serial retinal sections. Vascular obliteration and tuft formation can be evaluated in the same retina using confocal microscopy and digital image analysis (see e.g., FIG. 38, Panels a-d). P17 was selected as the main time point for analysis, because tuft formation is often maximal at this time, while significant vascular obliteration is still present in control eyes. Using the novel method of combined analysis, substantial differences between treated and control eyes were identified. Vascular obliteration measured at P17 was significantly reduced (over 75% reduction in obliterated area) in Lin⁻ treated retinas compared to eyes receiving vehicle alone, or no injection (FIG. 38, Panel e). No significant difference was observed between vehicle injection and no injection in this regard. Similarly, eyes treated with Lin⁻ cells had an approximately 70% reduction in neovascular tuft area compared to vehicle-injected eyes and greater than 80% reduction versus non-injected controls (FIG. 38, Panel f). Thus, treatment of eyes with Lin⁻ HSCs had a dramatic effect on the two major vascular injury and repair parameters of the mouse OIR model, i.e., simultaneously reducing formation of neovascular tufts while accelerating "physiologic" inner-retina revascularization.

Accelerated repair was also observed when treatment was performed during hyperoxia and upon return to normoxia, but the effect was reduced. The experiments described thus far involved injections performed on days P2-P7, prior to exposure to hyperoxia. To determine whether Lin⁻ cells could also affect vascular repair if injected later, during the hyperoxia phase of the cycle and upon return to normoxia, injections were performed at P9, P11 or P12, and retinas were evaluated at various later time points. The results are shown in FIG. 38, Panel g and demonstrate that injection of Lin⁻ HSCs was effective at accelerating vascular repair and reducing the area of obliteration even when administered during hyperoxia and at P12. The effect, however, appeared to be somewhat attenuated, indicating that maximal efficacy is achieved when treatment is performed prior to high oxygen exposure.

Figure 39:
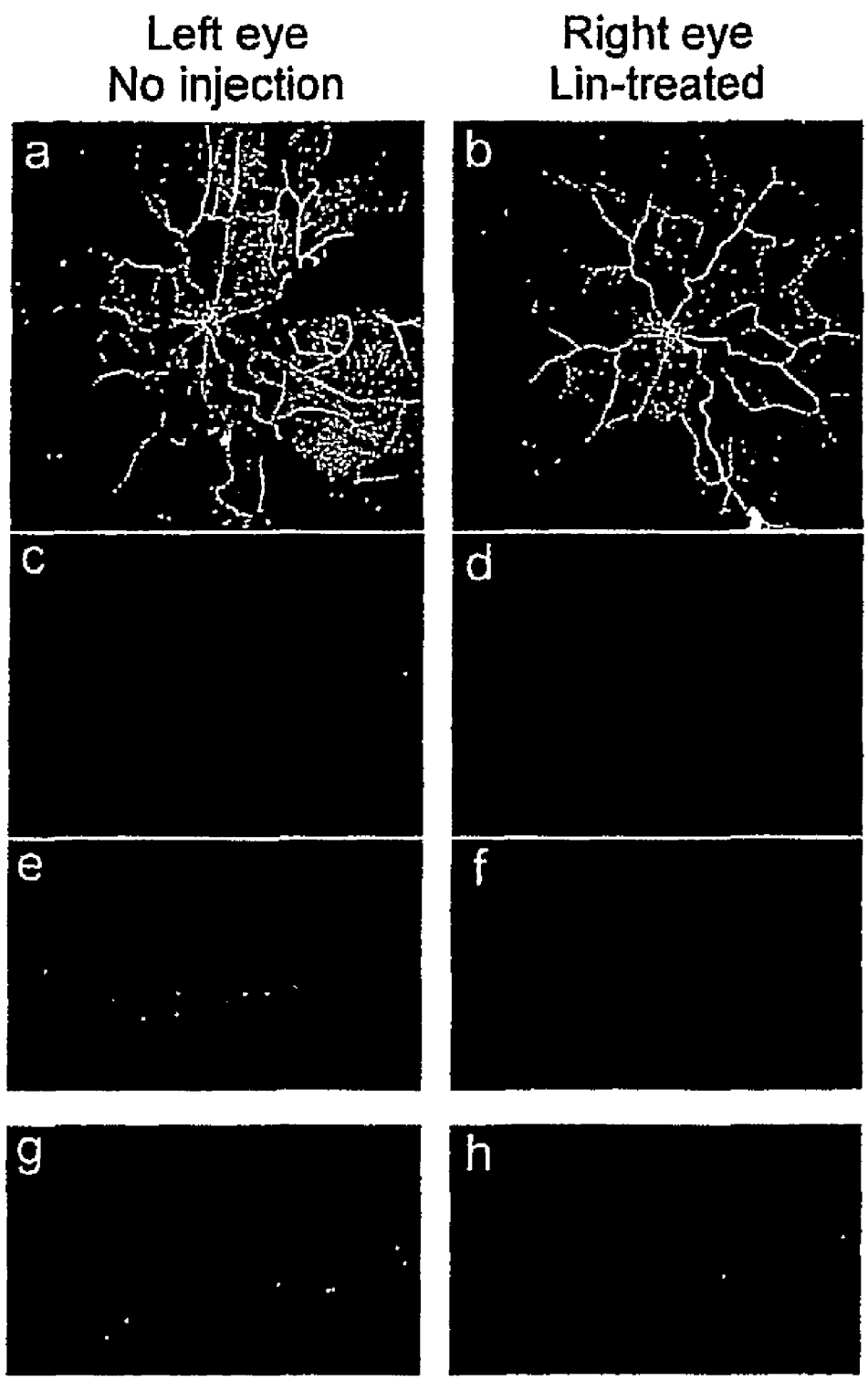
FIG. 39 shows bone marrow cell treatment has little or no long term toxic effects. Retinas evaluated at 5 or 6 months after receiving Lin⁻ cell treatment have normal-appearing retinal vasculature and the neural retina appears histologically preserved on cross sections (a-f, non-injected versus Lin⁻ cell-injected retina 6 months post-transplant). No tumors were observed, and the only abnormality was an occasional "rosette" in the neural retina which could also be seen in control non-injected eyes (g,h).

Following treatment with Lin⁻ hematopoietic progenitor cells, long term retinal structure and function were well preserved. The long-term effects and possible side effects of treatment with Lin⁻ HSCs were also studied. To this end 12 retinas were taken from mice at 3-6 months of age that had undergone Lin⁻ cell injection and exposure to hyperoxia according to the established model (FIG. 39). No tumors were observed and the neural retina appeared to be preserved histologically in all cases. The only notable abnormality was an occasional "rosette" formation within the retina, a finding also present in control eyes (FIG. 39, Panels g,h). The retinal vasculature from Lin⁻ HSC-injected eyes had a normal appearance, and no obvious differences from non-injected control retinas were found (FIG. 39, Panels a-f).

Long term persistence of the transplanted cells was also studied. GFP⁺ cells were observed in only a small percentage of eyes (10%) indicating that the majority of injected cells did not survive beyond several months. When present, surviving cells were often located in close proximity to the retinal vasculature. Retinal function, as measured by electroretinographic recordings performed at 17days to 6 months post-transplantation, showed no difference between Lin⁻ HSC-transplanted eyes and normal, non-OIR age-matched controls. To examine the possibility that transplanted cells may exit the eye and disseminate systemically, spleens and/or livers from 15 mice were analyzed for the presence of GFP⁺ cells about 7 to 10 days after injection. No extra-ocular cells were observed.

Figure 40:
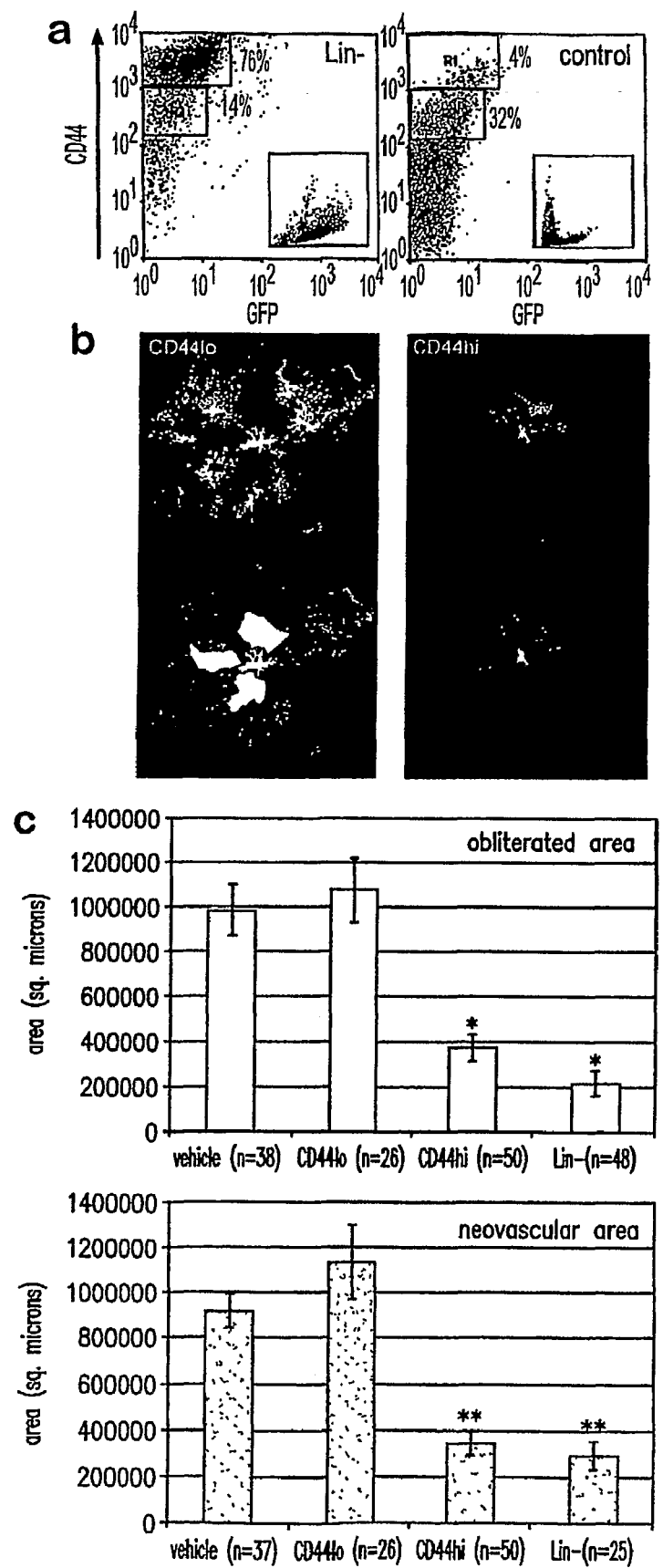
FIG. 40 shows $CD44^{HI}$ cells are prevalent in the Lin⁻ population and effectively promote vascular repair in the OIR model. Panel a shows bone marrow contains $CD44^{HI}$ and $CD44^{LO}$ fractions and the Lin⁻ population is enriched for $CD44^{HI}$ cells compared to control CD cells. Insets show light scattering properties of the $CD44^{HI}$ cells which are typical of monocytes and granulocytes, while light-scattering properties of $CD44^{LO}$ cells are typical of lymphocytes. Panel b shows representative P17 retinas from eyes treated with $CD44^{LO}$ and $CD44^{HI}$ bone marrow cells prior to oxygen exposure. The lower panels exemplify the quantified areas of obliteration and neovascularization at P17 used to create the data shown in panel c. Panel c shows vascular obliteration and pre-retinal neovascularization are reduced in eyes treated with $CD44^{HI}$ cells with efficacy similar to eyes treated with Lin⁻ cells. Areas of vascular obliteration (*) and pre-retinal neovascularization (**) were significantly lower in $CD44^{HI}$ and Lin⁻ eyes compared with vehicle injection or no injection ($p<10^{-5}$ in all cases). Area of obliteration in Lin⁻ cell-treated eyes was also reduced compared to $CD44^{HI}$ (p=0.03), but to a much lesser degree. Areas of pre-retinal neovascularization did not significantly differ between Lin⁻ and $CD44^{HI}$-treated eyes (p=0.25).

Verifying the active cell type: The Lin⁻ population is enriched for $CD44^{HI}$ cells. In an effort to better understand the mechanisms that may be active during these processes and to simplify the cell selection procedure, an attempt was made to identify a single marker that could be used to isolate active HSCs from the bone marrow. Based on characteristics such as involvement in cell migration and differentiation, a large panel of candidate bone marrow progenitor markers was assembled. Using flow cytometry, these markers were screened, comparing their expression in the active Lin⁻ cells versus that in control BM cells that were previously shown to be inactive in a number of experimental systems. CD44 proved to be differentially expressed in these two populations: $CD44^{HI}$ cells were present in a significantly higher proportion of the Lin⁻ cells (76%) than in the control BM cell population (4%) (FIG. 40, Panel a). As noted above, CD44 is a cell surface receptor for hyaluronic acid, and has been shown to participate in the regulation of several cellular functions that are believed to be important in mediating the rescue effect including survival, migration and differentiation. The distribution of $CD44^{HI}$ cells, being highly prevalent in the active cell population and quite rare in the control cells with reduced activity, indicated that CD44 is, indeed, an effective indicator of activity.

For example, $CD44^{HI}$ cells promote vascular repair in the OIR model, while $CD44^{LO}$ cells do not. The efficacy of $CD44^{HI}$ cells was verified in the OIR model for their ability to facilitate vascular repair. Using the same experimental design as that described for Lin⁻ cell injections, $CD44^{HI}$ cells were demonstrated to promote retinal vascular repair in this model with efficacy similar to that observed with Lin⁻ cells (FIG. 40, Panels b,c). In contrast, CD44lo cells had no positive effect on repair. It is of value to point out that often few or no injected cells were observed within the retinas of $CD44^{LO}$-treated animals, suggesting that these cells have reduced ability to survive in the vitreous and/or migrate into the retina. It is not known whether the $CD44^{HI}$ cells are the only active bone marrow sub-population or one of others that have this activity.

Figure 41:
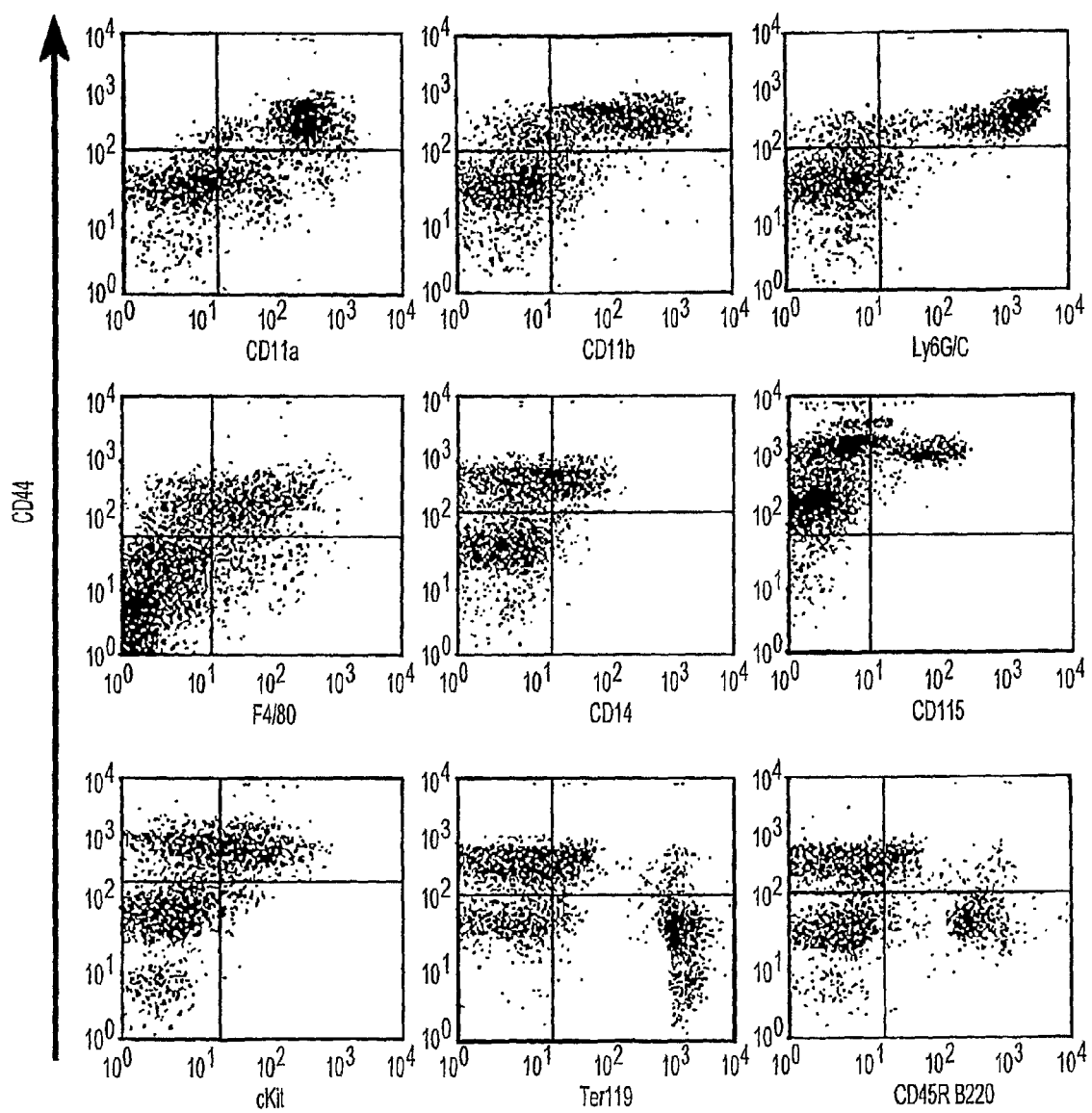
FIG. 41 shows the $CD44^{HI}$ subpopulation expresses myeloid markers. In Panel a, two-color flow cytometry was used to further characterize CD44 populations. All cells were labeled with an antibody against CD44 and co-labeled with the various antibodies shown. The $CD44^{HI}$ population showed strong labeling for CD11a, CD11b and Ly6GC. Fractions of CD44hi cells were positive for CD14, F4/80, cKit, and CD115. Most of these antigens are present on myeloid lineage cells. CD44lo cells labeled strongly with Ter119 and CD45R B220, which are markers for erythroblasts and B cells, respectively.

$CD44^{HI}$ cells express genes and markers suggestive of myeloid origin. Further characterization of the $CD44^{HI}$ population was performed by large-scale expression analysis and by antibody labeling of Lin⁻ and progenitor-specific markers followed by flow cytometry (FIG. 41, and FIG. 44). Both methods revealed that $CD44^{HI}$ cells have an expression profile suggestive of myeloid origin. Strong expression of CD11a, CD11b, and Ly6G/C was observed on these cells at the protein level, while less intense positive labeling was detected for F4/80, CD14, cKit and CD115 by flow cytometry. Several myeloid-specific genes including CD204, CD114, CD33 and CD115 were highly expressed on expression analysis as compared with CD44lo cells (FIG. 44). In contrast, at the protein level, the $CD44^{LO}$ population had significant expression of Ter119 and CD45R B220, which are markers of erythroblasts/erythrocytes and B cells, respectively. On the expression array, a number of genes associated with lymphocytes were highly expressed in $CD44^{LO}$ as compared with $CD44^{HI}$ cells including CD19, CD79a and CD22 (FIG. 44). Thus, analysis at the transcriptional and protein levels identifies the active $CD44^{HI}$ population as primarily myeloid in origin while the inactive $CD44^{LO}$ cells are largely lymphoid.

Figure 43:
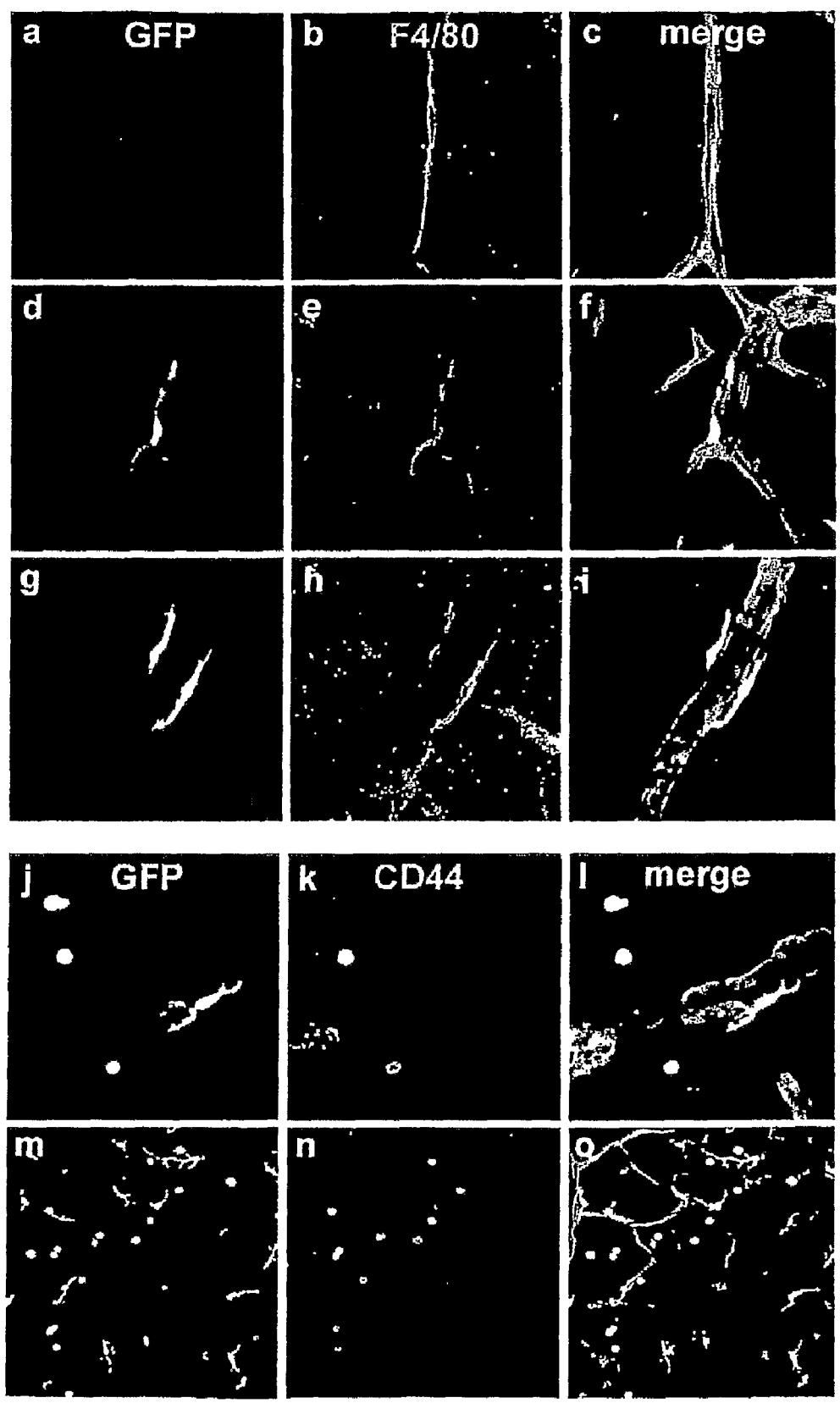
FIG. 43 shows an in situ analysis of injected $CD44^{HI}$ bone marrow cells in the OIR model. Labeling of a control retina that received no cell treatment shows the presence of endogenous F4/80+ perivascular cells (a-c). Injected $CD44^{HI}$ cells target the retinal vasculature and have a localization, morphology and F4/80 expression pattern similar to endogenous cells (d-i). Transplanted perivascular bone marrow cells lose CD44 expression, while cells not associated with the retinal vasculature retain CD44 expression (j-o).

Analysis of transplanted cells in situ—evidence for differentiation: Having more clearly defined the population of active cells from the bone marrow, the fate of these cells after introduction into the eye was investigated. To this end, $CD44^{HI}$-injected retinas from the OIR model were analyzed by immunohistochemistry with various markers. The vast majority of introduced cells selectively targeted the retinal vasculature and assumed a perivascular localization, often forming elongated structures tightly associated with host vessels (FIG. 42, Panel a). Using antibodies against CD31 and NG2, these markers were not detected on the GFP-expressing perivascular bone marrow cells, suggesting that these cells are not differentiating into endothelial cells or pericytes, respectively. In addition, the transplanted cells did not appear to form any portion of the vessel lumen (FIG. 42, Panel b), thus demonstrating that these cells are unlikely to be differentiating into endothelial cells. In contrast, the macrophage/microglia marker F4/80 labeled many, but not all, perivascular GFP⁺ cells in $CD44^{HI}$-treated eyes (FIG. 43, Panels d-i). These introduced F4/80⁺ cells had an appearance very similar to endogenous perivascular cells which also labeled with F4/80 (FIG. 43, Panels a-c), suggesting that the transplanted cells were assuming an identity similar to native cells in the OIR model.

One of the possible advantages of cell therapy, particularly in comparison to conventional pharmaceutical treatment, is the potential of the cells to respond to local cues and undergo modification in changing environments. Transplanted cells at P17 (10 days after injection) that had targeted the retinal vasculature and assumed a perivascular location were observed to have down-regulated CD44 to undetectable levels (FIG. 43, Panels j-o). Cells that were not associated with the vasculature retained expression of CD44, however. Thus, sub-populations of implanted cells that were originally selected by FACS on the basis of high CD44 expression down-regulated this receptor in-vivo, which correlated with the location of the cells in the retina. This suggests that the introduced cells do, indeed, undergo selective changes (differentiation) within the environment of the eye.

The results detailed above indicate that cell-based therapy can be used to treat ROP, and other ischemic retinopathies. The results observed in the mouse model indicate that this approach is efficacious in reducing the vascular pathology associated with high oxygen exposure and shows little or no toxicity. The advantage of using cell therapy, as opposed to single factor therapy, may lie in the ability of the cell to adapt and respond to a changing environment. The evolution from single factor therapeutics, to combinations of drugs and interventions, to the selection and delivery of sophisticated, adaptable cells that can orchestrate and conduct a complicated sequence of responses while interacting with the host tissue is an exciting new concept. In this respect, the present invention provides a "paradigm shift" in the approach to ischemic retinopathies/vasculopathies, i.e., emphasizing healing and stabilization instead of inhibition and obliteration.

The isolated MLBM cell populations of the invention target the retinal vasculature, can be used to deliver angiostatic agents, and have vasculo- and neurotrophic effects in models of retinal degeneration. In the present study, specific subpopulations of Lin$^-$ isolated MLBM cell populations are highly effective in accelerating the repair of OIR. Interestingly, the active cells express markers that suggest that they are of myeloid origin, and perhaps undergo differentiation and modification following transplantation.

The use of cell therapy to promote vascularization has been spearheaded by the field of cardiology with the goal of collateralizing infarcted arteries. A substantial amount of evidence indicates that certain bone marrow cells are effective at improving perfusion and cardiac function. It is not yet clear, however, which cell type(s) are responsible for the observed effects. Numerous studies investigating the potential role of bone marrow-derived endothelial progenitor cells (EPCs) have concluded that these cells are present in new or collateral vessels, but the small number of incorporated cells reported in some of these studies raises questions regarding their importance. Additionally, heterogeneous bone marrow populations, such as mononuclear cells or unfractionated cells, which contain very small numbers of stem cells and/or EPCs, can also significantly enhance collateral development, suggesting other mechanisms beyond direct incorporation into vessels are at work. While not intending to be bound by theory, it is possible that these cells play a supportive, paracrine role, by which factors secreted from them act to optimize the conditions for the host vasculature. Many bone marrow subpopulations have been shown to be a source of angiogenic factors, and monocytic cells are known to secrete a variety of such factors. Thus, the potential exists for bone marrow cells to serve in a paracrine fashion, complementing the role of EPCs in collateral vessel formation and interacting with the host immune system.

Although the precise mechanisms at work in this system are not yet clear, significant progress has been made in terms of understanding the nature of the functional bone marrow cells. With the identification of an active myeloid population within bone marrow, as provided by the cells of the present invention, some suggestions regarding mechanism can be made. Myeloid cells, notably monocytes and macrophages, have established abilities to influence blood vessel growth through secretion of angiogenic growth factors. In addition, macrophages have been shown to be more tolerant of hypoxia than other cells types and respond to low oxygen conditions by secretion of angiogenic factors. Thus, introducing myeloid progenitors into ischemic retinas could provide a cell that can withstand hypoxic conditions and can promote vascular repair in a paracrine manner. The presence of host-derived F4/80$^+$ perivascular cells in the OIR retina suggests that this type of cell has a role in the process, and perhaps the delivery of a large pool of similar cells (or their progenitors) by direct transplantation into the eye augments this effect. This scenario highlights the paradoxical observation that, as observed in the present studies, injection of cell populations of the present invention promotes revascularization of the retina while suppressing pre-retinal neovascularization. Although the basis for this is not yet fully known, it is possible that accelerated "physiologic" revascularization may reduce the hypoxia experienced by the retina such that ischemia-stimulated neovascular tufts do not form to the same degree.

The idea of myeloid-like cell support of vessel growth may have relevance to some earlier work relating to the rd1 and rd10 mouse models of retinal degeneration. Injected myeloid progenitors could act to maintain the deep retinal vasculature through secreted factors and prevent the vessel degeneration that is observed in these models. Some macrophage-secreted angiogenic factors, such as bFGF, have demonstrated neurotrophic activity as well. Thus, the observed reduced photoreceptor death upon injection of the cell populations of the present invention in rd mice could be mediated though a paracrine mechanism, in which neurotrophic factors are produced by the transplanted bone marrow-derived myeloid cells. In support of this mechanism, the present studies indicate that THE isolated MLBM cell populations of the invention are capable of vascular and neuronal rescue in the rd model with efficacy similar to that observed upon injection of isolated MLBM cells.

In a clinical treatment for ROP, fetal cord blood cells are harvested during the birth of a high risk premature infant, the cells are then sorted to enrich for the specific subpopulation which mediates the rescue effect, and these autologous progenitor cells can then be injected into the eye of the infant.

One of the main current limitations for the use of cell therapy is the fact that in many cases the exact molecular mechanisms of action are not yet clear, and in fact these mechanisms may differ between models. However, this may actually be the greatest advantage of cell-based therapies, i.e., the ability to respond in a different way and with a wide repertoire to changing conditions and cues. This is true not only between different experimental systems and challenges, but also temporally within one system. In other words, such cells may be secreting certain factors at one time point and different factors at another and ultimately, if the need for them subsides, may cease acting altogether. This is something that current chemical-based drug therapies cannot do, and is based on the fact that cells fundamentally use and respond to feedback. The modification of cellular markers in the transplanted cells in vivo observed in the present study supports this concept.

Example 16

MLBM Cells Differentiate Into Cells With Microglial Characteristics

Figure 45:
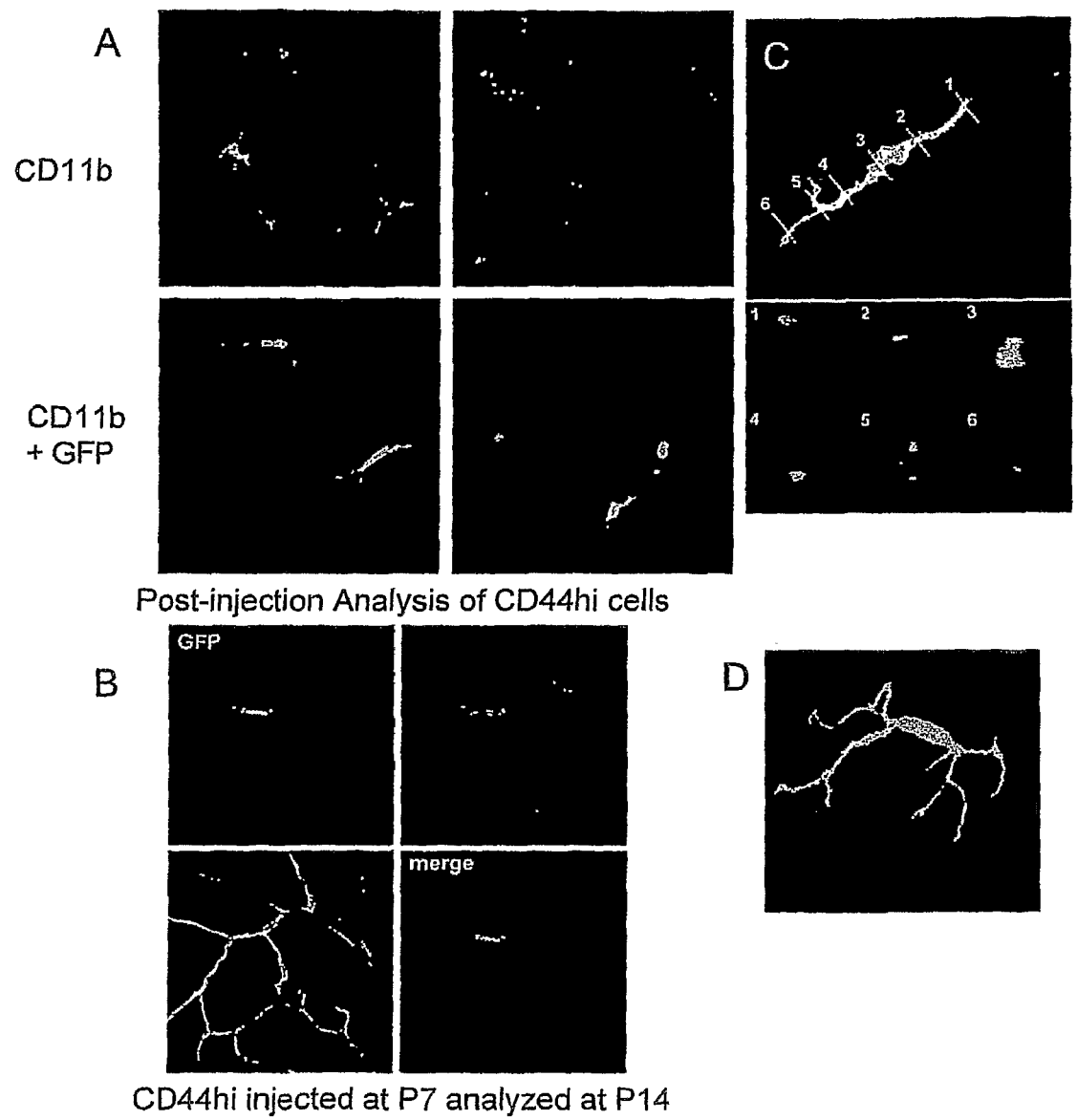
FIG. 45 demonstrates that $CD44^{HI}$ cells can differentiate into cells with microglial characteristics. Panels A and B show that injected $CD44^{HI}$ cells express CD11b and F4/80 and have morphology and perivascular localization similar to endogenous microglia. Panel C provides 3d imaging of the perivascular localization of an injected $CD44^{HI}$ cell. Panel D shows a high magnification view of the morphology of injected $CD44^{HI}$ cells.

Analysis of retinas following injection of CD44$^{HI}$ cells indicates that the CD44$^{HI}$ population of bone marrow cells are differentiating into microglia after injection into the eye. Microglia are the resident myeloid population in the retina and express characteristic markers including CD11b and F4/80. These cells are also distinguished by their ramified (branched) morphology and assume perivascular localization. The localization, morphology and surface marker expression of CD44hi cells at various points after injection into eyes has been analyzed. It is observed that injected CD44$^{HI}$ GFP$^+$ cells display all of the described characteristics of endogenous retinal microglia (FIG. 45). Panels A and B in FIG. 45 show that injected $CD44^{HI}$ cells express CD11b and F4/80 and have morphology and perivascular localization similar to endogenous microglia. Panel C provides 3D imaging analysis that demonstrates that injected $CD44^{HI}$ cells localize in the perivascular region. Panel D shows a high magnification view of the morphology of injected $CD44^{HI}$ cells.

Example 17

Isolation of MLBM Cells by Negative Selection

It is desirable for the purposes of experimentation and clinical applications to inject cells that are free of surface-bound selection agents, such as antibodies and/or magnetic beads. One way of achieving this goal is to utilize a negative selection strategy to isolate $CD44^{HI}$ cells. Through characterization of the surface marker expression profiles of the $CD44^{HI}$ and $CD44^{LO}$ cell populations described herein, it has been discovered that $CD44^{LO}$ cells displayed high expression of Ter119 and CD45RB220, markers of erythroid cells and B cells, respectively. Antibodies against these markers, with the addition of the T cell marker CD3e, efficiently labeled the $CD44^{LO}$ population and allowed for their removal via magnetic or FACS separation, leaving "untouched" $CD44^{HI}$ cells as the product. Cells separated by FACS using this strategy show the typical functional characteristics of the MLBM cell populations of the present invention (FIG. 46).

Figure 46:
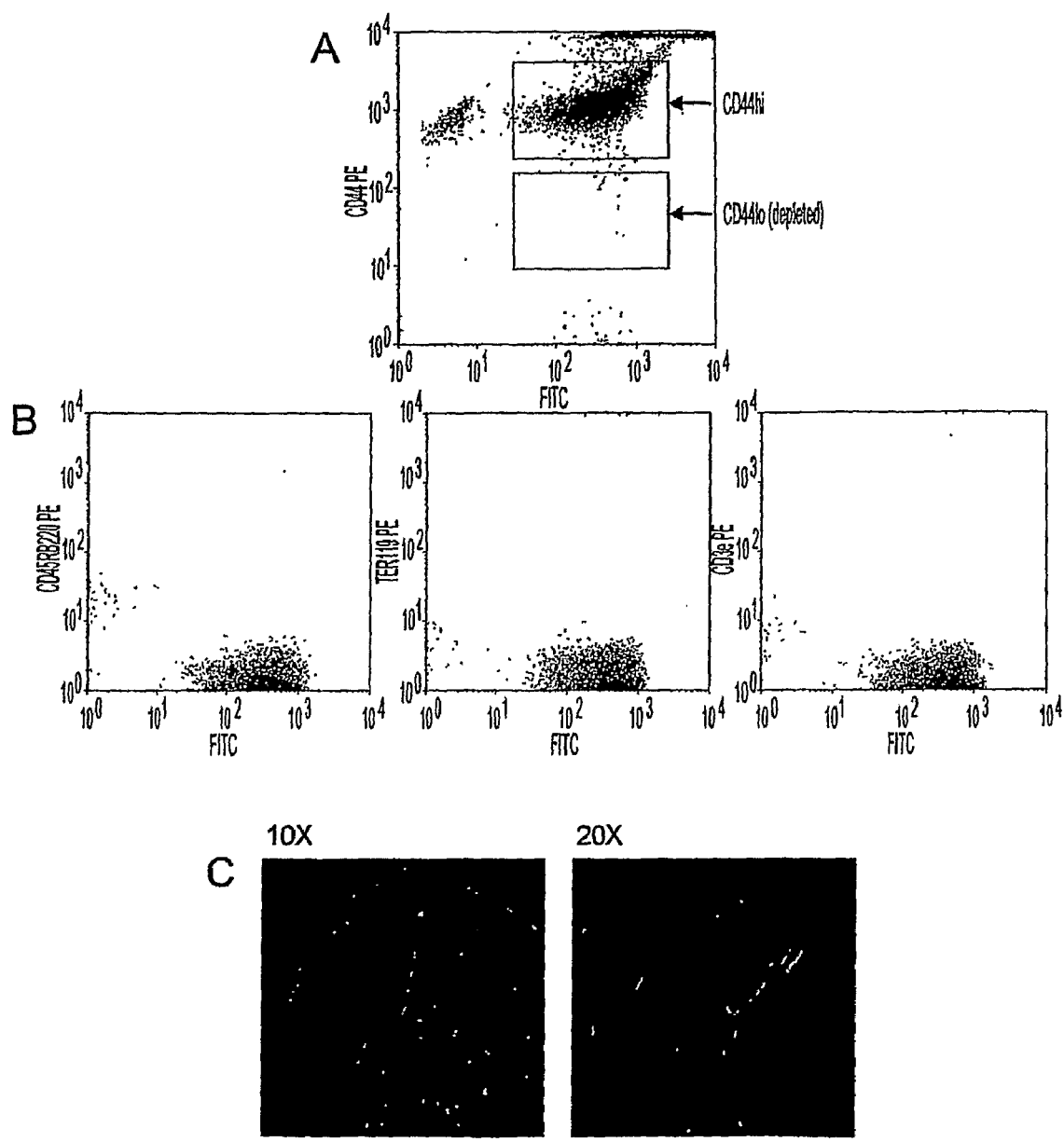
FIG. 46 demonstrates that $CD44^{HI}$ cells can be isolated by negative selection. Panel A shows that depletion of mouse bone marrow by MACS using antibodies selective for CD45R/B220, TER119, and CD3e yields a population of cells that are greater than 90 percent $CD44^{HI}$ cells. Panel B shows the negative fraction ($CD44^{HI}$ population) is essentially free from CD45R/B220, TER119, and CD3e cells. Panel C shows negatively selected $CD44^{HI}$ cells retain retinal targeting and differentiation capabilities.

FIG. 46, Panel A shows that depletion of mouse bone marrow by MACS using antibodies selective for CD45R/B220, TER119, and CD3e yields a population of cells that are greater than 90 percent $CD44^{HI}$ cells. Panel B shows the negative fraction ($CD44^{HI}$ population) is essentially free from CD45R/B220, TER119, and CD3e cells. Panel C shows negatively selected $CD44^{HI}$ cells retain retinal targeting and differentiation capabilities.

Numerous variations and modifications of the embodiments described above may be effected without departing from the spirit and scope of the novel features of the invention. No limitations with respect to the specific embodiments illustrated herein are intended or should be inferred.

We claim:

1. An isolated bone marrow cell population comprising a majority of cells that express both CD44 antigen and CD11b antigen; wherein the cell population is produced by a method consisting of isolating bone marrow from a mammal, reacting cells from the bone marrow with an anti-CD44 antibody and an anti-CD11b antibody, positively selecting cells that immunoreacted with the antibodies, and isolating a CD44 and CD11b expressing cell population therefrom.

2. The isolated bone marrow cell population of claim 1 wherein the cells are murine cells.

3. The isolated bone marrow cell population of claim 2 wherein the cell population is substantially free from TER-119 expressing cells.

4. The isolated bone marrow cell population of claim 1 wherein the cells are human cells.

5. A method of preparing an isolated bone marrow cell population in which a majority of the cells of the cell population express CD44 and CD11b, the method comprising isolating bone marrow from a mammal, reacting cells from the bone marrow with anti-CD44 antibody and an anti-CD11b antibody, positively selecting cells that immunoreacted with the antibodies, and isolating a CD44 and CD11b expressing cell population therefrom.

6. An isolated, transfected bone marrow cell population comprising a majority of cells that express both CD44 antigen and CD11b antigen, wherein the cell population is produced by a method consisting of isolating bone marrow from a mammal, reacting cells from the bone marrow with an anti-CD44 antibody and an anti-CD11b antibody, positively selecting cells that immunoreacted with the antibodies, isolating a CD44 and CD11b expressing cell population therefrom, transfecting the CD44 and CD11b expressing cells with a gene that operably encodes a therapeutically useful peptide, and isolating the transfected cells.

7. The isolated, transfected bone marrow cell population of claim 6 wherein the therapeutically useful peptide is an anti-angiogenic peptide.

8. The isolated, transfected bone marrow cell population of claim 6 wherein the therapeutically useful peptide is a neurotrophic agent.

9. The isolated, transfected bone marrow cell population of claim 6 wherein the cells are human cells.

10. The isolated bone marrow cell population of claim 1, wherein at least about 75 percent of the cells in the population express CD44.

11. The isolated bone marrow cell population of claim 1, wherein at least about 90 percent of the cells in the population express CD44.

* * * * *

SEQUENCE LISTING

<160> NUMBER OF SEQ ID NOS: 6

<210> SEQ ID NO 1
<211> LENGTH: 4742
<212> TYPE: DNA
<213> ORGANISM: Artificial Sequence
<220> FEATURE:
<223> OTHER INFORMATION: Synthetic DNA encoding His6-tagged T2 TrpRS

<400> SEQUENCE: 1

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg      180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta taaggatttt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg agacaataac cctgataaat gcttcaataa tattgaaaaa ggaagagtat     600
gagtattcaa catttccgtg tcgcccttat tcccttttt gcggcatttt gccttcctgt     660
ttttgctcac ccagaaacgc tggtgaaagt aaaagatgct gaagatcagt tgggtgcacg     720
agtgggttac atcgaactgg atctcaacag cggtaagatc cttgagagtt tcgccccga     780 agaacgtttt ccaatgatga gcactttaa agttctgcta tgtggcgcgg tattatcccg     840
tattgacgcc gggcaagagc aactcggtcg ccgcatacac tattctcaga atgacttggt     900
tgagtactca ccagtcacag aaaagcatct tacggatggc atgacagtaa gagaattatg     960
cagtgctgcc ataaccatga gtgataacac tgcggccaac ttacttctga caacgatcgg    1020
aggaccgaag gagctaaccg cttttttgca acatggggg atcatgtaa ctcgccttga    1080 tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
```

```
ccggcaacaa ttaatagact ggatggaggc ggataaagtt gcaggaccac ttctgcgctc   1260
ggcccttccg gctggctggt ttattgctga taaatctgga gccggtgagc gtgggtctcg   1320
cggtatcatt gcagcactgg ggccagatgg taagccctcc cgtatcgtag ttatctacac   1380
gacggggagt caggcaacta tggatgaacg aaatagacag atcgctgaga taggtgcctc   1440
actgattaag cattggtaac tgtcagacca agtttactca tatatacttt agattgattt   1500
aaaacttcat ttttaattta aaaggatcta ggtgaagatc cttttttgata atctcatgac   1560 caaaatccct taacgtgagt tttcgttcca ctgagcgtca gaccccgtag aaaagatcaa   1620
aggatcttct tgagatcctt tttttctgcg cgtaatctgc tgcttgcaaa caaaaaaacc   1680
accgctacca gcggtggttt gtttgccgga tcaagagcta ccaactcttt ttccgaaggt   1740
aactggcttc agcagagcgc agataccaaa tactgtcctt ctagtgtagc cgtagttagg   1800
ccaccacttc aagaactctg tagcaccgcc tacatacctc gctctgctaa tcctgttacc   1860
agtggctgct gccagtggcg ataagtcgtg tcttaccggg ttggactcaa gacgatagtt   1920
accggataag gcgcagcggt cgggctgaac ggggggttcg tgcacacagc ccagcttgga   1980
gcgaacgacc tacaccgaac tgagatacct acagcgtgag ctatgagaaa gcgccacgct   2040
tcccgaaggg agaaaggcgg acaggtatcc ggtaagcggc agggtcggaa caggagagcg   2100
cacgagggag cttccagggg gaaacgcctg gtatctttat agtcctgtcg ggtttcgcca   2160
cctctgactt gagcgtcgat ttttgtgatg ctcgtcaggg gggcggagcc tatggaaaaa   2220
cgccagcaac gcggcctttt tacggttcct ggccttttgc tggccttttg ctcacatgtt   2280
ctttcctgcg ttatcccctg attctgtgga taaccgtatt accgcctttg agtgagctga   2340
taccgctcgc cgcagccgaa cgaccgagcg cagcgagtca gtgagcgagg aagcggaaga   2400
gcgcctgatg cggtattttc tccttacgca tctgtgcggt atttcacacc gcatatatgg   2460
tgcactctca gtacaatctg ctctgatgcc gcatagttaa gccagtatac actccgctat   2520
cgctacgtga ctgggtcatg gctgcgcccc gacacccgcc aacacccgct gacgcgccct   2580
gacgggcttg tctgctcccg gcatccgctt acagacaagc tgtgaccgtc tccgggagct   2640
gcatgtgtca gaggttttca ccgtcatcac cgaaacgcgc gaggcagctg cggtaaagct   2700
catcagcgtg tcgtgaagc gattcacaga tgtctgcctg ttcatccgcg tccagctcgt   2760
tgagtttctc cagaagcgtt aatgtctggc ttctgataaa gcgggccatg ttaagggcgg   2820
ttttttcctg tttggtcact gatgcctccg tgtaaggggg attctgttc atggggggtaa   2880 tgataccgat gaaacgagag aggatgctca cgatacgggt tactgatgat gaacatgccc   2940
ggttactgga acgttgtgag ggtaaacaac tggcggtatg gatgcggcgg gaccagagaa   3000
aaatcactca gggtcaatgc cagcgcttcg ttaatacaga tgtaggtgtt ccacagggta   3060
gccagcagca tcctgcgatg cagatccgga acataatggt gcagggcgct gacttccgcg   3120
tttccagact ttacgaaaca cggaaaccga agaccattca tgttgttgct caggtcgcag   3180
acgttttgca gcagcagtcg cttcacgttc gctcgcgtat cggtgattca ttctgctaac   3240
cagtaaggca acccccgccag cctagccggg tcctcaacga caggagcacg atcatgcgca   3300
cccgtggcca ggacccaacg ctgcccgaga tctcgatccc gcgaaattaa tacgactcac   3360
tatagggaga ccacaacggt ttccctctag aaataatttt gtttaacttt aagaaggaga   3420
tatacatatg agtgcaaaag gcatagacta cgataagctc attgttcggt ttggaagtag   3480
taaaattgac aaagagctaa taaaccgaat agagagagcc accggccaaa gaccacacca   3540
cttcctgcgc agaggcatct tcttctcaca cagagatatg aatcaggttc ttgatgccta   3600
```

-continued

```
tgaaaataag aagccatttt atctgtacac gggccggggc ccctcttctg aagcaatgca    3660
tgtaggtcac ctcattccat ttattttcac aaagtggctc caggatgtat ttaacgtgcc    3720
cttggtcatc cagatgacgg atgacgagaa gtatctgtgg aaggacctga ccctggacca    3780
ggcctatggc gatgctgttg agaatgccaa ggacatcatc gcctgtggct ttgacatcaa    3840
caagactttc atattctctg acctggacta catggggatg agctcaggtt tctacaaaaa    3900
tgtggtgaag attcaaaagc atgttacctt caaccaagtg aaaggcattt tcggcttcac    3960
tgacagcgac tgcattggga agatcagttt tcctgccatc caggctgctc cctccttcag    4020
caactcattc ccacagatct tccgagacag gacggatatc cagtgcctta tcccatgtgc    4080
cattgaccag gatccttact ttagaatgac aagggacgtc gcccccagga tcggctatcc    4140
taaaccagcc ctgttgcact ccaccttctt cccagccctg cagggcgccc agaccaaaat    4200
gagtgccagc gacccaaact cctccatctt cctcaccgac acggccaagc agatcaaaac    4260
caaggtcaat aagcatgcgt tttctggagg gagagacacc atcgaggagc acaggcagtt    4320
tgggggcaac tgtgatgtgg acgtgtcttt catgtacctg accttcttcc tcgaggacga    4380
cgacaagctc gagcagatca ggaaggatta ccagcggga gccatgctca ccggtgagct    4440
caagaaggca ctcatagagg ttctgcagcc cttgatcgca gagcaccagg cccggcgcaa    4500
ggaggtcacg gatgagatag tgaaagagtt catgactccc cggaagctgt ccttcgactt    4560
tcagaagctt gcggccgcac tcgagcacca ccaccaccac cactgagatc cggctgctaa    4620
caaagcccga aaggaagctg agttggctgc tgccaccgct gagcaataac tagcataacc    4680
ccttggggcc tctaaacggg tcttgagggg ttttttgctg aaaggaggaa ctatatccgg    4740
at                                                                   4742
```

<210> SEQ ID NO 2
<211> LENGTH: 392
<212> TYPE: PRT
<213> ORGANISM: Artificial Sequence
<220> FEATURE:
<223> OTHER INFORMATION: His6-tagged T2 TrpRS

<400> SEQUENCE: 2

```
Met Ser Ala Lys Gly Ile Asp Tyr Asp Lys Leu Ile Val Arg Phe Gly
1               5                   10                  15

Ser Ser Lys Ile Asp Lys Glu Leu Ile Asn Arg Ile Glu Arg Ala Thr
            20                  25                  30

Gly Gln Arg Pro His His Phe Leu Arg Arg Gly Ile Phe Phe Ser His
        35                  40                  45

Arg Asp Met Asn Gln Val Leu Asp Ala Tyr Glu Asn Lys Lys Pro Phe
    50                  55                  60

Tyr Leu Tyr Thr Gly Arg Gly Pro Ser Ser Glu Ala Met His Val Gly
65                  70                  75                  80

His Leu Ile Pro Phe Ile Phe Thr Lys Trp Leu Gln Asp Val Phe Asn
                85                  90                  95

Val Pro Leu Val Ile Gln Met Thr Asp Asp Glu Lys Tyr Leu Trp Lys
            100                 105                 110

Asp Leu Thr Leu Asp Gln Ala Tyr Gly Asp Ala Val Glu Asn Ala Lys
        115                 120                 125

Asp Ile Ile Ala Cys Gly Phe Asp Ile Asn Lys Thr Phe Ile Phe Ser
    130                 135                 140

Asp Leu Asp Tyr Met Gly Met Ser Ser Gly Phe Tyr Lys Asn Val Val
145                 150                 155                 160
```

Lys Ile Gln Lys His Val Thr Phe Asn Gln Val Lys Gly Ile Phe Gly
                165                 170                 175

Phe Thr Asp Ser Asp Cys Ile Gly Lys Ile Ser Phe Pro Ala Ile Gln
            180                 185                 190

Ala Ala Pro Ser Phe Ser Asn Ser Phe Pro Gln Ile Phe Arg Asp Arg
        195                 200                 205

Thr Asp Ile Gln Cys Leu Ile Pro Cys Ala Ile Asp Gln Asp Pro Tyr
    210                 215                 220

Phe Arg Met Thr Arg Asp Val Ala Pro Arg Ile Gly Tyr Pro Lys Pro
225                 230                 235                 240

Ala Leu Leu His Ser Thr Phe Phe Pro Ala Leu Gln Gly Ala Gln Thr
                245                 250                 255

Lys Met Ser Ala Ser Asp Pro Asn Ser Ser Ile Phe Leu Thr Asp Thr
            260                 265                 270

Ala Lys Gln Ile Lys Thr Lys Val Asn Lys His Ala Phe Ser Gly Gly
        275                 280                 285

Arg Asp Thr Ile Glu Glu His Arg Gln Phe Gly Gly Asn Cys Asp Val
    290                 295                 300

Asp Val Ser Phe Met Tyr Leu Thr Phe Phe Leu Glu Asp Asp Asp Lys
305                 310                 315                 320

Leu Glu Gln Ile Arg Lys Asp Tyr Thr Ser Gly Ala Met Leu Thr Gly
                325                 330                 335

Glu Leu Lys Lys Ala Leu Ile Glu Val Leu Gln Pro Leu Ile Ala Glu
            340                 345                 350

His Gln Ala Arg Arg Lys Glu Val Thr Asp Glu Ile Val Lys Glu Phe
        355                 360                 365

Met Thr Pro Arg Lys Leu Ser Phe Asp Phe Gln Lys Leu Ala Ala Ala
    370                 375                 380

Leu Glu His His His His His His
385                 390

<210> SEQ ID NO 3
<211> LENGTH: 378
<212> TYPE: PRT
<213> ORGANISM: Homo sapiens

<400> SEQUENCE: 3

Ser Ala Lys Gly Ile Asp Tyr Asp Lys Leu Ile Val Arg Phe Gly Ser
1               5                   10                  15

Ser Lys Ile Asp Lys Glu Leu Ile Asn Arg Ile Glu Arg Ala Thr Gly
            20                  25                  30

Gln Arg Pro His His Phe Leu Arg Arg Gly Ile Phe Phe Ser His Arg
        35                  40                  45

Asp Met Asn Gln Val Leu Asp Ala Tyr Glu Asn Lys Lys Pro Phe Tyr
    50                  55                  60

Leu Tyr Thr Gly Arg Gly Pro Ser Ser Glu Ala Met His Val Gly His
65                  70                  75                  80

Leu Ile Pro Phe Ile Phe Thr Lys Trp Leu Gln Asp Val Phe Asn Val
                85                  90                  95

Pro Leu Val Ile Gln Met Thr Asp Asp Glu Lys Tyr Leu Trp Lys Asp
            100                 105                 110

Leu Thr Leu Asp Gln Ala Tyr Ser Tyr Ala Val Glu Asn Ala Lys Asp
        115                 120                 125

Ile Ile Ala Cys Gly Phe Asp Ile Asn Lys Thr Phe Ile Phe Ser Asp
    130                 135                 140

```
Leu Asp Tyr Met Gly Met Ser Ser Gly Phe Tyr Lys Asn Val Val Lys
145                 150                 155                 160

Ile Gln Lys His Val Thr Phe Asn Gln Val Lys Gly Ile Phe Gly Phe
                165                 170                 175

Thr Asp Ser Asp Cys Ile Gly Lys Ile Ser Phe Pro Ala Ile Gln Ala
            180                 185                 190

Ala Pro Ser Phe Ser Asn Ser Phe Pro Gln Ile Phe Arg Asp Arg Thr
        195                 200                 205

Asp Ile Gln Cys Leu Ile Pro Cys Ala Ile Asp Gln Asp Pro Tyr Phe
    210                 215                 220

Arg Met Thr Arg Asp Val Ala Pro Arg Ile Gly Tyr Pro Lys Pro Ala
225                 230                 235                 240

Leu Leu His Ser Thr Phe Phe Pro Ala Leu Gln Gly Ala Gln Thr Lys
                245                 250                 255

Met Ser Ala Ser Asp Pro Asn Ser Ser Ile Phe Leu Thr Asp Thr Ala
            260                 265                 270

Lys Gln Ile Lys Thr Lys Val Asn Lys His Ala Phe Ser Gly Gly Arg
        275                 280                 285

Asp Thr Ile Glu Glu His Arg Gln Phe Gly Gly Asn Cys Asp Val Asp
    290                 295                 300

Val Ser Phe Met Tyr Leu Thr Phe Phe Leu Glu Asp Asp Lys Leu
305                 310                 315                 320

Glu Gln Ile Arg Lys Asp Tyr Thr Ser Gly Ala Met Leu Thr Gly Glu
                325                 330                 335

Leu Lys Lys Ala Leu Ile Glu Val Leu Gln Pro Leu Ile Ala Glu His
            340                 345                 350

Gln Ala Arg Arg Lys Glu Val Thr Asp Glu Ile Val Lys Glu Phe Met
        355                 360                 365

Thr Pro Arg Lys Leu Ser Phe Asp Phe Gln
    370                 375

<210> SEQ ID NO 4
<211> LENGTH: 378
<212> TYPE: PRT
<213> ORGANISM: Homo sapiens

<400> SEQUENCE: 4

Ser Ala Lys Gly Ile Asp Tyr Asp Lys Leu Ile Val Arg Phe Gly Ser
1               5                   10                  15

Ser Lys Ile Asp Lys Glu Leu Ile Asn Arg Ile Glu Arg Ala Thr Gly
            20                  25                  30

Gln Arg Pro His His Phe Leu Arg Arg Gly Ile Phe Phe Ser His Arg
        35                  40                  45

Asp Met Asn Gln Val Leu Asp Ala Tyr Glu Asn Lys Pro Phe Tyr
    50                  55                  60

Leu Tyr Thr Gly Arg Gly Pro Ser Ser Glu Ala Met His Val Gly His
65                  70                  75                  80

Leu Ile Pro Phe Ile Phe Thr Lys Trp Leu Gln Asp Val Phe Asn Val
                85                  90                  95

Pro Leu Val Ile Gln Met Thr Asp Asp Glu Lys Tyr Leu Trp Lys Asp
            100                 105                 110

Leu Thr Leu Asp Gln Ala Tyr Gly Asp Ala Val Glu Asn Ala Lys Asp
        115                 120                 125

Ile Ile Ala Cys Gly Phe Asp Ile Asn Lys Thr Phe Ile Phe Ser Asp
    130                 135                 140
```

-continued

```
Leu Asp Tyr Met Gly Met Ser Ser Gly Phe Tyr Lys Asn Val Val Lys
145                 150                 155                 160

Ile Gln Lys His Val Thr Phe Asn Gln Val Lys Gly Ile Phe Gly Phe
                165                 170                 175

Thr Asp Ser Asp Cys Ile Gly Lys Ile Ser Phe Pro Ala Ile Gln Ala
            180                 185                 190

Ala Pro Ser Phe Ser Asn Ser Phe Pro Gln Ile Phe Arg Asp Arg Thr
        195                 200                 205

Asp Ile Gln Cys Leu Ile Pro Cys Ala Ile Asp Gln Asp Pro Tyr Phe
    210                 215                 220

Arg Met Thr Arg Asp Val Ala Pro Arg Ile Gly Tyr Pro Lys Pro Ala
225                 230                 235                 240

Leu Leu His Ser Thr Phe Phe Pro Ala Leu Gln Gly Ala Gln Thr Lys
                245                 250                 255

Met Ser Ala Ser Asp Pro Asn Ser Ser Ile Phe Leu Thr Asp Thr Ala
            260                 265                 270

Lys Gln Ile Lys Thr Lys Val Asn Lys His Ala Phe Ser Gly Gly Arg
        275                 280                 285

Asp Thr Ile Glu Glu His Arg Gln Phe Gly Gly Asn Cys Asp Val Asp
    290                 295                 300

Val Ser Phe Met Tyr Leu Thr Phe Phe Leu Glu Asp Asp Lys Leu
305                 310                 315                 320

Glu Gln Ile Arg Lys Asp Tyr Thr Ser Gly Ala Met Leu Thr Gly Glu
                325                 330                 335

Leu Lys Lys Ala Leu Ile Glu Val Leu Gln Pro Leu Ile Ala Glu His
            340                 345                 350

Gln Ala Arg Arg Lys Glu Val Thr Asp Glu Ile Val Lys Glu Phe Met
        355                 360                 365

Thr Pro Arg Lys Leu Ser Phe Asp Phe Gln
    370                 375

<210> SEQ ID NO 5
<211> LENGTH: 423
<212> TYPE: PRT
<213> ORGANISM: Homo sapiens

<400> SEQUENCE: 5

Ser Tyr Lys Ala Ala Ala Gly Glu Asp Tyr Lys Ala Asp Cys Pro Pro
1               5                   10                  15

Gly Asn Pro Ala Pro Thr Ser Asn His Gly Pro Asp Ala Thr Glu Ala
            20                  25                  30

Glu Glu Asp Phe Val Asp Pro Trp Thr Val Gln Thr Ser Ser Ala Lys
        35                  40                  45

Gly Ile Asp Tyr Asp Lys Leu Ile Val Arg Phe Gly Ser Ser Lys Ile
    50                  55                  60

Asp Lys Glu Leu Ile Asn Arg Ile Glu Arg Ala Thr Gly Gln Arg Pro
65                  70                  75                  80

His His Phe Leu Arg Arg Gly Ile Phe Phe Ser His Arg Asp Met Asn
                85                  90                  95

Gln Val Leu Asp Ala Tyr Glu Asn Lys Lys Pro Phe Tyr Leu Tyr Thr
            100                 105                 110

Gly Arg Gly Pro Ser Ser Glu Ala Met His Val Gly His Leu Ile Pro
        115                 120                 125

Phe Ile Phe Thr Lys Trp Leu Gln Asp Val Phe Asn Val Pro Leu Val
    130                 135                 140
```

Ile Gln Met Thr Asp Asp Glu Lys Tyr Leu Trp Lys Asp Leu Thr Leu
145                 150                 155                 160

Asp Gln Ala Tyr Ser Tyr Ala Val Glu Asn Ala Lys Asp Ile Ile Ala
                165                 170                 175

Cys Gly Phe Asp Ile Asn Lys Thr Phe Ile Phe Ser Asp Leu Asp Tyr
            180                 185                 190

Met Gly Met Ser Ser Gly Phe Tyr Lys Asn Val Val Lys Ile Gln Lys
        195                 200                 205

His Val Thr Phe Asn Gln Val Lys Gly Ile Phe Gly Phe Thr Asp Ser
    210                 215                 220

Asp Cys Ile Gly Lys Ile Ser Phe Pro Ala Ile Gln Ala Ala Pro Ser
225                 230                 235                 240

Phe Ser Asn Ser Phe Pro Gln Ile Phe Arg Asp Arg Thr Asp Ile Gln
                245                 250                 255

Cys Leu Ile Pro Cys Ala Ile Asp Gln Asp Pro Tyr Phe Arg Met Thr
            260                 265                 270

Arg Asp Val Ala Pro Arg Ile Gly Tyr Pro Lys Pro Ala Leu Leu His
        275                 280                 285

Ser Thr Phe Phe Pro Ala Leu Gln Gly Ala Gln Thr Lys Met Ser Ala
    290                 295                 300

Ser Asp Pro Asn Ser Ser Ile Phe Leu Thr Asp Thr Ala Lys Gln Ile
305                 310                 315                 320

Lys Thr Lys Val Asn Lys His Ala Phe Ser Gly Gly Arg Asp Thr Ile
                325                 330                 335

Glu Glu His Arg Gln Phe Gly Gly Asn Cys Asp Val Asp Val Ser Phe
            340                 345                 350

Met Tyr Leu Thr Phe Phe Leu Glu Asp Asp Lys Leu Glu Gln Ile
        355                 360                 365

Arg Lys Asp Tyr Thr Ser Gly Ala Met Leu Thr Gly Glu Leu Lys Lys
        370                 375                 380

Ala Leu Ile Glu Val Leu Gln Pro Leu Ile Ala Glu His Gln Ala Arg
385                 390                 395                 400

Arg Lys Glu Val Thr Asp Glu Ile Val Lys Glu Phe Met Thr Pro Arg
                405                 410                 415

Lys Leu Ser Phe Asp Phe Gln
            420

<210> SEQ ID NO 6
<211> LENGTH: 401
<212> TYPE: PRT
<213> ORGANISM: Homo sapiens

<400> SEQUENCE: 6

Ser Asn His Gly Pro Asp Ala Thr Glu Ala Glu Glu Asp Phe Val Asp
1               5                   10                  15

Pro Trp Thr Val Gln Thr Ser Ser Ala Lys Gly Ile Asp Tyr Asp Lys
                20                  25                  30

Leu Ile Val Arg Phe Gly Ser Ser Lys Ile Asp Lys Glu Leu Ile Asn
            35                  40                  45

Arg Ile Glu Arg Ala Thr Gly Gln Arg Pro His His Phe Leu Arg Arg
        50                  55                  60

Gly Ile Phe Phe Ser His Arg Asp Met Asn Gln Val Leu Asp Ala Tyr
65                  70                  75                  80

Glu Asn Lys Lys Pro Phe Tyr Leu Tyr Thr Gly Arg Gly Pro Ser Ser
                85                  90                  95

```
Glu Ala Met His Val Gly His Leu Ile Pro Phe Ile Phe Thr Lys Trp
            100                 105                 110

Leu Gln Asp Val Phe Asn Val Pro Leu Val Ile Gln Met Thr Asp Asp
            115                 120                 125

Glu Lys Tyr Leu Trp Lys Asp Leu Thr Leu Asp Gln Ala Tyr Ser Tyr
            130                 135                 140

Ala Val Glu Asn Ala Lys Asp Ile Ile Ala Cys Gly Phe Asp Ile Asn
145                 150                 155                 160

Lys Thr Phe Ile Phe Ser Asp Leu Asp Tyr Met Gly Met Ser Ser Gly
                165                 170                 175

Phe Tyr Lys Asn Val Val Lys Ile Gln Lys His Val Thr Phe Asn Gln
            180                 185                 190

Val Lys Gly Ile Phe Gly Phe Thr Asp Ser Asp Cys Ile Gly Lys Ile
            195                 200                 205

Ser Phe Pro Ala Ile Gln Ala Ala Pro Ser Phe Ser Asn Ser Phe Pro
    210                 215                 220

Gln Ile Phe Arg Asp Arg Thr Asp Ile Gln Cys Leu Ile Pro Cys Ala
225                 230                 235                 240

Ile Asp Gln Asp Pro Tyr Phe Arg Met Thr Arg Asp Val Ala Pro Arg
                245                 250                 255

Ile Gly Tyr Pro Lys Pro Ala Leu Leu His Ser Thr Phe Phe Pro Ala
            260                 265                 270

Leu Gln Gly Ala Gln Thr Lys Met Ser Ala Ser Asp Pro Asn Ser Ser
            275                 280                 285

Ile Phe Leu Thr Asp Thr Ala Lys Gln Ile Lys Thr Lys Val Asn Lys
    290                 295                 300

His Ala Phe Ser Gly Gly Arg Asp Thr Ile Glu Glu His Arg Gln Phe
305                 310                 315                 320

Gly Gly Asn Cys Asp Val Asp Val Ser Phe Met Tyr Leu Thr Phe Phe
                325                 330                 335

Leu Glu Asp Asp Asp Lys Leu Glu Gln Ile Arg Lys Asp Tyr Thr Ser
            340                 345                 350

Gly Ala Met Leu Thr Gly Glu Leu Lys Lys Ala Leu Ile Glu Val Leu
            355                 360                 365

Gln Pro Leu Ile Ala Glu His Gln Ala Arg Arg Lys Glu Val Thr Asp
            370                 375                 380

Glu Ile Val Lys Glu Phe Met Thr Pro Arg Lys Leu Ser Phe Asp Phe
385                 390                 395                 400

Gln
```